US012590339B2

(12) United States Patent
White et al.

(10) Patent No.: US 12,590,339 B2
(45) Date of Patent: Mar. 31, 2026

(54) METHOD FOR MULTIPLEXED DETECTION OF NUCLEIC ACIDS USING SPECTRALLY ENCODED BEADS

(71) Applicants: CZ Biohub SF, LLC, San Francisco, CA (US); The Board of Trustees of the Leland Stanford Junior University, Stanford, CA (US)

(72) Inventors: Adam K. White, Stanford, CA (US); Huy Q. Nguyen, Stanford, CA (US); Feiqiao Brian Yu, San Francisco, CA (US); Tyler Shimko, Stanford, CA (US); Polly M. Fordyce, Stanford, CA (US); Nadya Andini, Stanford, CA (US); Samuel Yang, Stanford, CA (US); Gaeun Kim, Stanford, CA (US)

(73) Assignees: CZ Biohub SF, LLC, San Francisco, CA (US); The Board of Trustees of the Leland Stanford Junior University, Stanford, CA (US)

( * ) Notice: Subject to any disclaimer, the term of this patent is extended or adjusted under 35 U.S.C. 154(b) by 992 days.

(21) Appl. No.: 17/613,676

(22) PCT Filed: May 27, 2020

(86) PCT No.: PCT/US2020/034747
§ 371 (c)(1),
(2) Date: Nov. 23, 2021

(87) PCT Pub. No.: WO2020/243200
PCT Pub. Date: Dec. 3, 2020

(65) Prior Publication Data
US 2022/0228198 A1      Jul. 21, 2022

Related U.S. Application Data

(60) Provisional application No. 62/853,494, filed on May 28, 2019.

(51) Int. Cl.
| | | |
|---|---|---|
| *C12Q 1/689* | (2018.01) | |
| *C12Q 1/6816* | (2018.01) | |
| *C12Q 1/6834* | (2018.01) | |

(52) U.S. Cl.
CPC ........... *C12Q 1/689* (2013.01); *C12Q 1/6816* (2013.01); *C12Q 1/6834* (2013.01); *C12Q 2600/16* (2013.01)

(58) Field of Classification Search
CPC ..... C12Q 1/689; C12Q 1/6816; C12Q 1/6834
See application file for complete search history.

(56) References Cited

U.S. PATENT DOCUMENTS

| | | | |
|---|---|---|---|
| 8,293,472 B2 | 10/2012 | Moser | |
| 9,170,197 B2 | 10/2015 | Geddes et al. | |

(Continued)

FOREIGN PATENT DOCUMENTS

| | | | | |
|---|---|---|---|---|
| WO | WO-2008073624 A2 * | 6/2008 | ........... | C12Q 1/6816 |
| WO | 2017015177 | 1/2017 | | |
| WO | 2018213604 | 11/2018 | | |

OTHER PUBLICATIONS

Abdelrahman, A.I. "Lanthanide-encoded polystyrene microspheres for mass cytometry-based bioassays", University of Toronto Graduate Department of Chemistry Dissertation/Thesis, 220 pages, Library and Archives of Canada. (Year: 2011).*

(Continued)

*Primary Examiner* — Diana B Johannsen
(74) *Attorney, Agent, or Firm* — Kilpatrick Townsend & Stockton LLP

(57)        ABSTRACT

Methods for characterizing a population of microbes in a sample are described. The methods include: amplifying microbial polynucleotides obtained from the sample to form a plurality of amplicons and combining the amplicons with a plurality of microbeads, wherein each of the microbeads has a lanthanide spectral signature paired with the sequence (Continued)

1. PCR with universal primers generates fluorescent strand and phosphorylated strand 2. Exonuclease treatment to remove phosphorylated strand 3. Hybridization of PCR products to specific oligonucleotide sequences on encoded beads 4. Imaging: Spectral code links fluorescence to oligo sequence for 16S rDNA variant identification 60 min
30 min
30 min
2 hr total Oligo Library Bead Multiplexing Assays 1 = ATCGAACATT
2 = AATCGCCTTA
3 = CCTTATGTAT
4 = GCTGCATGAG
47 = GACCCTTAG
48 = GAGTTAGCG Imaging bead codes DNA detection (fluorescence)

of capture polynucleotides immobilized on the microbead. At least some of the capture polynucleotides comprise a sequence substantially complementary to a microbe-identifying sequence in one or more amplicons, such that at least some amplicons are captured onto beads by the capture polynucleotides and the microbe can be identified based on the lanthanide spectral signature of with which the capture polynucleotide is paired. Further described are methods for the identification of pathogens present in a sample by evaluating patterns of hybridization of a capture oligonucleotide to amplicons. Microbead compositions and methods for the preparation thereof are also described.

20 Claims, 19 Drawing Sheets

Specification includes a Sequence Listing.

(56) References Cited

U.S. PATENT DOCUMENTS

| | | | |
|---|---|---|---|
| 9,528,145 | B2 | 12/2016 | Bisso et al. |
| 2009/0291858 | A1 | 11/2009 | Andersen et al. |
| 2015/0192518 | A1 | 7/2015 | Baxter et al. |

OTHER PUBLICATIONS

Rasooly, A. and Herold, K.E. Foodborne Pathogens and Disease 5(4):531. (Year: 2008).*

Aghazadeh, A. et al. Sci. Adv. 2:e1600025 (9 pages). Sep. 2016. (Year: 2016).*

Wang, X. et al. International Journal of Food Microbiology 237:172. (Year: 2016).*

International Application No. PCT/US2020/034747, International Search Report and Written Opinion mailed on Oct. 22, 2020, 16 pages.

Biliveau et al., Oligominer Provides a Rapid, Flexible Environment for the Design of Genome-Scale Oligonucleotide in Situ Hybridization Probes, Proceedings of the National Academy of Sciences of the United States of America, vol. 115, No. 10, Mar. 6, 2018, pp. E2183-E2192.

Brower et al., Multi-Step Variable Height Photolithography for Valved Multilayer Microfluidic Devices, Journal of Visualized Experiments, vol. 2017, No. 119, Jan. 27, 2017, pp. 1-12.

Gerver et al., Programmable Microfluidic Synthesis of Spectrally Encoded Microspheres, Lab Chip, vol. 12, No. 22, Nov. 21, 2012, pp. 4716-4723.

Krimmer et al., Detection of *Staphylococcus eureus* and *Staphylococcus epidermidis* in Clinical Samples by 16S rRNA-directed In Situ Hybridization, Journal of Clinical Microbiology vol. 37, No. 8, Aug. 1999, pp. 2667-2673.

Kumar et al., Highly Sensitive and Selective Label-Free Optical Detection of DNA Hybridization Based on Photon Upconverting Nanoparticles, Langmuir, vol. 25, No. 11, Apr. 28, 2009, pp. 6024-6027.

Kumar et al., Highly Sensitive and Selective Oligonucleotide Sensor for Sickle Cell Disease Gene Using Photon Upconverting Nanoparticles, Biosens Bioelectron, vol. 24, No. 5, Jan. 1, 2009, pp. 1522-1526.

Letowski et al., Designing Better Probes: Effect of Probe Size, Mismatch Position and Number on Hybridization in DNA Oligonucleotide Microarrays, Journal of Microbiological Methods, vol. 57, No. 2, May 2004, pp. 269-278.

Matveeva et al., Sequence Characteristics Define Trade-Offs Between on-Target and Genome-wide Off-Target Hybridization of Oligoprobes, PloS one vol. 13, No. 6, Jun. 21, 2018, pp. 1-20.

Nguyen et al., Programmable Microfluidic Synthesis of Over One Thousand Uniquely Identifiable Spectral Codes, Advanced Optical Materials, vol. 5, No. 3, Feb. 2017, pp. 1-6.

Nguyen et al., Quantitative Mapping of Protein-peptide Affinity Landscapes Using Spectrally Encoded Beads, eLife, bioRxiv, Jul. 8, 2019, 24 pages.

Samanta et al., Nanoparticles and DNA—A Powerful and Growing Functional Combination in Bionanotechnology, Nanoscale, vol. 8, No. 17, Apr. 28, 2016, pp. 9037-9095.

Yilamz et al., Mechanistic Approach to the Problem of Hybridization Efficiency in Fluorescent In Situ Hybridization, Applied and Environmental Microbiology, vol. 70, No. 12, Dec. 1, 2004, pp. 7126-7139.

Zhang et al., Design of a Highly Sensitive and Specific Nucleotide Sensor Based on Photon Upconverting Particles, Journal of the American Chemical Society, vol. 128, No. 38, Aug. 31, 2006, pp. 12410-12411.

Klamp, et al., Highly Rapid Amplification-Free and Quantitative DNA Imaging Assay, Scientific Reports, vol. 3, May 16, 2013, 7 pages.

Harink, et al., An Open-Source Software Analysis Package for Microspheres with Ratiometric Barcode Lanthanide Encoding (MRBLEs), PLOS ONE, vol. 14, No. 3, Mar. 22, 2019, 20 pages.

* cited by examiner

1. Determine K-mer length to uniquely separate targets

2. Find locations of uniquely identifying K-mers

3. Identify maximally separating K-mer per oligo

4. Perform sliding window probe design (similar to primer design)

5. Return list of potential hybridization oligos for further pruning and selection

FIG. 2C

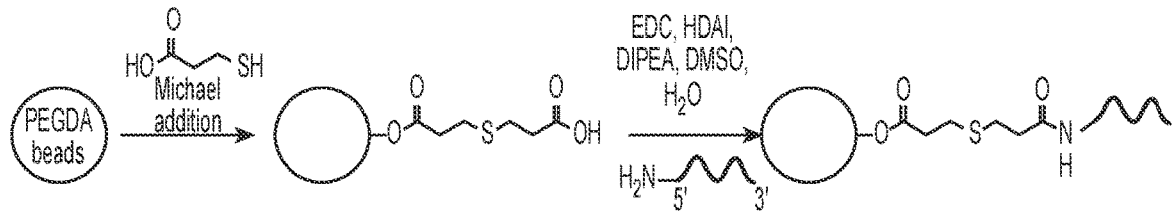
FIG. 3A
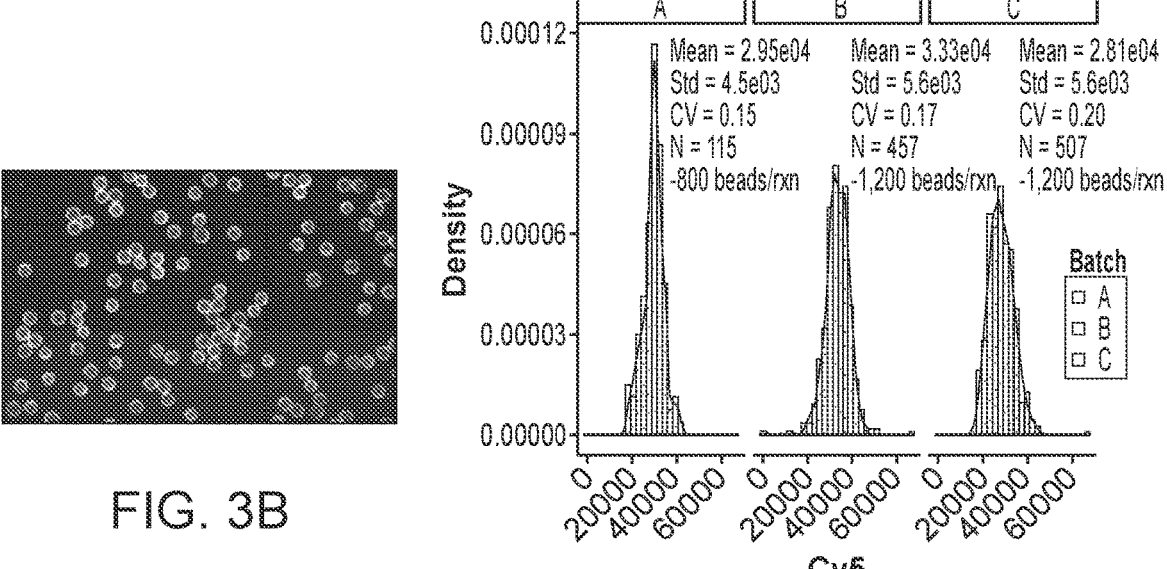
FIG. 3B
FIG. 3C
FIG. 3D

METHOD FOR MULTIPLEXED DETECTION OF NUCLEIC ACIDS USING SPECTRALLY ENCODED BEADS

CROSS-REFERENCE TO RELATED APPLICATIONS

This application is a national phase application of PCT Application No. PCT/US2020/034747, filed May 27, 2020, which claims priority benefit of U.S. Provisional Patent Application No. 62/853,494, filed May 28, 2019, which is incorporated by reference in its entirety for all purposes.

STATEMENT AS TO RIGHTS TO INVENTIONS MADE UNDER FEDERALLY SPONSORED RESEARCH AND DEVELOPMENT

This invention was made with government support under Grant No. GM123641 awarded by the National Institutes of Health. The government has certain rights in the invention

REFERENCE TO AN ELECTRONIC SEQUENCE LISTING

The contents of the electronic sequence listing (103182-1190364-002110WO_SL.txt; Size: 71,210 bytes; and Date of Creation: Jul. 2, 2020) is herein incorporated by reference in its entirety

BACKGROUND OF THE INVENTION

Sepsis causes millions of deaths globally each year and is the leading cause of death in people who have been hospitalized. In sepsis, the time to antibiotic treatment is critical for patient survival, as the difference of an hour can mean life or death. However, as antibiotics are effective against only certain classes of microbial infections, the choice of appropriate treatment requires knowledge of the pathogen responsible. Such knowledge limits the use of inappropriate antibiotics that can have significant side effects and drive hospital-acquired resistance. The current gold-standard method in clinical use for identifying pathogens in blood infections relies on cultures that can take days, too slow to affect the initial antibiotic selection. To address this, several recent nucleic acid-based technologies have emerged, but none completely meet this urgent need. PCR-based nucleic acid tests can identify bacterial sequences in clinical samples in hours, but are limited to detecting ~1-4 pathogens simultaneously. In order to test for multiple pathogens, these methods typically require sample-splitting and compartmentalization into multiple different reactions, and this statistical sampling of blood volumes lowers the overall sensitivity of these assays and therefore requires pre-amplification steps that can complicate detection and lead to false-positive detections. Recently developed approaches that rely on next-generation sequencing enable unbiased (although still targeted) pathogen discovery and can detect a large number of potential pathogens, but take many hours to days.

BRIEF SUMMARY OF THE INVENTION

Provided herein are methods for characterizing a population of microbial strains in a sample. The different microbial strains contain polynucleotides with different microbe-identifying sequences, and the methods include:

(i) amplifying polynucleotides obtained from the sample to form a plurality of amplicons, wherein the amplicons comprise microbe-identifying sequences;

(ii) combining the amplicons with a plurality of microbeads, wherein each of the microbeads has a lanthanide spectral signature and a plurality of copies of a capture polynucleotide immobilized on the microbead, wherein each of the capture polynucleotides comprises a predetermined sequence, wherein each predetermined sequence is paired with a specific lanthanide spectral signature, such that the capture polynucleotide immobilized on a microbead can be identified based on the lanthanide spectral signature of the microbead, wherein at least some of the capture polynucleotides comprise a sequence substantially complementary to a microbe-identifying sequence of one or more amplicons, wherein the combining is conducted under conditions in which at least some amplicons are captured onto the beads by the capture polynucleotides, thereby producing captured amplicons, and wherein the amplicons are labeled with one or more signal-generating moieties prior to, simultaneously with, or after being captured onto the beads, such that microbeads comprising immobilized signal-generating moieties are produced;

(iii) detecting signal from immobilized signal-generating moieties of individual microbeads from step (ii); and (iv) determining the lanthanide spectral signatures of the individual microbeads from step (ii), thereby determining the microbe-identifying sequences of the captured amplicons and characterizing the population of microbial strains in the sample.

In one approach, step (iii) occurs prior to step (iv). In another approach, step (iii) occurs simultaneously with step (iv). In yet another approach, step (iii) occurs after step (iv).

In some instances, the amplicons are captured by hybridization of microbe-identifying sequences in the amplicons to the substantially complementary sequences in the capture polynucleotides.

In one aspect, the polynucleotides in step (i) are DNA. In another aspect, the polynucleotides in step (i) are RNA.

In some instances, the plurality of microbeads comprises at least 50 different spectral signatures and immobilized capture polynucleotides comprising at least 50 different predetermined sequences. In some instances, the combining in step (ii) comprises hybridizing amplicons to at least 50 microbeads having different spectral signatures and different capture polynucleotides.

In one approach, the signal-generating moiety produces a fluorescent or chemiluminscent signal. In one approach, the amplicons are labeled during the amplifying in step (i). In one approach, the magnitude of signal detected from an individual microbead in step (iii) corresponds to the amount of the amplicons captured on the microbead.

In some instances, the population of microbial strains comprise bacterials strains. In some instance, at least one of the microbe identifying sequences in the amplicons comprises a bacterial 16S ribosomal RNA (rRNA) gene sequence. In some instances, the amplification is conducted using primer pairs that hybridize to conserved regions flanking one or more variable regions in a bacterial 16S rRNA gene sequence. In some instances, the amplification in step (i) comprises amplifying a V3 variable region, a V4 variable region, or a V6 variable region in a bacterial 16S rRNA gene sequence. In one approach, at least one of the microbe indentifying sequences in the amplicons comprises an antibiotic resistance gene sequence. In some instances, the microbial strains comprise one or more species selected from the group consisting of *Pseudomonas, Streptococcus, Staphylococcus, Neisseria, Acinetobacter, Escherichia, Enterobacter,* and *Klebsiella.*

In some instances, each of the lanthanide spectral signatures comprises a europium (Eu) signal, a dysprosium (Dy) signal, a samarium (Sm) signal, a cerium (Ce) signal, a terbium (Tb) signal, a lanthanum (La) signal, a praseodymium (Pr) signal, a neodymium (Nd) signal, a gadolinium (Gd) signal, a holmium (Ho) signal, an erbium (Er) signal, a thulium (Tm) signal, an ytterbium (Yb) signal, or a combination thereof. In some instances, each of the microbeads comprises a plurality of lanthanide nanoparticles. In some instances, the lanthanide nanoparticle comprises a lanthanide-doped host lattice. In some instances, the host lattice is yttrium orthovanadate, lanthanum phosphate, or a combination thereof.

In some instances, each of the microbeads further comprises a crosslinked polymer, and the capture polynucleotides are covalently bonded to the crosslinked polymer.

In some instances, the plurality of microbeads are dispersed on a microscope slide prior to step (iii) or step (iv).

In some instances, the method according to the present disclosure further comprises separating uncaptured amplicons from microbeads having captured amplicons. In some instances, the method further comprises separating microbeads having immobilized signal-generating moieties from microbeads not having immobilized signal-generating moieties. In one aspect, the immobilized signal-generating moieties are fluorescent labels. In one approach, the immobilized signal-generating moieties are detected in step (iii) via fluorescence microscopy.

In some instances, the sample is a biological sample from an animal, a food sample, a beverage sample, or an environmental sample. In some aspects, the biological sample is a blood sample, an intestinal sample, a stool sample, a urine sample, a saliva sample, or a sputum sample.

Also provided herein are microbeads comprising a lanthanide spectral signature and a plurality of copies of a capture polynucleotide immobilized on the microbeads, wherein each capture polynucleotide comprises a predetermined sequence and each capture polynucleotide is paired with a lanthanide spectral signature, such that the predetermined sequence can be identified based on the lanthanide spectral signature.

In some instances, each capture polynucleotide comprises a nucleic acid sequence that hybridizes to a bacterial 16S rRNA gene sequence. In some instances, the capture polynucleotides comprise a nucleic acid sequence that hybridizes to a V3 variable region, a V4 variable region, or a V6 variable regions in a bacterial 16S rRNA gene sequence. In some instances, each of the capture polynucleotides comprises a nucleic acid sequence able to hybridize a *Pseudomonas* gene sequence, a *Streptococcus* gene sequence, *Staphylococcus* gene sequence, a *Neisseria* gene sequence, an *Acinetobacter* gene sequence, an *Escherichia* gene sequence, an *Enterobacter* gene sequence, or a *Klebsiella* gene sequence.

In some instances, each of the lanthanide spectral signatures comprises one or more signals selected from a europium (Eu) signal, a dysprosium (Dy) signal, a samarium (Sm) signal, a cerium (Ce) signal, a terbium (Tb) signal, a lanthanum (La) signal, a praseodymium (Pr) signal, a neodymium (Nd) signal, a gadolinium (Gd) signal, a holmium (Ho) signal, an erbium (Er) signal, a thulium (Tm) signal, and an ytterbium (Yb) signal. In some instances, each of the microbeads comprises a plurality of lanthanide nanoparticles. In some instances, the lanthanide nanoparticles comprise a lanthanide-doped host lattice. In some instances, the host lattice is yttrium orthovanadate, lanthanum phosphate, or a combination thereof. In some instances, each of the microbeads further comprise a crosslinked polymer, and the capture polynucleotides are covalently bonded to the crosslinked polymer. In some instances, the microbeads comprise at least 20 lanthanide spectral signatures. In some instances, the microbeads comprise at least 1000 lanthanide spectral signatures.

In another aspect, provided is a method for characterizing a population of microbial strains in a sample. The different microbial strains contain polynucleotides with different microbe-identifying sequences, and the methods include:

(i) amplifying polynucleotides obtained from the sample to form a plurality of amplicons, wherein the amplicons comprise microbe-identifying sequences;

(ii) combining the amplicons with a panel of microbeads, wherein each of the microbeads has a lanthanide spectral signature and a plurality of copies of a capture polynucleotide immobilized on the microbead, wherein each of the capture polynucleotides comprises a predetermined sequence, wherein each predetermined sequence is paired with a specific lanthanide spectral signature, such that the capture polynucleotide immobilized on a microbead can be identified based on the lanthanide spectral signature of the microbead, wherein at least some of the capture polynucleotides comprise a sequence substantially complementary to a microbe-identifying sequence of one or more amplicons, wherein the combining is conducted under conditions in which at least some amplicons hybridize to the capture polynucleotides, thereby producing captured amplicons, and wherein the amplicons are labeled with one or more signal-generating moieties prior to, simultaneously with, or after being captured onto the beads, such that microbeads comprising immobilized signal-generating moieties are produced; wherein the magnitude of signal detected from an individual microbead corresponds to the amount of the amplicons captured on the microbead.

(iii) measuring the magnitude of the signal from immobilized signal-generating moieties of individual microbeads from step (ii);

(iv) determining the lanthanide spectral signatures of the individual microbeads from step (ii), thereby determining the microbe-identifying sequences of the captured amplicons;

(v) generating a pattern of measured amount of hybridization of the captured amplicons to individual capture polynucleotides;

(vi) comparing the pattern of hybridization measured in (v) to a predicted pattern of hybridization of amplicons to each capture oligonucleotide, wherein prediction of the pattern of hybridization of the amplicons to a capture oligonucleotide comprises calculating the level of hybridization of the capture oligonucleotide to the amplicons, e.g., by calculating the Gibbs free energy of hybridization; and (vii) correlating the pattern of hybridization measured in (v) to the predicted pattern of hybridization for each species to identify the species that has a predicted pattern of hybridization that has the strongest correlation with the pattern of hybridization measured in (v).

In some instances, step (iii) occurs prior to step (iv). In some instances, step (iii) occurs simultaneously with step (iv). In some instances, step (iii) occurs after step (iv).

In some instances, the polynucleotides in step (i) are DNA.

In some instances, the plurality of microbeads comprises at least 50 different spectral signatures and immobilized capture polynucleotides comprising at least 50 different predetermined sequences. In some instances, the combining in step (ii) comprises hybridizing amplicons to at least 50 microbeads having different spectral signatures and different capture polynucleotides.

In some instances, the signal-generating moiety produces a fluorescent or chemiluminscent signal. In some instances, the amplicons are labeled during the amplifying in step (i).

In some instances, the population of microbial strains comprises bacterial strains. In one aspect, at least one of the microbe identifying sequences in the amplicons comprises a bacterial 16S ribosomal RNA (rRNA) gene sequence. In some instances, the amplification is conducted using primer pairs that hybridize to conserved regions flanking one or more variable regions in a bacterial 16S rRNA gene sequence. In some instances, the amplification in step (i) comprises amplifying one or more of a V3 variable region, a V4 variable region, or a V6 variable region in a bacterial 16S rRNA gene sequence. In some instances, the amplification step (i) comprises amplifying the V3 variable region and the V6 variable region. In some instances, the microbial strains comprise one or more species selected from the group consisting of *Pseudomonas, Streptococcus, Staphylococcus, Neisseria, Acinetobacter, Escherichia, Enterobacter, Klebsiella, Haemophilus, Proteus, Serratia, Enterococcus*, and *Listeria*.

In some instances, each of the lanthanide spectral signatures comprises a europium (Eu) signal, a dysprosium (Dy) signal, a samarium (Sm) signal, a cerium (Ce) signal, a terbium (Tb) signal, a lanthanum (La) signal, a praseodymium (Pr) signal, a neodymium (Nd) signal, a gadolinium (Gd) signal, a holmium (Ho) signal, an erbium (Er) signal, a thulium (Tm) signal, an ytterbium (Yb) signal, or a combination thereof. In some instances, each of the microbeads comprises a plurality of lanthanide nanoparticles. In some instances, the lanthanide nanoparticle comprises a lanthanide-doped host lattice. In some instances, the host lattice is yttrium orthovanadate, lanthanum phosphate, or a combination thereof. In one aspect, each of the microbeads further comprises a crosslinked polymer, and the capture polynucleotides are covalently bonded to the crosslinked polymer. In some instances, the plurality of microbeads are dispersed on a microscope slide prior to step (iii) or step (iv).

In some instances, the method further comprises separating uncaptured amplicons from microbeads having captured amplicons. In some instances, the method further comprises separating microbeads having immobilized signal-generating moieties from microbeads not having immobilized signal-generating moieties. In one aspect, the immobilized signal-generating moieties are fluorescent labels. In one aspect, the immobilized signal-generating moieties are measured in step (iii) via fluorescence microscopy.

In some instances, the sample is from blood, cerebrospinal fluid, lymph, or urine.

BRIEF DESCRIPTION OF THE DRAWINGS

FIG. 1 discloses SEQ ID NOs: 282-285, respectively, in order of appearance.

FIG. 2C shows an alignment of 16S variable region V6 for several species of bacteria.

FIG. 2C discloses SEQ ID NOs: 286-295, respectively, in order of appearance.

FIG. 3A shows a scheme for microbead functionalization.

FIG. 3B shows a fluorescence microgram of microbeads following hybridization of Cy5-labeled oligonucleotides.

FIG. 3C shows fluorescence signal intensity of microbeads following hybridization of Cy5-labeled oligonucleotides.

FIG. 3D shows that the fluorescence signal from the beads correlates to the amount of input oligonucleotide.

DETAILED DESCRIPTION OF THE INVENTION

Figure 1:
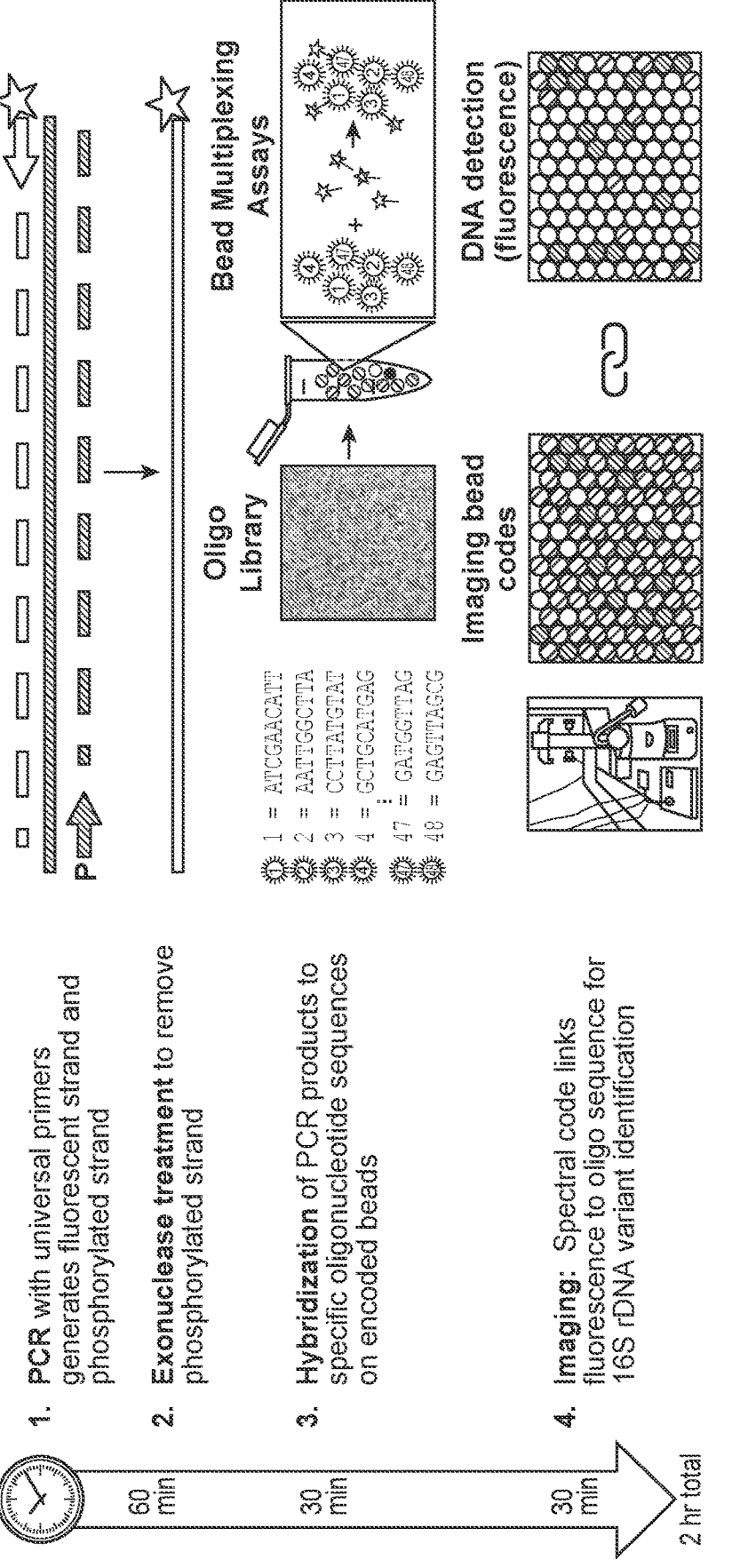
FIG. 1 shows a schematic representation of assays according to the present disclosure.

Provided herein are highly multiplexed, sensitive, specific, and fast methods for the detection of pathogens without blood compartmentalization for use clinical such as suspected cases of sepsis. These new methods, useful in rapid screening for the presence of multiple bacteria species in a single reaction, employ microfluidically synthesized beads embedded with distinct spectral codes. The methods can be used to detect different bacterial species in a variety of samples (e.g., clinical samples such as blood or stool, and environmental samples such as water or food sources) in multiplexed fashion, allowing for screen the parallel screening of large numbers samples (e.g., 96 samples or more) against a pathogen panels in short timeframes (e.g., 2 hours or less). This is already beyond the current throughput and multiplexing provided by conventional methods. The methods can also be used for identifying further characteristics such as the presence of antibiotic-resistant bacteria.

Beads according to the present disclosure are chemically compatible with wide variety of solvents and reagents, and bead sets can be prepared with over 1100 distinct spectral codes. Assays according to the present disclosure are economical, easy to use, compatible with standard laboratory equipment, and adaptable to a variety of assays. The assays are less expensive than DNA sequencing, and a higher number of DNA sequences may be targeted than by conventional PCR assays.

I. DEFINITIONS

As used herein, the term "sample" refers to a specimen that is suspected of containing microbial nucleic acids. Samples include, but are not limited to, clinical samples, food samples, and water samples, as described in more detail below.

As used herein, the term "microbial strain" refers to a strain of bacterium, virus, fungus, protist, or other microscopic organism.

As used herein, the term "microbead" refers to a particle having one or more dimensions (e.g., length, width, diameter, or circumference) of about 1000 μm or less, e.g., less than about 500 μm, 100 μm, or 10 μm. Microbeads may have a generally spherical shape or a non-spherical shape. Microbeads used in the methods of the present disclosure are characterized by a detectable spectral signature as described in more detail below.

As used herein, the term "nanoparticle" refers to a particle having at least one dimension (e.g., length, width, diameter, or circumference) ranging from 1 to 1,000 nm. Nanoparticles may have a generally spherical shape or a non-spherical shape. A "plurality" of nanoparticles refers to a population of microbeads ranging in size from a few nanoparticles to thousands of nanoparticles, or more.

As used herein, the term "host lattice" refers to a material having constituent atoms packed in a regularly ordered, repeating pattern which can accommodate the incorporation of lanthanide atoms or ions. By "lanthanide-doped," it is meant that the host lattice material contains lanthanide atoms or ions.

As used herein, the terms "polynucleotide" and "nucleic acid" refer to DNA or RNA, including, for example, genomic DNA; complementary DNA (cDNA); and DNA molecules produced synthetically or by amplification. Polynucleotides may be single-stranded or double-stranded. The term "microbial polynucleotide" refers to a polynucleotide originating from a strain of bacterium, virus, fungus, protist, or other microscopic organism.

As used herein, the term "microbe-identifying sequence" refers to a polynucleotide sequence that is characteristic of the microbial strain from which the polynucleotide originated. For example, a microbe-identifying sequence may be unique to a particular bacterial strain, allowing the strain to be positively identified upon finding the microbe-identifying sequence in a sample obtained from a source suspected to contain the strain. The microbe-identifying sequences may range from around five bases in length to hundreds of bases in length.

As used herein, the term "capture polynucleotide" refers to an oligonucleotide containing a predetermined sequence selected to hybridize to a microbe-identifying sequence in an amplicon. The terms "hybridize," "anneal," and "bind," in reference to two polynucleotide sequences, are used interchangeably and have the usual meaning in the art. Two complementary sequences (e.g., DNA and/or RNA) anneal or hybridize by forming hydrogen bonds with complementary bases to produce a double-stranded polynucleotide or a double-stranded region of a polynucleotide.

The predetermined sequence of a capture polynucleotide is selected such that is complementary or substantially complementary to a microbe-identifying sequence suspected to be present in a sample under study. The term "substantially complementary," in the context of a capture oligonucleotide, refers to a sequence that is not perfectly complementary to its target sequence, but can hybridize selectively to the desired target sequences. Such a sequence may have one or more "mismatches", i.e., one or more positions in which the nucleotide in the capture polynucleotide and the nucleotide in the target amplicon with which it is aligned are not complementary. Selectivity of hybridization exists when hybridization occurs that is more selective than total lack of specificity. Typically, selective hybridization will occur when there is at least about 55% identity over a stretch of at least 14-25 nucleotides, e.g., at least about 65%, at least about 75%, or at least about 90% identity. See, M. Kanehisa, Nucleic Acids Res. 12:203 (1984).

As used herein, the term "immobilized" refers to a substance (e.g., a capture polynucleotide or signal-generating moiety) which is covalently bonded to microbeads, or non-covalently bound such that it is not unintentionally removed during characterization of the sample under study (e.g., during amplification, combination, labeling, and/or detection steps as described herein).

As used herein, the terms "amplifying" and "amplification reaction" refer to a process whereby a portion of a target polynucleotide is replicated using a primer extension reaction such as a polymerase chain reaction (PCR). Amplifying the polynucleotide can include a single replication, as well as arithmetic, logarithmic, or exponential amplification. The term "amplicon" refers to the portion of a target polynucleotide that is replicated in an amplification reaction. Amplicons generated in the methods of the present disclosure typically range from tens of bases in length to hundreds of bases in length, or more.

As used herein, the term "predetermined" refers to a nucleotide sequence that has been specifically selected for hybridization to an amplicon sequence suspected to arise from an amplification reaction conducted with a particular sample. For example, predetermined sequences may be selected for hybridization to known bacterial gene sequences as described herein.

As used herein, the term "lanthanide spectral signature" refers to the combined luminescent signals in the range of 350-850 nm emitted from lanthanide nanoparticles contained in a single microbead upon excitation with an appropriate wavelength of light, e.g., UV light (e.g., 292 nm for excitation of downconverting lanthanides) or IR light (e.g., 980 nm for excitation of upconverting lanthanides). The luminescence intensity at a characteristic wavelength or wavelengths (e.g., 620 nm, 630 nm, or 650 nm) for a particular lanthanide (e.g., Eu) indicates the presence and quantity of the particular lanthanide in the source (e.g., a microbead) from which the spectral signature originates. As used herein, the term "lanthanide" refers to elements 57-71 of the periodic table, namely lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), and lutetium (Lu).

The term "paired," in the context of a spectral signature and the capture oligonucleotides for a particular microbead, refers to a microbead having a known spectral signature and copies of a capture oligonucleotide having a known predetermined sequence immobilized thereto. Because both the spectral signature and the predetermined sequence are known, the identity of the predetermined sequence can be determined based on the features of the spectral signature (e.g., the luminescence intensity at one or more characteristic wavelengths for one or more particular lanthanides).

The term "label," as used herein, refers to any atom or molecule that can be used to provide a detectable and/or quantifiable signal. In some embodiments, the label can be attached, directly or indirectly, to a biomolecule. Labels include, but are not limited to, radioisotopes, fluorophores, chromophores, mass labels, electron dense particles, magnetic particles, spin labels, molecules that emit chemiluminescence, electrochemically active molecules, enzymes, cofactors, and enzyme substrates.

II. EMBODIMENTS OF THE INVENTION

Provided herein are methods for characterizing a population of microbial strains in a sample. The different microbial strains contain polynucleotides with different microbe-identifying sequences, and the methods include:

(i) amplifying polynucleotides obtained from the sample to form a plurality of amplicons, wherein the amplicons comprise microbe-identifying sequences;

(ii) combining the amplicons with a plurality of microbeads, wherein each of the microbeads has a lanthanide spectral signature and a plurality of copies of a capture polynucleotide immobilized on the microbead, wherein each of the capture polynucleotides comprises a predetermined sequence, wherein each predetermined sequence is paired with a specific lanthanide spectral signature, such that the capture polynucleotide immobilized on a microbead can be identified based on the lanthanide spectral signature of the microbead, wherein at least some of the capture polynucleotides comprise a sequence substantially complementary to a microbe-identifying sequence of one or more amplicons, wherein the combining is conducted under conditions in which at least some amplicons are captured onto the beads by the capture polynucleotides, thereby producing captured amplicons, and wherein the amplicons are labeled with one or more signal-generating moieties prior to, simultaneously with, or after being captured onto the beads, such that microbeads comprising immobilized signal-generating moieties are produced;

(iii) detecting signal from immobilized signal-generating moieties of individual microbeads from step (ii); and (iv) determining the lanthanide spectral signatures of the individual microbeads from step (ii), thereby determining the microbe-identifying sequences of the captured amplicons and characterizing the population of microbial strains in the sample.

The plurality of microbeads may range in population size. For example, a plurality of microbeads may include 10 or more, 100 or more, 500 or more, $10^3$ or more, $10^4$ or more, $10^5$ or more, $10^6$ or more, or 107 or more microbeads. The microbeads of the present disclosure generally have one or more dimensions (e.g., diameter) of about 1000 μm or less, e.g., about 500 μm or less, about 100 μm or less, about 50 μm or less, about 10 μm or less, or about 5 μm or less. For example, a microbead may have one or more dimensions (e.g., diameter) of from about 1000 μm to about 1 μm, from about 500 μm to about 1 μm, from about 100 μm to about 1 μm, from about 50 μm to about 1 μm, from about 10 μm to about 1 μm, or from about 5 μm to about 1 μm. The microbeads may have a generally spherical shape or a non-spherical shape. Each microbead in a plurality of microbeads may have approximately the same one or more dimensions. In some embodiments, individual microbeads have a diameter such that the diameter variation among all the members of the plurality is no greater than about 10 percent, e.g., no greater than about 5 percent, or no greater than about 1 percent.

A. Amplification of Microbial Nucleic Acids

A number of nucleic acid amplification methods can be used in the methods described herein, e.g., PCR and variations thereof (e.g., TaqMan, real time PCR, quantitative PCR), reverse transcription, strand displacement reaction (SDR), ligase chain reaction (LCR), transcription mediated amplification (TMA), Qbeta replication, hybridization chain reaction, recombinase polymerase amplification, or rolling circle amplification.

Samples from a variety of sources can be processed for use in the amplification reactions. In some embodiments, the sample is a blood sample, a stool sample, a urine sample, a saliva sample, a sputum sample, a food sample, a beverage sample, or an environmental sample (e.g., a soil sample, a water sample, an oil sample, or an agricultural sample). Bacterial DNA, for example, can be amplified from a clinical sample obtained from a septic patient. In some embodiments, a small portion of a clinical sample obtained from a subject can be used directly in the PCR mixture for amplification and detection of microbial nucleic acids. Alternatively, one or more nucleic acid purification steps can be conducted with body fluid sample prior to the amplification step in the method. In such cases, the sample may be a mixture containing purified microbial nucleic acids (if present) along with other nucleic acids associated with the sample (e.g., genomic DNA or a portion thereof from the subject). The term "purified," as used herein to refer to microbial nucleic acids purified from a sample, means that at least a portion of other components (e.g., polysaccharides, polypeptides, and the like) have been removed. In some embodiments, for example, the amount of protein in a purified DNA mixture will be less than 50% of the protein present in the initial sample from which the purified mixture is obtained. Purifying DNA from a sample can therefore include removing at least 50%, 60%, 70%, 80%, 90%, 95%, or 99% of the protein present in the sample. Protein concentrations can be determined by assay methods such as a Bradford assay, a Lowry assay, a BCA assay, or like similar techniques. Similarly, other carbohydrate, amino acid, and lipid components can be removed from body fluid samples during purification of nucleic acids.

For example, proteins and other contaminants can be removed from samples by extraction with phenol-chloroform or similar organic solvents, and the remaining DNA can be precipitated with an alcohol such as ethanol. Solid-phase adsorbent materials can also be employed for purification of nucleic acids from samples prior to PCR. Examples of such materials include, but are not limited to, silica or glass fibers/particles that are used in conjunction with chaotropic agents such as sodium iodide, guanidinium isothiocyanate, and the like. Commercially available materials designed for such protocols include ILLUSTRA GFX products (GE Life Sciences) and MONARCH nucleic acid purification products (New England BioLabs).

Different variable region sequences within the amplified portions of the 16S rRNA gene can be detected using microbeads having capture polynucleotides with predetermined sequences that are selected to specifically identify various bacterial species, e.g., *Pseudomonas* species, *Streptococcus* species, *Staphylococcus* species, *Neisseria* species, *Acinetobacter* species, *Escherichia* species, *Enterobacter* species, *Klebsiella* species, and combinations thereof. Polynucleotides from Gram positive and Gram negative bacteria can be assessed using the methods of the present disclosure. The bead compositions and methods disclosed herein can also be adapted to detect other infectious agents such as viruses, or to validate the presence of DNA sequences that are predicted from de novo metagenomic sequencing.

Figures 6, 7:
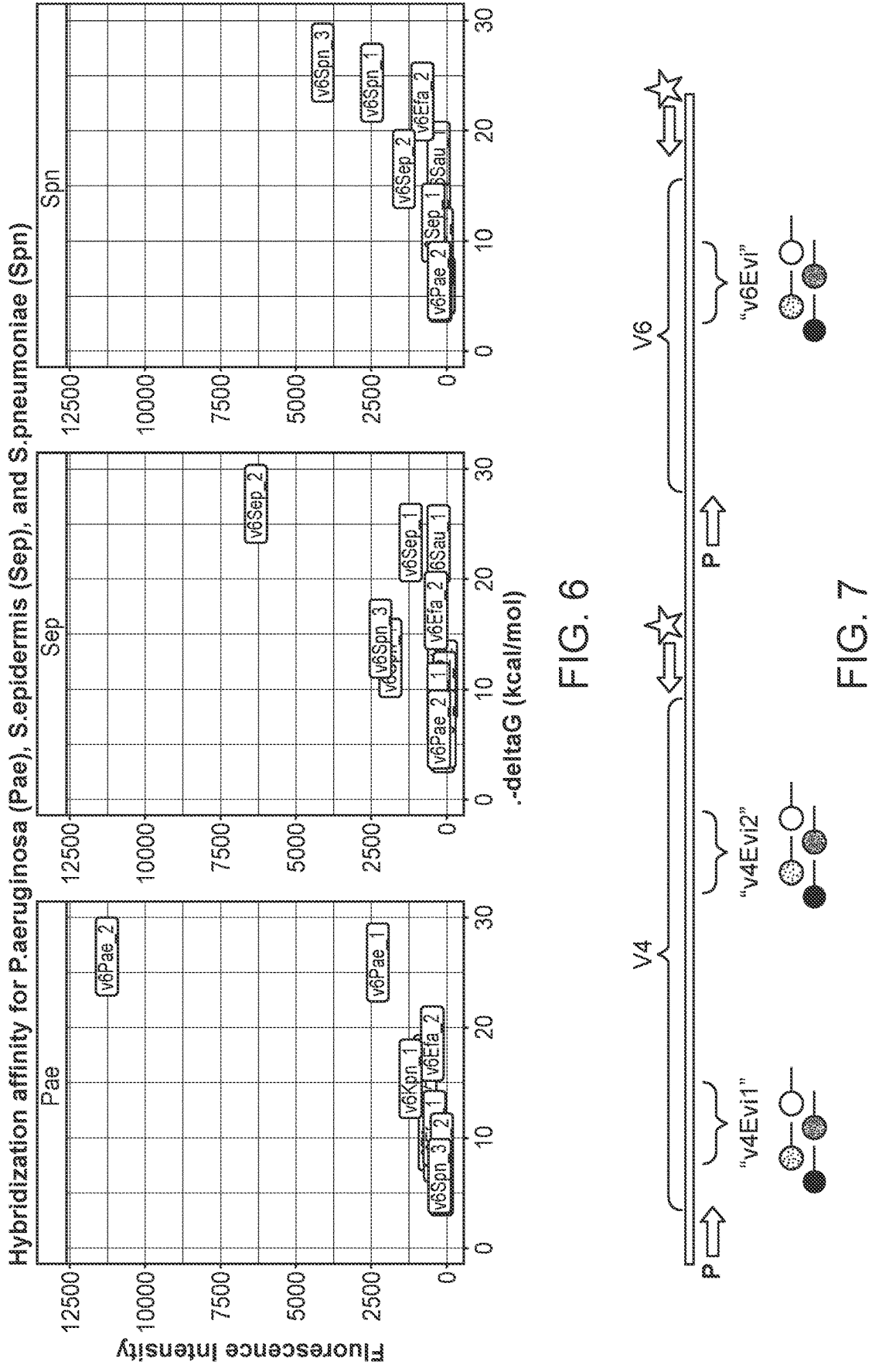
FIG. 6 shows that hybridization affinity is correlated with the free energy of hybridization.
FIG. 7 shows a schematic depiction of 16S rRNA gene targeting.
Figure 8:
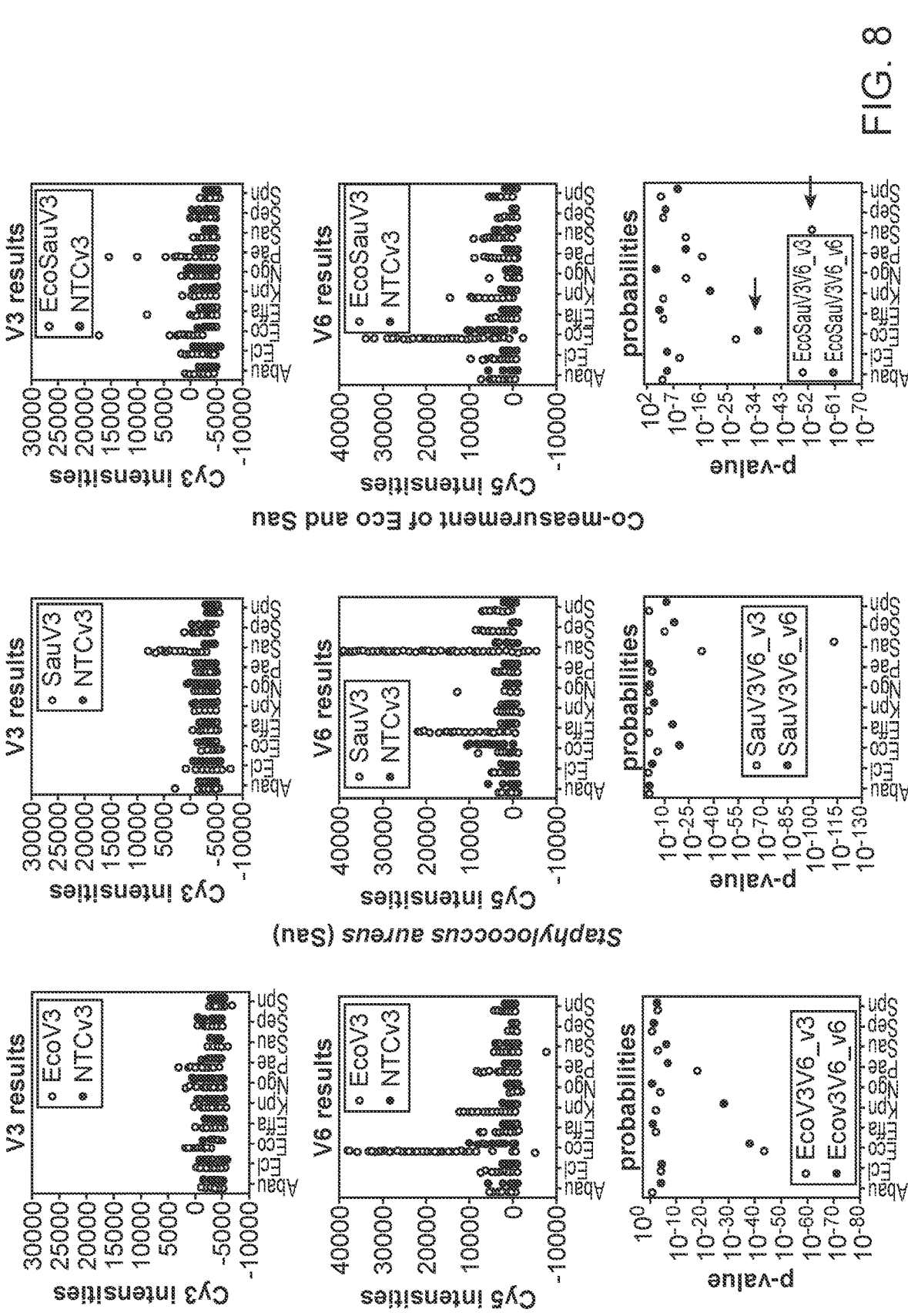
FIG. 8 shows the simultaneous measurement of multiple variable regions.

In some embodiments, the capture polynucleotides contain predetermined sequences that are present in any one or more variable regions V1-V9 of a bacterial 16S rRNA gene. By selecting a predetermined sequence (e.g., a sequence present within the V3 variable region, V4 variable region, or V6 variable region) that is unique for a particular species of bacteria, e.g., *Staphylococcus aureus*, that species can be identified as the cause of, or a contributor to, infection in a subject from whom a clinical sample under study has been obtained. Using the same capture polynucleotide sequence on beads having different spectral signatures can provide can provide technical replicates, as shown in FIG. 7. In addition, as shown in FIG. 8, simultaneous assessment of sequences in two or more variable regions (e.g., the V3 region using capture polynucleotides having one or more predetermined sequences set forth in Table 2 and the V6 region using capture polynucleotides having one or more predetermined sequences set forth in Table 3) can further increase confidence in pathogen detection, reduce false positives, and allow for discrimination between species that may be identical or extremely similar in one variable region but not another.

In some embodiments, at least one of the microbe identifying sequences in the amplicons comprises a bacterial 16S ribosomal RNA (rRNA) gene sequence. In some embodiments, the amplification is conducted using primer pairs that hybridize to conserved regions in a bacterial 16S rRNA gene sequence. As used herein, the term "conserved" refers to any sequence of bases in comparable segments of different nucleotides that tend to show similarity greater than that due to chance alone. In some embodiments, a conserved sequence flanks a known variable region in a bacterial gene such as a 16S rRNA gene. The amplification can be conducted using primer pairs that hybridize, for example, to conserved regions flanking: a V1 variable region corresponding to nucleotides 69-99 (numbering by the *E. coli* system of nomenclature; see, Brosius et al., 1978); a V2 variable region corresponding to nucleotides 137-242; a V3 variable region corresponding to nucleotides 433-497); a V4 variable region corresponding to nucleotides 576-682); a V5 variable region corresponding to nucleotides 822-879); a V6 variable region corresponding to nucleotides 986-1043); a V7 variable region corresponding to nucleotides 1117-1173); a V8 variable region corresponding to nucleotides 1243-1294); a V9 variable region corresponding to nucleotides 1435-1465); or two or more of these variable regions. For example, degenerate primers ("515F" having the sequence GTGCCAGCMGCCGCGGTAA, SEQ ID NO:1; and "806R" having the sequence GGAC-TACHVGGGTWTCTAAT, SEQ ID NO:2; see, Table 1) can anneal to common regions in the 16S gene to specifically amplify the V4 variable region. In some embodiments, the amplification in step (i) comprises amplifying a V3 variable region, a V4 variable region, or a V6 variable region in a bacterial 16S rRNA gene sequence. Alternatively, the entire 16S rRNA gene can be amplified and microbe-identifying sequences within the resulting amplicons can be identified by annealing to predetermined sequences in immobilized capture polynucleotides and analysis of the corresponding lanthanide spectral signatures. Non-limiting examples of primers for use in such embodiments include "27F" having the sequence AGRGTTYGATYMTGGCTCAG (SEQ ID NO:164) and "1492R" having the sequence RGYTACCTTGTTACGACTT (SEQ ID NO:165).

TABLE 1

Primer Sequences for Amplification of 16S rRNA Variable Regions.

| Description | Sequence | SEQ ID NO. |
|---|---|---|
| 515F(V4), labeled | /A647/GTGCCAGCMGCCGCGGTAA | 1 |
| 806R(V4), phosphorylated | /Phos/GGACTACHVGGGTWTCTAAT | 2 |
| 515F(V4) | GTGCCAGCMGCCGCGGTAA | 3 |
| 806R(V4), | GGACTACHVGGGTWTCTAAT | 4 |
| V6-Forward, labeled | /A647/TGGAGCATGTGGTTTAATTCGA | 5 |
| V6-Forward | TGGAGCATGTGGTTTAATTCGA | 6 |
| V6-Reverse, phosphorylated | /Phos/AGCTGACGACANCCATGCA | 7 |
| V6-Reverse | AGCTGACGACANCCATGCA | 8 |
| V3-Forward, labeled | /A647/CCAGACTCCTACGGGAGGCAG | 9 |
| V3-Forward | CCAGACTCCTACGGGAGGCAG | 10 |
| V3-Reverse, phosphorylated | /Phos/CGTATTACCGCGGCTGCTG | 11 |
| V3-Reverse | CGTATTACCGCGGCTGCTG | 12 |

As set forth above, the methods of the present disclosure generally include labeling amplicons with a signal-generating moiety, e.g., a moiety that produces a fluorescent or chemiluminescent signal which can then be detected on individual microbeads. Well-known fluorophores including, but not limited to, fluoresceins, rhodamines, eosins, cyanines, boron-dipyrromethenes, and coumarins can be used as signal generating moieties for labeling. Affinity tags such as biotin or haptens such as digoxygenin can be used for detection with labeled detection reagents such as streptavidin or antibodies. Labeling of the amplicons can occur before, during, or after combination with the microbeads. In some embodiments, the labeling in step (iii) is conducted during the amplifying in step (i). For example, the amplification can be conducted using a forward primer containing a 5'-label (e.g., a cyanine dye such as Cy5 or Alexa Fluor 647) as in SEQ ID NO: 1, SEQ ID NO: 5, and SEQ ID NO: 9. Oligonucleotides for preparation of labeled amplicons are available from commercial sources such as Integrated DNA Technologies, Inc. (Coralville, Iowa, USA). In some embodiments, labeled amplicons are prepared using forward primers containing a 5'-label and reverse primers containing a 5'-phosphate group, as in as in SEQ ID NO: 2, SEQ ID NO: 7, and SEQ ID NO: 11. Following amplification, remaining phosphorylated primers and corresponding amplicon strands containing 5'-phosphate groups can be digested by treatment with commercially-available bacteriophage lambda exonuclease. The exonuclease treatment can increase the amount of single stranded, fluorescently labeled amplicon available for highly efficient hybridization to capture polynucleotides on the microbeads.

Alternatively, labeling of the amplicons can occur after combination with the microbeads. For example, a DNA intercalator such as ethidium bromide or SYBR dye (e.g., SYBR Green I) can be used to identify amplicons that have formed double-stranded complexes with capture oligonucleotides on the microbeads.

TABLE 2

| Capture Polynucleotide Sequences for Hybridization to V6 Amplicons. | | | |
|---|---|---|---|
| Description | Species | Sequence | SEQ ID NO |
| v6Sau_1_1806 26, amine modified | *S. aureus* | /5AmMC12/TTTTTTTTCTAGAGTT GTCAAAGGATGTCAAGATTTGGT AAG | 13 |
| v6Sau_1_1806 26 | *S. aureus* | CTAGAGTTGTCAAAGGATGTCAA GATTTGGTAAG | 14 |
| v6Pae_1_1806 26, amine modified | *P. aeruginosa* | /5AmMC12/TTTTTTTACCTGTGTC TGAGTTCCCGAAGG | 15 |
| v6Pae_1_1806 26 | *P. aeruginosa* | ACCTGTGTCTGAGTTCCCGAAGG | 16 |
| v6Pae_2_1806 26, amine modified | *P. aeruginosa* | /5AmMC12/TTTTTTTTGGAAAGTT CTCAGCATGTCAAGGC | 17 |
| v6Pae_2_1806 26 | *P. aeruginosa* | GGAAAGTTCTCAGCATGTCAAGG C | 18 |
| v3Abau_3_18, amine modified 0626 | *A. baumannii* | /5AmMC12/TTTTTTTGCCGTATTA ACTAAATCCTCCTCGCTTAAAG | 19 |
| v3Abau_3_18 | *A. baumannii* | GCCGTATTAACTAAATCCTCCTC GCTTAAAG | 20 |
| v6Abau_1_18 0626, amine modified | *A. baumannii* | /5AmMC12/TTTTTTTTGGAAAGTT TCTAGTATGTCAAGGCCAGG | 21 |
| v6Abau_1_18 0626 | *A. baumannii* | GGAAAGTTTCTAGTATGTCAAGG CCAGG | 22 |
| v6Abau_2_18 0626, amine modified | *A. baumannii* | /5AmMC12/TTTTTTTGCACCTGTA TCTAGATTCCCGAAGG | 23 |
| v6Abau_2_18 0626 | *A. baumannii* | GCACCTGTATCTAGATTCCCGAA GG | 24 |
| v6Ecl_2_1806 26, amine modified | *E. cloaecae* | /5AmMC12/TTTTTTTTGCTAAGTT CTCTGGATGTCAAGAGTAGG | 25 |
| v6Ecl_2_1806 26 | *E. cloaecae* | GCTAAGTTCTCTGGATGTCAAGA GTAGG | 26 |
| v6Efa_2_1806 26, amine modified | *E. faecium* | /5AmMC12/TTTTTTTGACCTGGTA AGGTTCTTTCGCGTTG | 27 |
| v6Efa_2_1806 26 | *E. faecium* | GACCTGGTAAGGTTCTTTCGCGT TG | 28 |

TABLE 2-continued

Capture Polynucleotide Sequences for Hybridization to V6 Amplicons.

| Description | Species | Sequence | SEQ ID NO |
|---|---|---|---|
| v6Efa_3_1806 26, amine modified | *E. faecium* | /5AmMC12/TTTTTTTTAGAGTGGT CAAAGGATGTCAAGA | 29 |
| v6Efa_3_1806 26 | *E. faecium* | AGAGTGGTCAAAGGATGTCAAG A | 30 |
| v6Kpn_1_180 626, amine modified | *K. pneumoniae* | /5AmMC12/TTTTTTTTGTCTCACA GTTCCCGAAGGCA | 31 |
| v6Kpn_1_180 626 | *K. pneumoniae* | GTCTCACAGTTCCCGAAGGCA | 32 |
| v6Kpn_2_180 626, amine modified | *K. pneumoniae* | /5AmMC12/TTTTTTTTGGAAAGTT CTGTGGATGTCAAGA | 33 |
| v6Kpn_2_180 626 | *K. pneumoniae* | GGAAAGTTCTGTGGATGTCAAGA | 34 |
| v6Sep_1_1806 26, amine modified | *S. epidermis* | /5AmMC12/TTTTTTTGTCACTCTG TCCCCCGAAGG | 35 |
| v6Sep_1_1806 26 | *S. epidermis* | GTCACTCTGTCCCCCGAAGG | 36 |
| v6Sep_2_1806 26, amine modified | *S. epidermis* | /5AmMC12/TTTTTTTGAGGGGTCA GAGGATGTCAAGATTTG | 37 |
| v6Sep_2_1806 26 | *S. epidermis* | GAGGGGTCAGAGGATGTCAAGA TTTG | 38 |
| v6Spn_1_1806 26, amine modified | *S. pneumoniae* | /5AmMC12/TTTTTTTTGTCACCTCT GTCCCGAAGGAAA | 39 |
| v6Spn_1_1806 26 | *S. pneumoniae* | GTCACCTCTGTCCCGAAGGAAA | 40 |
| v6Spn_3_1806 26, amine modified | *S. pneumoniae* | /5AmMC12/TTTTTTTTAGAGCGGT CAGAGGGATGTCAAG | 41 |
| v6Spn_3_1806 26 | *S. pneumoniae* | AGAGCGGTCAGAGGGATGTCAA G | 42 |

TABLE 3

Capture Polynucleotide Sequences for Hybridization to V3 Amplicons.

| Description | Species | Sequence | SEQ ID NO. |
|---|---|---|---|
| v3Eco_n, amine modified | *E. coli* | /5AmMC12/TTTTTTTGAGCAAAGG TATTAACTTTACTCCCTTCC | 43 |
| v3Eco_n | *E. coli* | GAGCAAAGGTATTAACTTTACTC CCTTCC | 44 |
| v3Sau_n, amine modified | *S. aureus* | /5AmMC12/TTTTTTTGATGTGCAC AGTTACTTACACATATGT | 45 |
| v3Sau_n | *S. aureus* | GATGTGCACAGTTACTTACACAT ATGT | 46 |
| v3Pae_n, amine modified | *P. aeruginosa* | /5AmMC12/TTTTTTTGTATTAACT TACTGCCCTTCCTCCCAAC | 47 |

TABLE 3-continued

Capture Polynucleotide Sequences for Hybridization to V3 Amplicons.

| Description | Species | Sequence | SEQ ID NO. |
|---|---|---|---|
| v3Pae_n | P. aeruginosa | GTATTAACTTACTGCCCTTCCTCC CAAC | 48 |
| v3Abau_n, amine modified | A. baumannii | /5AmMC12/TTTTTTTCTATCTCTA GGTAGCCGTATTAACTAAA | 49 |
| v3Abau_n | A. baumannii | CTATCTCTAGGTAGCCGTATTAA CTAAA | 50 |
| v3Ecl_n, amine modified | E. cloaecae | /5AmMC12/TTTTTTTAGGGATGAA CAGTTACTCTCATCCT | 51 |
| v3Ecl_n | E. cloaecae | AGGGATGAACAGTTACTCTCATC CT | 52 |
| v3Efa_n, amine modified | E. faecium | /5AmMC12/TTTTTTTCGGCAGGGT TATTAACCCTGTCGC | 53 |
| v3Efa_n | E. faecium | CGGCAGGGTTATTAACCCTGTCG C | 54 |
| v3Kpn_n, amine modified | K. pneumoniae | /5AmMC12/TTTTTTTTCGACAAGG TTATTAACCTTATCG | 55 |
| v3Kpn_n | K. pneumoniae | CGACAAGGTTATTAACCTTATCG | 56 |
| v3Ngo_n, amine modified | N. gonorrhoeae | /5AmMC12/TTTTTTTCGGCCGCCG ATATTGGCAACGGCCTT | 57 |
| v3Ngo_n | N. gonorrhoeae | CGGCCGCCGATATTGGCAACGGC CTT | 58 |
| v3Sep_n, amine modified | S. epidermis | /5AmMC12/TTTTTTTGACGTGCAT AGTTACTTACACATTTG | 59 |
| v3Sep_n | S. epidermis | GACGTGCATAGTTACTTACACAT TTG | 60 |
| v3Spn_n, amine modified | S. epidermis | /5AmMC12/TTTTTTTCAGTGTGAA CTTTCCACTCTCACACTC | 61 |
| v3Spn_n | S. pneumoniae | CAGTGTGAACTTTCCACTCTCAC ACTC | 62 |

TABLE 4

Capture Polynucleotides for Hybridization to Amplicons Generated from Environmental Samples.

| Description | Sequence | Sample Type | SEQ ID NO. |
|---|---|---|---|
| #Ga0181610_1 0375322_v1 | GGACTACAGGGGTATCTAATCCCTTTTG | SS (Salton Sea water) | 63 |
| #Ga0181610_1 0375322_v2 | GGTGACAGGGGTTTACAATCCGAG | SS | 64 |
| #Ga0181610_1 0375322_v3 | GCGTTGCACCATCAGGGTTT | SS | 65 |
| #Ga0181610_1 0397925_v1 | CGGCTTCATGCAGTCGAGTTG | SS | 66 |

TABLE 4-continued

Capture Polynucleotides for Hybridization to Amplicons Generated
from Environmental Samples.

| Description | Sequence | Sample Type | SEQ ID NO. |
|---|---|---|---|
| #Ga0181610_1 0397925_v2 | CAGTGTACTCCGCTCCGAAGAG | SS | 67 |
| #Ga0181610_1 0397925_v3 | AGTAACTCCGAACAACGCTTGC | SS | 68 |
| #Ga0181610_1 0398315_v1 | GAACTGTGGCTGGGTTTGATGAGATT | SS | 69 |
| #Ga0181610_1 0398315_v2 | CATGCAGGCGAGTTTCAGCC | SS | 70 |
| #Ga0181610_1 0398315_v3 | CTTTTCGCTCCCCTTTGTCCCAA | SS | 71 |
| #Ga0181610_1 052119_v1 | GTCAATTCATTTGAGTTTTAACCTTGCG | SS | 72 |
| #Ga0181610_1 052119_v2 | AGCTCGCCAGTTTTGGATGCAG | SS | 73 |
| #Ga0181610_1 052119_v3 | AGTCGACATCGTTTACGGCGTG | SS | 74 |
| #Ga0181610_1 054535_v1 | GAACTGAGATGGCTTTTGGAGATTCG | SS | 75 |
| #Ga0181610_1 054535_v2 | GAGCCAGGATCAAACTCTCAGGTTT | SS | 76 |
| #Ga0181610_1 054535_v3 | GTCTGGCCGACATCGTTTACGG | SS | 77 |
| #Ga0181610_1 054817_v1 | TTAGCTTTTGTAGCCTTTTTCCCTGCTG | SS | 78 |
| #Ga0181610_1 054817_v2 | CGAACTCGAGTTTTGCAGTATCTAAAG C | SS | 79 |
| #Ga0181610_1 054817_v3 | AGGAATTCCGCTTGCTTTTCCCG | SS | 80 |
| #Ga0181610_1 060662_v1 | CAGTTACTAGTTTTACCCTAGGCAGC | SS | 81 |
| #Ga0181610_1 060662_v2 | GAACTGAGATAGTGTTTAAGGGATTCG C | SS | 82 |
| #Ga0181610_1 060662_v3 | ACGTAGAAGGGTTTATTCCCAAACAAA A | SS | 83 |
| #Ga0181610_1 064264_v1 | TACGACCGGTTTTTCGGGATTGG | SS | 84 |
| #Ga0181610_1 064264_v2 | ATGTCAAAGGTGGGTAAGGTTTTTCG | SS | 85 |
| #Ga0181610_1 064264_v3 | GACTACGACCGGTTTTTCGGGATTG | SS | 86 |
| #Ga0181610_1 076632_v1 | GATCGCTCCCTTTTACCTCTCGG | SS | 87 |
| #Ga0181610_1 076632_v2 | GGTAAGGTTCTTCGGTTTGCATCGAATT | SS | 88 |
| #Ga0181610_1 076632_v3 | GTACTCCAGTCCGACGGTTTCG | SS | 89 |
| #Ga0181610_1 079111_v1 | TGCAGCACCTGTGTTTAGGTT | SS | 90 |
| #Ga0181610_1 079111_v2 | GTTCTAGCAAGCTAGCACTCTCATATTT | SS | 91 |

TABLE 4-continued

Capture Polynucleotides for Hybridization to Amplicons Generated
from Environmental Samples.

| Description | Sequence | Sample Type | SEQ ID NO. |
|---|---|---|---|
| #Ga0181610_1 079334_V1 | CGGACTACGACGAGTTTTTTGGGATT | SS | 92 |
| #Ga0181610_1 081755_v1 | ATAGGGCTCGGCTTCATGCG | SS | 93 |
| #Ga0181610_1 081755_v2 | ATATCACTATAGGGCTCGGCTTCATGC | SS | 94 |
| #Ga0181610_1 081755_v3 | TATAGGGCTCGGCTTCATGCG | SS | 95 |
| #Ga0181610_1 082181_v1 | GAGACCGGCTTTTTGGGATTTGC | SS | 96 |
| #Ga0181610_1 082181_v2 | AACTGAGACCGGCTTTTTGGGATTTG | SS | 97 |
| #Ga0181610_1 082181_0 | tCtCCTTTCAGGAAGAGGCCCCCTTTT | SS | 98 |
| #Ga0181610_1 087371_v1 | CATCAGTCCTTTTTCCCCGACAAAAGG | SS | 99 |
| #Ga0181610_1 087371_v2 | CCATCAGTCCTTTTTCCCCGACAAAAG | SS | 100 |
| #Ga0181610_1 087371_v3 | tCtCGGTTGAGCCGTGGTATTTTACGC | SS | 101 |
| #Ga0181610_1 090741_v1 | tCGCTACTGATCGTCGCCATGGTAAG | SS | 102 |
| #Ga0181610_1 09080141_v1 | TTTCCTTACTCACCATGCAGTAAGTAAT | SS | 103 |
| #Ga0181610_1 09080141_v2 | tCtCGTGCGCCAGTGTACTCTGCT | SS | 104 |
| #Ga0181610_1 0916949_v1 | GTGCAGCACCTGTCTTTAGGTTCTTG | SS | 105 |
| #Ga0181610_1 0916949_v2 | CGTGGACGGTAGCCTATTTAGCATT | SS | 106 |
| #Ga0181610_1 0916949_v3 | ATGTTTTAGAGATTTGCTCCACCTCGC | SS | 107 |
| #Ga0181610_1 0937620_v1 | GCGGTATTGCATCTTTTTGTCCTT | SS | 108 |
| #Ga0181610_1 0937620_v2 | AGCCGTGCAGCACCTGTTTT | SS | 109 |
| #Ga0181610_1 0937620_v3 | tCCGAACTGAGAGAAGGTTTTGAGATTA GC | SS | 110 |
| #Ga0181610_1 0945623_v1 | ACGGCCGGCTTTTTGCGA | SS | 111 |
| #Ga0181610_1 0945623_v2 | GAGTTAAGCTCCAGGTTTTCACGC | SS | 112 |
| #Ga0181610_1 0945623_v3 | TACGGCCGGCTTTTTGCGATT | SS | 113 |
| #Ga0181610_1 0955219_v1 | TACATTTAGTTTTTCTCCCTGCACCATG | SS | 114 |
| #Ga0181610_1 0955219_v2 | GTACATTTAGTTTTTCTCCCTGCACCAT | SS | 115 |

TABLE 4-continued

Capture Polynucleotides for Hybridization to Amplicons Generated
from Environmental Samples.

| Description | Sequence | Sample Type | SEQ ID NO. |
|---|---|---|---|
| #Ga0181610_1 0955219_v3 | tCAAAGTTGAGCTTCGGCTTTTCAC | SS | 116 |
| #Ga0181610_1 097186_v1 | ACTGACAGAGTTTTACACCCCAAGGG | SS | 117 |
| #Ga0181610_1 097186_v2 | CGATCCGAACTGAGAATAGGTTTAAGA G | SS | 118 |
| #Ga0181610_1 097186_v3 | CAGCGTGCTGATCTGCGTTTACTAG | SS | 119 |
| #Ga0181610_1 100471_v1 | GCAACTCCCATTTTTGGGTTGGATG | SS | 120 |
| #Ga0181610_1 100471_v2 | TGAACTGAGGACGGTTTTATGGATTTGC | SS | 121 |
| #Ga0181610_1 101123_v1 | GAGCGTATGCGGTATTAGCGTAAGTTT | SS | 122 |
| #Ga0181610_1 101123_v2 | ACGGTATTAGCGCAACCCCTTT | SS | 123 |
| #Ga0181610_1 101123_v3 | GTTTGGCAACCCTTTGTACCGA | SS | 124 |
| #Ga0181610_1 108361_v1 | ATGTCAAGGGTAGGTAAGGTTTTTCG | SS | 125 |
| #Ga0181610_1 114317_v1 | GAACTACGAACAGCTTTTTGAGATTCG C | SS | 126 |
| #Ga0181610_1 114317_v2 | ATAATATCCGGTTTTAGCACTCCTTTCG | SS | 127 |
| #Ga0181610_1 114317_v3 | AAGCCCTCCTTTAGCACCTTAGTTTT | SS | 128 |
| #Ga0181610_1 116582_v1 | ATAGAGCTCGGCTTCATGCGGTATTAG | SS | 129 |
| #Ga0181610_1 116582_v2 | TATAGAGCTCGGCTTCATGCGGTATTAG | SS | 130 |
| #Ga0181610_1 116582_v3 | ATATCACTATAGAGCTCGGCTTCATGCG | SS | 131 |
| #Ga0181610_1 117382_v1 | GAACTGAGACGCACTTTTAGAGGTTGG | SS | 132 |
| #Ga0181610_1 117382_v2 | TGCAGCACCTTGTTTCAGGTCATTG | SS | 133 |
| #Ga0181610_1 117382_v3 | tCGCGTTTTCTTCCCAGATAAAAGCAGT TT | SS | 134 |
| Evi_Hyb1 | CatAAATTCCAtgTaCCcCatCGGc | Purified *E. vietnamensis* DNA | 135 |
| Evi_Hyb2 | CCGGAAACTTTCACCGCTGAC | Purified *E. vietnamensis* DNA | 136 |
| Phe_Hyb1 | tgTcAcATTCCgCCTaCCTCTAgtGTAt | Purified *P. heparinus* DNA | 137 |
| Phe_Hyb2 | cGTCAGTATCAAggGCAcTgCgata | Purified *P. heparinus* DNA | 138 |

TABLE 4-continued

Capture Polynucleotides for Hybridization to Amplicons Generated
from Environmental Samples.

| Description | Sequence | Sample Type | SEQ ID NO. |
|---|---|---|---|
| Mru_Hyb1 | CTcCGaccgTCTAGCcTca | Purified *M. ruber* DNA | 139 |
| Mru_hyb2 | TCGGTCTTTAGCATCGGACTTGAGAG | Purified *M. ruber* DNA | 140 |
| Eco_Hyb1 | GgAATTCtACCcCCCTCTACGagAC | Purified *E. coli* DNA | 141 |
| #Ga0181608_1 001153_v1 | GGGTATTATCCCCAGTTTTCCGGG | Oil (tar sands tailing pond, Alberta Canada) | 142 |
| #Ga0181608_1 0018514_v1 | GCCTTGGTGGGCTTTTACCCC | Oil | 143 |
| #Ga0181608_1 0024138_v1 | GAACTGAGAACGGTTTTTCCGATTAGC | Oil | 144 |
| #Ga0181608_1 0053911_v1 | ATTCGACAGGGGTTTACGATCCGAA | Oil | 145 |
| #Ga0181608_1 009102_v1 | CGGTATTAGCGGTCGTTTCCAACC | Oil | 146 |
| #Ga0181608_1 0091215_v1 | CGAAGGAACGGACTATCTCTAGTCTTTT | Oil | 147 |
| #Ga0181608_1 013222_v1 | GTTAAGCTGTGAGTTTTCACGAACAAC G | Oil | 148 |
| #Ga0181608_1 015781_v1 | GCCATGCAGCACCTTGTTTCATG | Oil | 149 |
| #Ga0181608_1 0192727_v1 | GCTACTTGTGGAATTCCATTTTCTCCGT | Oil | 150 |
| #Ga0181608_1 0241723_v1 | GGTACCGCCGCTTTTGAGAG | Oil | 151 |
| #Ga0181608_1 037542_v1 | GAACTGGGGCGCGCTTTTTG | Oil | 152 |
| #Ga0181608_1 062404_v1 | TGAGCCAGGATCAAACTCTCCAGTTTTT | Oil | 153 |
| #Ga0181608_1 073854_v1 | TTGCATGTCAAGCCTTGGTAAGGTTTTT | Oil | 154 |
| #Ga0181608_1 115897_v1 | GAACTGGCGCCTCTTTTAAGGATTTG | Oil | 155 |
| #Ga0181608_1 119449_v1 | GGCTTCGGCACCGATAGGTTTT | Oil | 156 |
| #Ga0181608_1 140976_v1 | TGAGGACGGCTTTTTGGGATTGG | Oil | 157 |
| #Ga0181608_1 160854_v1 | TGAGACTGGTTTTTTGAGATTAGCTTGG | Oil | 158 |

Figure 2A:
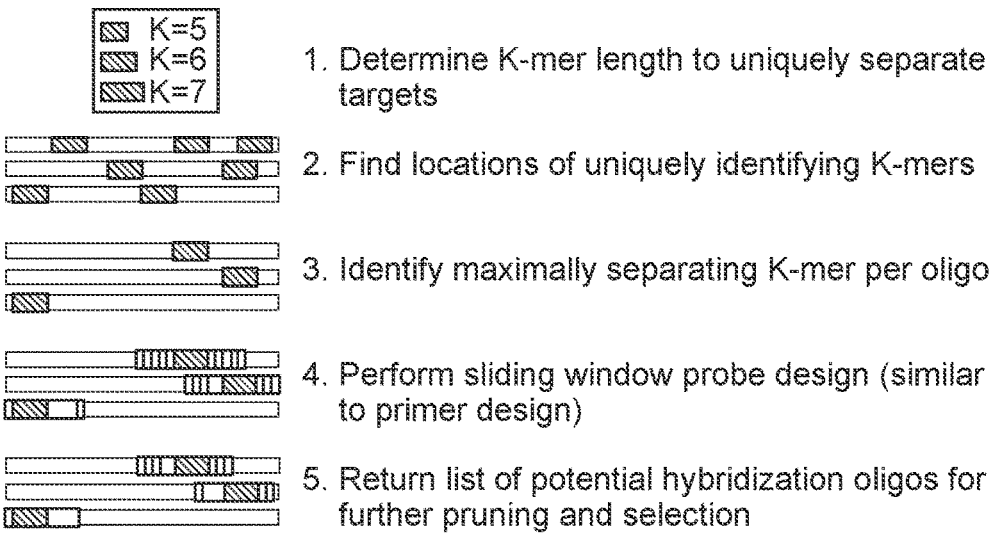
FIG. 2A shows algorithmic steps used for the design of capture polynucleotides.

Predetermined sequences in capture oligonucleotides can be selected by manual inspection of genetic data for bacteria of interest, or with the assistance of algorithmic tools. Algorithms for selected sequences to discriminate between two or more species of bacteria may include one or more steps of: (1) determining K-mer length (e.g., a 5-, 6-, or 7-base length) to uniquely distinguish targets; (2) finding locations of uniquely identifying K-mers; (3) identifying maximally separated K-mers; (4) performing sliding window probe design (similar to primer design); and (5) re-running candidate sequences for further pruning and selection. A graphical representation of an exemplary algorithmic processes is depicted in FIG. 2A. Identifying sequences can be selected in this manner for detection of pathogens associated with hospital-acquired infections, including but not limited the pathogens listed in Table 2, Table 3, and Table 6 as well as for the detection of microbes relevant to the safety and/or quality of water, soil, foods, agricultural products, and natural resources, including but not limited to those listed in Table 4.

The assay according to the present disclosure can also be used for gram typing of bacteria. In one embodiment, the V6 variable region may be used for the detection of Gram positive or negative bacteria. Exemplary sequences that can be used in such embodiments are described, for example, in Yang, S., et al. "Rapid PCR-Based Diagnosis of Septic Arthritis by Early Gram-Type Classification and Pathogen Identification" J CLIN MICROBIOL, April 2008, Vol 47(4), p. 1386-1390. A non-limiting example of a sequence that can be used as a capture polynucleotide for identifying Gram positive organisms includes: AGGTGGTG-CATGGTTGTCGTCAGC (SEQ ID NO: 173). A non-limiting example of a sequence that can be used as a capture polynucleotide for identifying Gram negative organisms includes: ACAGGTGCTGCATGGCTGTCGTCAGCT (SEQ ID NO: 174). In one aspect, these probes are modified at the 5' end to have an amine (and spacer) for conjugation reactions. Exemplary V6 primers suited for use in such embodiments are described in Table 1.

In addition to determining the species and/or strain of microbes present in a particular sample, the methods of the present disclosure can also be used for identifying further characteristics relevant to pathogenicity and/or virulence, e.g., the presence of antibiotic-resistance bacteria. Many strains of methicillin-resistant *S. aureus* (MRS), for example, are known to possess the mecA gene located in a staphylococcal cassette chromosome mec (SCCmec). See, e.g., Song, et al. (*FEBS Lett.* 1987, 221(1): 167-171); Baba et al. (The Lancet, 2002, 359:1819-1827). MRSA strains can be identified by using microbeads that contain a capture polynucleotide having a sequence or sequences present in mecA and/or SCCmec. In some embodiments, at least one of the microbe identifying sequences in the amplicons comprises an antibiotic resistance gene sequence. Capture polynucleotides employed in the present disclosure can contain identifying sequences present in a variety of acquired antibiotic resistance genes including, but not limited to, aminoglycoside resistance genes, quinolone resistance genes, and tetracycline resistance genes. Examples of such acquired antibiotic resistance genes are described, e.g., by van Hoek (*Front. Microbiol.* 2011, 2: 203) and Bockelmann (*Applied and Environmental Microbiology* 2008, 75: 154-63), and sequences from such genes can be used in capture polynucleotides on microbeads of the present disclosure. This can include directly targeting extended-spectrum beta-lactamase genes, such as TEM-1. For example, in *Staphylococcus aureus* ("Sau"), primers and hybridization oligonucleotides may be designed to target fragments of mecA (encoding methicillin resistance), aacA-aphD (aminoglycoside resistance), tetK, tetM(tetracycline resistance), erm(A), erm(C) (macrolide-lincosamide-streptogramin B resistance), vat(A), vat(B), and vat(C) (streptogramin A resistance). A non-limiting example of a primer and hybridization set for mecA is:

```
forward primer:
                              (SEQ ID NO: 161)
CATTGATCGCAACGTTCAATTTAAT;

reverse primer:
                              (SEQ ID NO: 162)
TGGTCTTTCTGCATTCCTGGA;
and hybridization oligonucleotide:
                              (SEQ ID NO: 163)
CTATGATCCCAATCTAACTTCCACATACC.
```

Methods of the present disclosure may also be applied to detect viruses. In some embodiments, the virus is influenza A virus including subtype H1N1, influenza B virus, influenza C virus, rotavirus A, rotavirus B, rotavirus C, rotavirus D, rotavirus E, SARS coronavirus, including SARS-CoV-1 and SARS-CoV-2, human adenovirus types (HAdV-1 to 55), human papillomavirus (HPV) Types 16, 18, 31, 33, 35, 39, 45, 51, 52, 56, 58, 59, parvovirus B19, molluscum contagiosum virus, JC virus (JCV), BK virus, Merkel cell polyomavirus, coxsackie A virus, norovirus, Rubella virus, lymphocytic choriomeningitis virus (LCMV), yellow fever virus, measles virus, mumps virus, respiratory syncytial virus, rinderpest virus, California encephalitis virus, hantavirus, rabies virus, ebola virus, dengue virus (DENV), zika virus (ZIKV), marburg virus, herpes simplex virus-1 (HSV-1), herpes simplex virus-2 (HSV-2), varicella zoster virus (VZV), Epstein-Barr virus (EBV), cytomegalovirus (CMV), herpes lymphotropic virus, roseolovirus, Kaposi's sarcomaassociated herpesvirus, hepatitis A (HAV), hepatitis B (HBV), hepatitis C (HCV), hepatitis D (HDV), hepatitis E (HEV), human immunodeficiency virus (HIV), Human Tlymphotropic virus Type I (HTLV-1), Friend spleen focus-forming virus (SFFV) or Xenotropic MuLV-Related Virus (XMRV).

For example, methods of the present disclosure can be used to detect the SARS-CoV-2 virus. Exemplary primer and capture polynucleotide sequences for use in such embodiments can be obtained from the United States Department of Health and Human Services Centers for Disease Control and Prevention. In one aspect, suitable sequences are modified at the 5' end with an amino-terminated 12-carbon spacer (the "5AmMC12" modification) and an oligo(T) spacer for use in the assay according to the present disclosure.

In one embodiment, the method of the present disclosure utilizes all of these capture polynucleotide in parallel using beads of different spectral codes to target the different viral sequences. In another embodiment, these capture polynucleotide are combined with capture polynucleotides targeting other viruses, such as the SARS-CoV-1, influenza A, influenza B, dengue virus or zika virus. For example, a flu panel may include capture polynucleotides for targeting influenza A, influenza B, SARS-CoV-1, and SARS-CoV-2.

In another embodiment, a panel could include viral and bacterial capture polynucleotides to simultaneously test for viruses and bacterial co-infections. For example, the panel may include capture polynucleotides for influenza A, influenza B, SARS-CoV-1, and SARS-CoV-2 and capture polynucleotides for bacterial species, such as the bacterial capture polynucleotides described above.

Similarly, it is possible to extend the method to the analysis of host response genes, such as a procalcitonin gene, a c-reactive protein gene, a tumor necrosis factor alpha gene, or an interleukin gene. Amplicons may be prepared using mRNA from cells, or cell-free RNA. In some such embodiments, reverse transcription may be performed followed by PCR or quantitative PCR (e.g., RT-qPCR). The PCR product can then be hybridized to the beads, optionally after a treatment step with lambda exconuclease. This may be done in parallel with PCR for amplification of 16S variable regions and detection of pathogens. A non-limiting example of a primer and hybridization set for procalcitonin is:

```
forward primer:
                                    (SEQ ID NO: 166)
5'-TCTAAGCGGTGCGGTAATCT-3';

reverse primer:
                                    (SEQ ID NO: 167)
5'-TTCTTTCCAGGTGCTCCAAC-3';
and hybridization probe:
                                    (SEQ ID NO: 168)
5'-TGGGCACATACACGCAGGA-3'.
```

Methods of the present disclosure may also be applied to multiplexed detection of fungal species in the case of fungal infections. Fungal species may be targeted in parallel with bacterial and/or host-response genes. Analogous to targeting the conserved regions of the 16S ribosomal subunit for PCR followed by specific and multiplexed hybridization to capture polynucleotides with sequences that target the inter-spaced hypervariable regions (e.g., V1, V6), the conserved and variable regions of the 18S ribosomal subunit gene can be targeted to identify different fungal species. Alternatively, the inter-transcribed spacer may be targeted for species identification. For example, fungal species of interest include *Fusarium* sp., *Cladosporium* sp., *Aspergillus flavus, Aspergillus fumigatus, Candida albicans, Trichosporon asahii,* and *Glomerella* cingulate. A non-limiting example of a primer and hybridization set for targeting the 18S ribosomal subunit gene with detection of *Aspergillus fumigatus* and *Candida albicans* is:

```
forward primer:
                                    (SEQ ID NO: 169)
TTGGTGGAGTGATTTGTCTGCT;

reverse primer:
                                    (SEQ ID NO: 170)
TCTAAGGGCATCACAGACCTG;

hybridization probe (A. fumigatus):
                                    (SEQ ID NO: 171)
TCGGCCCTTAAATAGCCCGGTCCGC;

hybridization probe (C. albicans):
                                    (SEQ ID NO: 172)
TTAACCTACTAAATAGTGCTGCTAGC.
```

Capture polynucleotides may contain spacer units between the sequence used for hybridization to amplicons and the functional group used for conjugation to the micro-beads. Spacer units may contain, for example, hexaethylene glycol, triethylene glycol, alkylene moieties (e.g., dodecane-1,12-diyl, hexane-1,6-diyl), photo-cleavable spacers, reducible spacers, and other linking groups known in the art. See, e.g., Hermanson, *Bioconjugate Techniques* (3rd *Ed.*), Academic Press, 2013. Spacer units may also contain nucleotides such as oligo(T) sequences e.g., TTTTTTT (SEQ ID NO:159). In some embodiments, the capture polynucleotides contain a 5'-amine group for conjugation to microbeads, as well as an optional spacer moiety linking the 5'-amine group to the amplicon hybridization sequence. As used herein the designation "5AmMC12" refers to a 5'-amine group having the formula $NH_2(CH_2)_{12}$—, which is bonded to the 5'-phosphate group of the capture polynucleotide. In some embodiments, the spacer unit is /5AmMC12/TTTTTTT (SEQ ID NO:160).

B. Preparation of Microbeads

Microbeads of the present disclosure may include different types of lanthanide nanoparticles. As set forth above, the nanoparticles have at least one dimension (e.g., length, width, or circumference) ranging from 1 to 1,000 nm. A microbead may include one or more different lanthanide nanoparticles, e.g., 2 or more, 3 or more, 4 or more, 5 or more, 6 or more, 7 or more, 8 or more, 9 or more, or 10 or more, wherein each lanthanide nanoparticle has a different luminescence emission spectrum upon excitation. For example, in some embodiments, the microbeads disclosed herein may include from 1 to 10, from 2 to 10, from 3 to 10, from 4 to 10, from 5 to 10, from 6 to 10, from 7 to 10, from 8 to 10, or from 9 to 10 types of lanthanide nanoparticles, wherein each lanthanide nanoparticle has a different luminescence emission spectrum upon excitation. Signals from the combined luminescence spectra make up the spectral signature of a particular microbead, and are mapped to a unique spectral signature 'code' during code deconvolution.

Microbeads used in the methods described herein typically have capture polynucleotides immobilized to polymers in the microbead. In general, the capture polynucleotides are designed to contain predetermined sequences such that at least some of the capture polynucleotides comprise a sequence substantially complementary to a microbe-identifying sequence of one or more amplicons. Beads sets used in the methods generally contain many different predetermined sequences, although each copy of the capture polynucleotide on any one microbead will generally have the same predetermined sequence. In some embodiments, the plurality of microbeads comprises at least 5 (e.g., at least 10, 15, 20, 25, 30, 35, 40, 45, or 50) different spectral signatures and immobilized capture polynucleotides comprising at least 5 (e.g., at least 10, 15, 20, 25, 30, 35, 40, 45, or 50) different predetermined sequences. In some embodiments, the plurality of microbeads comprises at least 20 (e.g., 20-25) different spectral signatures and immobilized capture polynucleotides comprising at least 20 (e.g., 20-25) different predetermined sequences. In some embodiments, the plurality of microbeads comprises at least 40 (e.g., 40-50) different spectral signatures and immobilized capture polynucleotides comprising at least 40 (e.g., 40-50) different predetermined sequences. In some embodiments, the plurality of microbeads comprises 24 different spectral signatures and immobilized capture polynucleotides comprising 24 different predetermined sequences. In some embodiments, the plurality of microbeads comprises 48 different spectral signatures and immobilized capture polynucleotides comprising 48 different predetermined sequences.

Microbeads according to the present disclosure may contain as few as two different predetermined sequences or as many as tens of thousands of predetermined sequences depending, in part, on the complexity of the samples intended for study. Accordingly, combining amplicons generated from the sample with the microbeads may include hybridizing amplicons to at least 1, 5, 10, 25, 50, 75, 100, 500, 1,000, 5,000, 10,000, or more microbeads having different spectral signatures and different capture polynucleotides. In some embodiments, the combining in step (ii) comprises hybridizing amplicons to at least 50 microbeads (or 50 different populations of microbeads) having different spectral signatures and different capture polynucleotides. In some embodiments, the magnitude of signal detected from an individual microbead in step (iv) corresponds to the amount of the amplicons captured on the microbead.

Lanthanide spectral signatures employed in the methods of the presence disclosure include emitted light in the range of 350-850 nm (e.g., 400-800 nm), exhibiting one or more peaks associated with lanthanide luminescence. Lanthanide nanoparticle spectra are typically characterized by narrow emission bands (also referred to as "signals") in the visible region, making one species of material easily distinguishable from another. A "specific" lanthanide spectral signature in a microbead or other material can therefore be designed based on the particular identity and relative amounts of lanthanides in the microbead. In some embodiments, each of the lanthanide spectral signatures comprises an Eu signal, a Dy signal, an Sm signal, a Ce signal, a Tb signal, a La signal, a Pr signal, an Nd signal, a Gd signal, an Ho signal, an Er signal, a Tm signal, a Yb signal, a Pm signal, an Lu signal, or a combination thereof. The microbeads of the present disclosure generally include one or more different lanthanide nanoparticles as discussed herein and one or more polymers, copolymers, or combinations thereof. In some embodiments, each microbead further comprises a crosslinked polymer, wherein the capture polynucleotides are covalently bonded to the crosslinked polymer. In some embodiments, the crosslinked polymer is a hydrogel-forming polymer (e.g., poly(ethylene glycol)) which can evenly and irreversibly entrap the lanthanide nanoparticle materials within the microbead. The lanthanide nanoparticles themselves may be coated with a polymer such as poly(acrylic acid) as described in more detail below.

In some embodiments, the nanoparticles include a lanthanide and a host lattice. Lanthanides which may be incorporated into the lanthanide nanoparticles include, for example, Ce, Pr, Nd, Sm, Eu, Gd, Tb, Dy, Ho, Er, Tm, Yb, La, combinations thereof, compounds containing Ce, Pr, Nd, Sm, Eu, Gd, Tb, Dy, Ho, Er, Tm, Yb, La and combinations thereof, and ions of Ce, Pr, Nd, Sm, Eu, Gd, Tb, Dy, Ho, Er, Tm, Yb, La and combinations thereof. Host lattices employed in the nanoparticles generally contain constituent atoms packed in a regularly ordered, repeating pattern which can accommodate the incorporate of lanthanide atoms or ions. The lattice can be crystalline, which a structure that is, e.g., triclinic, monoclinic, orthorhombic, tetragonal, trigonal, hexagonal, or cubic. A crystalline lattice may contain one or more regions, i.e., grains, with distinct crystal boundaries. The crystalline lattice may, in some instances, contain two or more crystal geometries. A number of suitable host lattices can be utilized in the lanthanide nanoparticles. For example, lanthanide dopants may be incorporated into a host lattice to provide lanthanide-doped yttrium orthovanadate ($YVO_4$), lanthanide-doped oxides (e.g., doped $ZrO_2$, doped $TiO_2$, doped $BaTiO_3$), lanthanide-doped halides (e.g., doped $LaF_3$), lanthanide-doped phosphates (e.g., dope $LaPO_4$, doped $LuPO_4$, or doped $YbPO_4$), and lanthanide-doped strontium borates (e.g., $SrB_4O_7$, $SrB_6O_{10}$, and $Sr_4B_{14}O_{25}$), among others.

Lanthanide nanoparticles according to the present disclosure may be prepared using methods such as those described by Xu et al. (*Solid State Communications*, 2004. 130:465-468), Choi et al. (*Journal of Luminescence*. 2010. 130:549-553), Wang et al. (*Angewandte Chemie International Edition*, 2008. 47:906-909), and Nguyen, et al. (2017) *Advanced Optical Materials*, 5(3): 1600548, the disclosures of which are incorporated by reference herein in their entirety. As a non-limiting example, one volume of aqueous lanthanide dopant solution (e.g., $Sm(NO_3)_3$, $Dy(NO_3)_3$, $Eu(NO_3)_3$; 0.1 M), can be combined with 10-20 volumes of an yttrium salt solution (e.g., $Y(NO_3)_3$, 0.1 M) and added portion-wise to an 10-100 additional volumes of osmogent solution (e.g., ~2000 kDa PEG, 10% w/w), optionally containing a bismuth salt such as $Bi(NO_3)_3$. A solution of matrix material (e.g., 10-100 volumes of $Na_3VO_4$, 0.1 M) is added portion-wise prior to microwave heating (e.g., 180° C.) for 5-120 min. Following heating, the resulting white material can be washed and resuspended (e.g., in water with optional polyacrylic acid (1000-2000 kDa; 1-10% v/v)), with our without sonication and/or filtering (e.g., through 0.45-μm PTFE filters) filters to obtain the final nanoparticles, 25-250 nm in size (e.g., 30-160 nm), as milky white solutions with concentrations ranging from about 5 mg/mL to about 500 mg/mL.

Lanthanide nanoparticles according to the present disclosure may be up-converting or down-converting lanthanide nanoparticles. Suitable up-converting lanthanide nanoparticles may include, for example, $NaGdF_4$:Tm; $NaGdF_4$:Ln; $NaGdF_4$Yb; $NaGdF_4$Er; $NaGdF_4$Yb, Er; $NaYF_4$:Er; $NaYF_4$:Yb; $NaYF_4$:Er,Yb; $NaYF_4$:Tm,Yb; $LaF_3$:Yb,Tm; $LaF_3$:Yb, Er; and $LaF_3$:Yb,Ho nanoparticles. Suitable down-converting lanthanide nanoparticles may include, for example, $YVO_4$:Eu; $YVO_4$:Dy; and $YVO_4$:Sm nanoparticles. It should be noted that the above referenced lanthanides may be incorporated into the nanoparticles as their respective ions. Materials may be added during preparation of the lanthanide nanoparticles to increase their UV absorption, for downconverters, or IR absorption, for upconverters. For example, in some embodiments bismuth is incorporated into the lanthanide nanoparticles to increase their UV absorption.

In some embodiments, lanthanide nanoparticles as disclosed herein may be modified (e.g., covered or coated) in a suitable material to facilitate formation of a stable colloid suspension of the lanthanide nanoparticles in a carrier fluid. Suitable materials may include materials which prevent aggregation of the lanthanide nanoparticles in the carrier fluid (e.g., $H_2O$) and/or facilitate maintenance of a nanoparticle form of the lanthanide nanoparticles. For example, suitable materials which may be used to cover or coat the lanthanide nanoparticles may include polyethyleneimine (PEI), polyacrylic acid (PAA), sodium citrate, or citric acid. Polyethyleneimine (PEI) may be suitable for use, e.g., as a coating material in order to make the nanophosphors more compatible with a monomer mixture. In some embodiments, the nanoparticles are coated with PAA. Advantageously, PAA can enhance the photostability of the nanophosphors in addition to facilitating stable colloid formation.

Accordingly, some embodiments of the present disclosure provide a plurality of microbeads wherein each of the microbeads comprises a plurality of lanthanide nanoparticles. In some embodiments, the lanthanide nanoparticle comprises a lanthanide-doped host lattice. In some embodiments, the host lattice is yttrium orthovanadate, lanthanum phosphate, or a combination thereof.

The microbeads of the present disclosure can contain a variety of polymers. In some embodiments, the polymers form microbeads upon polymerization via, for example, a thermal- or photo-initiated polymerization process. Such polymers include, but are not limited to, polyacrylates, polyacrylamides, polymethacrylates, polymethacrylamides, polystyrenes, polythiol-enes, polyurethanes, epoxy resins, polysaccharides (such as agarose), as well as copolymers (e.g., random copolymers or block copolymers) or combinations of two or more of the above. Suitable polymers also include polysiloxanes, polyethers (e.g., polyethylene glycol (PEG)), polyvinylpyrrolidones, vinyl ethers, vinyl acetates, polyimides, polysulfones, polyamic acids, polyamides, polycarbonates, polyesters, and copolymers or combinations of two or more of the above. The polymers may be provided in monomer form during the microbead preparation process, and these monomers may be polymerized to form the above polymers, copolymers or combinations thereof in the spectrally encoded microbeads of the present disclosure. Suitable monomers may include those which can be polymerized in situ alone or with a cross-linking agent to form a cross-linked resin.

In some embodiments, polyacrylate or polyacrylamide microbeads can be prepared using monomers which contain functionalized PEGs. The functionalized PEG can contain a polymerizable functional group on each end of the PEG chain, e.g., a PEG-diacrylate or a PEG-diacrylamide for formation of crosslinked polymers that contact the lanthanide nanoparticles (e.g., a crosslinked PEG that contacts PAA-coated lanthanide nanoparticles). Alternatively, the functionalized PEG can contain a polymerizable functional group on one end of the PEG chain and an orthogonal reactive moiety on the other end of the PEG chain. The orthogonal reactive moiety can be used for the attachment of oligonucleotides or other elements (e.g., dyes, labels, or the like). Examples of orthogonal reactive moieties include, but are not limited to, amines, carboxylates, thiols, activated esters (e.g., N-hydroxysuccinimidyl (NHS) esters, sulfo-NHS esters, and pentafluorophenyl (PFP) esters); carbodiimides; maleimides; halogenated acetamides; hydroxymethyl phosphines; aryl azides; imidoesters; isocyanates; vinyl sulfones; pyridyl disulfides; benzophenones; azides; alkynes (including linear alkynes and cycloalkynes); and tetrazines.

In some embodiments, a suitable monomer for use in preparation of the microbeads is selected from a PEG diacrylamide (PEG-DAM), a PEG monoacrylamide-monoamine (PEG-AM) and a PEG-monoacrylamide-monoBoc. Such monomers can contain any suitable branched or linear PEG. In some embodiments, the PEG is a linear polymer having a weight average molecular weight ranging from 500 g/mol to about 10,000 g/mol (e.g., about 700 g/mol, about 2000 g/mol, or about 5,000 g/mol). If necessary, number average and weight average molecular weight values can be determined by gel permeation chromatography (GPC) using polymeric standards (e.g., polystyrene or like material).

Additional monomers which may be utilized in the microbeads may include, e.g., monomers which are capable of participating in thiol-ene thiol-yne reactions, e.g., pentaerythritol tetrakis(3-mercaptopropionate) (TT); diallyl phthalate (DAP); 1,3,5-triallyl-1,3,5-triazine-2,4,6(1H,3H,5H)-trione (TTT); 1,7-octadiyne (OY); mercaptoacetic acid (MA); allylamine (AA), pentaerythritol triallyl ether (PTE) and propargylamine (PA). These monomers find use, for example, in photo-initiated polymerization processes. For additional discussion of thiol-ene thiol-yne reactions and monomers suitable for use therein, see, e.g., Prasath et al. (*Polym. Chem.,* 2010 1: 685-692), the disclosure of which is incorporated by reference herein.

The microbeads can be prepared using microfluidic devices as described, for example, in U.S. Pat. No. 10,241,045, U.S. Pat. Appl. Pub. No. 2015/0192518, and Nguyen, et al. (*Adv Opt Mater.* 2017, 5, 1600548), which are incorporated herein by reference in their entirety. Preparation of the microbeads may include, for example: (i) mixing at least two fluids into a first solution, wherein each fluid comprises a polymerizable component (e.g., a polymer or monomer), a polymerization initiator, and a different lanthanide nanoparticle; (ii) forming droplets from the solution; and (iii) subjecting the droplets to polymerization conditions, thereby producing a set of polymeric microbeads embedded with at least two different lanthanide nanoparticles. In some embodiments, the relative concentrations of the lanthanide nanoparticles are substantially equal (i.e., not significantly different) among the polymeric microbeads in the set. Additional sets of microbeads can be prepared by mixing the fluids into additional solutions, wherein the concentration of at least one of the lanthanide nanoparticles in the addition solutions is different than the concentrations of the nanoparticles in (i) above, and conducting the droplet-forming steps and polymerization steps as set forth above.

The lanthanide nanoparticle contained in each fluid may be present at a concentration of from about 1 mg/mL to about 250 mg/mL, e.g., from about 5 mg/mL to about 250 mg/mL, from about 10 mg/mL to about 250 mg/mL, from about 20 mg/mL to about 250 mg/mL, from about 30 mg/mL to about 250 mg/mL, from about 40 mg/mL to about 250 mg/mL, from about 50 mg/mL to about 250 mg/mL, from about 60 mg/mL to about 250 mg/mL, from about 70 mg/mL to about 250 mg/mL, from about 80 mg/mL to about 250 mg/mL, from about 90 mg/mL to about 250 mg/mL, from about 100 mg/mL to about 250 mg/mL, from about 150 mg/mL to about 250 mg/mL, or from about 200 mg/mL to about 250 mg/mL.

Where a polymerization method is utilized to form the spectrally encoded polymeric microbeads, a suitable polymerization initiator (e.g., a photoinitiator or thermal initiator) may be utilized which is compatible with the polymerizable components and the polymerization conditions. For example, where a UV polymerization process is utilized, a suitable initiator may include a compound that, when exposed to UV light, undergoes a photoreaction, producing reactive species that are capable of initiating polymerization. Exemplary photoinitiators may include, e.g., acetophenones, benzyl and benzoin compounds, benzophenone, cationic photoinitiators, and thioxanthones. In some embodiments, a photoinitiator such as 2-hydroxy-4'-(2-hydroxyethoxy)-2-methylpropiophenone (Irgacure® 2959) or lithium phenyl-2,4,6-trimethylbenzoylphosphinate (LAP) is utilized. Suitable thermal initiators may include, for example, azo compounds, peroxides or hydroperoxides, persulfates, and the like.

The step of forming droplets from the solution may include, for example, contacting a hydrophilic solution containing the polymerizable component with a hydrophobic solvent (e.g., mineral oil or water-immiscible organic solvent, e.g., octanol) such that droplets are formed. Alternatively, a hydrophobic solvent (e.g., mineral oil or water-immiscible organic solvent, e.g., octanol) can be used to form the solution containing the polymerizable component, and droplets can be formed by contacting the solution with a hydrophilic carrier fluid (e.g., water). These steps may be accomplished, for example, by introducing the solution containing the polymerizable component into a flowing stream of the carrier fluid. Any suitable device and/or method for droplet formation may be utilized to form droplets in the context of the present disclosure, including, e.g., the utilization of flow focusing nozzles. See, e.g., Ward et al. (*Electrophoresis,* 2005, 26:3716-3724), the disclosure of which is incorporated by reference herein. The droplet size may be modulated by adjusting the pressure used to form the droplet, e.g., at the interface of the solution and the hydrophobic carrier fluid. In addition, droplet size may be modulated by adjusting the geometry, e.g., size and shape, of the microfluidic device channels. One or more stabilizers or surfactants may be added to one or more of the fluids to prevent droplet merging and sticking of droplets to the walls of the microfluidic device. Suitable surfactants may include, for example, Abil® EM90 (a silicon based emulsifier; CAS No. 144243-53-8) and Span™ 80 (CAS No. 1338-43-8), among others.

In some embodiments, monomer input solutions for microbead synthesis contain purified water, monomer (e.g., 700 MW PEG-diacrylate, 40-60% w/w), initiator (e.g., photoinitiator Irgacure® 2959, 1-10% w/w), Sigma-Aldrich), and lanthanide nanoparticles at various concentrations. Droplets can be formed by introducing the input solutions in a continuous flowing stream of hydrophobic fluid (e.g., light mineral oil), with or without surfactants to reduce or eliminate merging of droplets (e.g., Abil® EM90 (Evonik Industries, Germany), Span™ 80 (Sigma-Aldrich), 0.05%-5% w/w).

The step of subjecting the droplets to polymerization conditions may include, for example, exposing the droplets to UV radiation or elevated temperatures to initiate polymerization. Other known polymerization methodology can be employed, provided that it is compatible with the polymers and/or monomer components to be polymerized. Examples of such methodology include, but are not limited to, thiol-ene polymerization, redox-initiated polymerization, and controlled radical polymerization processes such as reversible addition-fragmentation chain transfer (RAFT) polymerization, atom transfer radical polymerization (ATRP), and nitroxide-mediated polymerization (NMP). See also, e.g., Piskin et al. (*J. of Biomaterials Science Polymer Edition* 1994, 5: 451-471), the disclosure of which is incorporated by reference herein.

In some embodiments, droplets are exposed to radiation (e.g., UV radiation) by localizing the radiation exposure onto a microfluidic device such that the droplets are only irradiated after they have been formed on the microfluidic device and before they exit the microfluidic device. Radiation localization may be achieved using an inverted microscope by mounting the microfluidic device on the microscope stage. For example, UV illumination may occur through the objective onto a very small area and an additional aperture within the microscope UV light path may further restrict the UV irradiation to a specific area of the microfluidic device. Alternatively, UV illumination may occur after the droplets exit the microfluidic device.

Methods which do not require polymerization may also be used to form the spectrally encoded polymeric microbeads. For example, a polymer precipitation method may be utilized in which a pre-formed polymer (e.g., a mid- to high-molecular weight polymer) is dissolved in a suitable solvent (e.g., water) along with dispersed lanthanide nanoparticles. Droplets of this solution can be formed by introducing the solution into an immiscible carrier fluid (e.g., a hydrophobic carrier fluid, e.g., mineral oil). The immiscible carrier fluid and polymer should be selected such that the polymer does not dissolve in the immiscible carrier fluid, and the immiscible carrier fluid is capable of accepting the solvent leaching from the droplet as the polymeric microbead is formed through precipitation. Additional solvent-immiscible carrier fluid combinations may include, e.g., dichloromethane as a solvent and poly(vinyl alcohol) (PVA) as an immiscible carrier fluid. Microbead preparation methods utilizing a dichloromethane-poly(vinyl alcohol) (PVA) combination are described, for example, in Berkland et al. (*Journal of Controlled Release,* 2002, 73:59-74; *Journal of Controlled Release,* 2004, 94:129-141), the disclosures of which are incorporated by reference herein.

The steps of mixing at least two fluids can occur either before or after droplet formation depending on the particular microfluidic device architecture utilized. For example, where a herringbone type mixing architecture is utilized the two fluids may be mixed prior to droplet formation. Alternatively, where a zig-zag type mixing architecture is utilized droplets containing unmixed lanthanide nanoparticles may be formed and subsequently mixed to distribute the lanthanide nanoparticles within a droplet. Accurate programming of spectral codes for the spectrally encoded microbeads may be facilitated by precisely controlling the flow from each of the lanthanide nanoparticle fluid inputs as previously described, for example, in U.S. Pat. No. 10,241,045.

C. Functionalization of Microbeads

In some embodiments, microbeads are functionalized with reactive groups for conjugation of capture polynucleotides. Typically, a population of microbeads having the same spectral signature (e.g., a population ranging up to thousands of beads) is carried through one or more functionalization steps such that (i) each microbead in the population having the same spectral signature is conjugated to capture polynucleotides having the same sequence, and (ii) the number of capture polynucleotides conjugated to each microbead in the population is substantially the same. This process can be conducted, for example, with a microfluidic device having an in-line fraction collector for pooling of microbead populations by spectral signature. Sub-populations may be reserved for use in different chemical steps or for use in characterizing microbial populations. In some embodiments, for example, sub-populations of microbeads containing different spectral signatures may be combined such that a plurality of around 1,000 microbeads is used for combination with amplicons and each spectral signature is represented 50-100 times in the plurality.

In some embodiments, microbeads are functionalized with reactive groups that can then be conjugated to capture polynucleotides via one or more click reactions. As used herein, "click reaction" refers to a chemical reaction characterized by a large thermodynamic driving force that usually results in irreversible covalent bond formation. Examples of click reactions include thiol-ene reactions, such as the Michael addition of a thiol to a maleimide or other unsaturated acceptor; [3+2]cycloadditions, such as the Huisgen 1,3-dipolar cycloaddition reaction of an azide and an alkyne; [4+1]cycloaddition reactions between an isonitrile and a tetrazine; the Staudinger ligation between an azide and an ester-functionalized phosphine or an alkanethiol-functionalized phosphine; Diels-Alder reactions (e.g., between a furan and a maleimide); and inverse electron demand Diels-Alder reactions (e.g., between a tetrazine and a dienophile such as a strained transcyclooctene).

In some embodiments, the microbeads contain carboxylate groups for bonding to amine-functionalized capture polynucleotides. For example, acrylate groups in microbeads can be coupled to a thiol-functionalized carboxylic acid (e.g., 3-mercaptopropionic acid) in the presence of a base such as pyridine, N,N-diisopropylamine (DIPEA), or 1,8-diazabicyclo[5.4.0]-undec-7-ene (DBU). The carboxylates can then be reacted with amine-functionalized oligonucleotides using one or more coupling reagents such as a carbodiimide (e.g., N,N'-dicyclohexylcarbodiimide (DCC), 1-ethyl-3-(3-dimethylaminopropyl)-carbodiimide (EDC), a phosphonium salt (HOBt, PyBOP, HOAt, etc.), an aminium/uronium salt, a pyridinium coupling reagent (e.g., Mukaiyama's reagent, pyridinium tetrafluoroborate coupling reagents, etc.), a polymer-supported reagent (e.g., polymer-bound carbodiimide, polymer-bound TBTU, polymer-bound 2,4,6-trichloro-1,3,5-triazine, polymer-bound HOBt, polymer-bound HOSu, polymer-bound IIDQ, polymer-bound EEDQ, etc.), or the like (see, e.g., El-Faham, et al. *Chem. Rev.,* 2011, 111(11): 6557-6602; Han, et al. *Tetrahedron,* 2004, 60:2447-2467).

In some embodiments, the capture oligonucleotide includes a clickable moiety for reaction with a complementary clickable moiety on a microbead. As used herein, a "clickable moiety" refers to a functional group that is capable of forming a covalent bond via a click reaction, such as an azide, an alkyne, a phosphine, a thiol, a maleimide, an isonitrile, or a tetrazine. In some embodiments, each clickable moiety is independently selected from the group consisting of an azide, an alkyne, and a phosphine. In some embodiments, the microbeads contain an alkyne moiety for bonding to azide-functionalized capture polynucleotides. For example, the amine groups in microbeads formed using PEG monoacrylamide-monoamine (PEG-AM) can be coupled to a carboxylate-functionalized alkyne (e.g., 4-pentynoic acid) using a carbodiimide reagent such as 1-ethyl-3-(3-dimethylaminopropyl)carbodiimide hydrochloride (EDC). The alkynes can then be reacted with azide-functionalized oligonucleotides using a suitable catalyst (e.g., a copper salt such as copper (II) acetate, copper (II) sulfate, copper (I) bromide, or copper (I) iodide) and optional reducing agents (e.g., sodium ascorbate) and ligands (e.g., tris[(1-benzyl-1H-1,2,3-triazol-4-yl)methyl]amine (TBTA), tris(2-benzimidazolylmethyl)amine, tris(3-hydroxypropyl-triazolylmethyl)amine, or the like.

In some embodiments, a crosslinking reagent is used for attachment of the capture polynucleotides to the microbeads. The crosslinking reagents can react to form covalent bonds with functional groups in the capture oligonucleotides and on the microbead surfaces (e.g., a primary amine, a thiol, a carboxylate, a hydroxyl group, or the like). Crosslinkers useful for attaching capture oligonucleotides to microbeads include homobifunctional crosslinkers, which react with the same functional group in the oligonucleotide and the bead, as well as heterobifunctional crosslinkers, which react with functional groups in the bead and the oligonucleotide wherein the functional groups differ from each other.

Examples of homobifunctional crosslinkers include, but are not limited to, amine-reactive homobifunctional cross-linkers (e.g., dimethyl adipimidate, dimethyl suberimidate, dimethyl pimilimidate, disuccinimidyl glutarate, disuccinimidyl suberate, bis(sulfosuccinimidyl) suberate, bis(diazobenzidine), ethylene glycobis(succinimidylsuccinate), disuccinimidyl tartrate, disulfosuccinimidyl tartrate, glutaraldehyde, dithiobis(succinimidyl pro-pionate), dithiobis-(sulfosuccinimidyl propionate), dimethyl 3,3'-dithiobis-propionimidate, bis 2-(succinimidyl-oxycarbonyloxy)ethyl-sulfone, and the like) as well as thiol-reactive homobifunctional crosslinkers (e.g., bismaleidohexane, 1,4-bis-[3-(2-pyridyldithio)propionamido]butane, and the like). Examples of heterobifunctional crosslinkers include, but are not limited to, amine- and thiol-reactive crosslinkers (e.g., succinimidyl 4-(N-maleimidomethyl)-cyclohexane-1-carboxylate, m-maleimidobenzoyl-N-hydroxysuccinimide ester, succinimidyl-4-(p-maleimidophenyl)butyrate, N-(γ-maleimidobutyryloxy)succinimide ester, N-succinimidyl(4-iodoacetyl) aminobenzoate, 4-succinimidyl oxycarbonyl-α-(2-pyridyldithio)-toluene, sulfosuccinimidyl-6-α-methyl-α-(2-pyridyldithio)-toluamido-hexanoate, N-succinimidyl-3-(2-pyridyldithio) propionate, N-hydroxysuccinimidyl 2,3-dibromopropionate, and the like).

Reaction mixtures for attaching capture oligonucleotides can contain additional reagents of the sort typically used in bioconjugation reactions. For example, in certain embodiments, the reaction mixtures can contain buffers (e.g., 2-(N-morpholino)ethanesulfonic acid (MES), 2-[4-(2-hydroxy-ethyl)piperazin-1-yl]ethanesulfonic acid (HEPES), 3-morpholinopropane-1-sulfonic acid (MOPS), 2-amino-2-hydroxymethyl-propane-1,3-diol (TRIS), potassium phosphate, sodium phosphate, phosphate-buffered saline, sodium citrate, sodium acetate, and sodium borate), cosolvents (e.g., dimethylsulfoxide, dimethylformamide, ethanol, methanol, tetrahydrofuran, acetone, and acetic acid), salts (e.g., NaCl, KCl, CaCl$_2$), and salts of Mn$^{2+}$ and Mg$^{2+}$), detergents/surfactants (e.g., a non-ionic surfactant such as N,N-bis[3-(D-gluconamido)propyl]cholamide, polyoxyethylene (20) cetyl ether, dimethyldecylphosphine oxide, branched octylphenoxy poly(ethyleneoxy)ethanol, a polyoxyethyl-ene-polyoxypropylene block copolymer, t-octylphenoxy-polyethoxyethanol, polyoxyethylene (20) sorbitan monooleate, and the like; an anionic surfactant such as sodium cholate, N-lauroylsarcosine, sodium dodecyl sulfate, and the like; a cationic surfactant such as hexdecyltrimethyl ammonium bromide, trimethyl(tetradecyl) ammonium bromide, and the like; or a zwitterionic surfactant such as an amidosulfobetaine, 3-[(3-cholamidopropyl)dimethyl-am-monio]-1-propanesulfonate, and the like), chelators (e.g., ethylene glycol-bis(2-aminoethylether)-N,N,N',N'-tet-raacetic acid (EGTA), 2-({2-[bis(carboxymethyl)amino] ethyl}(carboxymethyl)amino)acetic acid (EDTA), and 1,2-bis(o-aminophenoxy)ethane-N,N,N,N-tetraacetic acid (BAPTA)), and reducing agents (e.g., dithiothreitol (DTT), β-mercaptoethanol (BME), and tris(2-carboxyethyl)phos-phine (TCEP)). Buffers, cosolvents, salts, detergents/surfac-tants, chelators, and reducing agents can be used at any suitable concentration, which can be readily determined by one of skill in the art. In general, buffers, cosolvents, salts, detergents/surfactants, chelators, and reducing agents are included in reaction mixtures at concentrations ranging from about 1 M to about 1 M. For example, a buffer, a cosolvent, a salt, a detergent/surfactant, a chelator, or a reducing agent can be included in a reaction mixture at a concentration of about 1 μM, or about 10 M, or about 100 μM, or about 1 mM, or about 10 mM, or about 25 mM, or about 50 mM, or about 100 mM, or about 250 mM, or about 500 mM, or about 1 M.

The reactions are conducted under conditions sufficient to install the capture oligonucleotides on the microbeads. The reactions can be conducted at any suitable temperature. In general, the reactions are conducted at a temperature of from about 4° C. to about 40° C. The reactions can be conducted, for example, at about 25° C. or about 37° C. The reactions can be conducted at any suitable pH. In general, the reactions are conducted at a pH of from about 4.5 to about 10. The reactions can be conducted, for example, at a pH of from about 5 to about 9. The reactions can be conducted for any suitable length of time. In general, the reaction mixtures are incubated under suitable conditions for anywhere between about 1 minute and several hours. The reactions can be conducted, for example, for about 1 minute, or about 5 minutes, or about 10 minutes, or about 30 minutes, or about 1 hour, or about 2 hours, or about 4 hours, or about 8 hours, or about 12 hours, or about 24 hours, or about 48 hours, or about 72 hours. Other reaction conditions may be employed in the methods of the invention, depending on the composition of the microbeads and the reagents used for installing the capture oligonucleotides.

D. Detection and Identification of Hybridized Polynucleotides

Amplicons are combined with the microbeads such that at least some amplicons are captured onto beads by the capture polynucleotides. Labeled amplicons (e.g., Alexa Fluor 647-labeled amplicons, or ethidium bromide-stained amplicons, as described above) can then be located by visualizing the microbeads under an appropriate filter, e.g., a fluorescence microscope equipped with a BrightLine® Pinkel filter set (Semrock, Rochester NY). In some embodiments, the methods including separating uncaptured amplicons from beads having captured amplicons. The microbeads can be dispersed on a microscope slide for detection of labeled amplicons and recording of lanthanide spectral signatures. Alternatively, the microbeads can be distributed in a well-plate or like apparatus having addressable positions prior to detection. As an alternative to microscopy, beads having labeled, hybridized amplicons can be detected using a flow cytometer with fluorescence-activated particle sorting.

Following identification of beads containing duplexes formed by amplicons and capture polynucleotides on microbead surfaces, microbe-identifying sequences in the captured amplicons are determined by examining the lanthanide spectral signatures of individual microbeads. In some embodiments, beads with and without detectable amplicons can be imaged so as to identify the spectral code and to quantify the amount of amplicon bound to the beads. In this manner, the absence of particular microbial polynucleotides in a given sample can also be characterized. In general, each of the spectral signatures contains signals generated from predetermined amounts of one or more lanthanides (e.g., one or more Eu-, Dy-, Sm-, Ce-, Tb-, La-, Pr-, Nd-, Gd-, Ho-, Er-, Tm-, Yb-containing nanoparticles). Lanthanides in the microbeads can be excited with UV light (e.g., 275 nm, 285 nm, or 292 nm) and emitted luminescent signals can be detected in the range of 400-800 nm (e.g., 435 nm, 474 nm, 527 nm, 536 nm, 546 nm, 572 nm, 620 nm, 630 nm, 650 nm, or 780 nm). As a non-limiting example, a set of unique spectral signatures can be prepared with microparticles that contain europium-dope yttrium orthovanadate ($YVO_4$:Eu) to generate a reference signal and varying amounts of $YVO_4$:Dy, $YVO_4$:Sm, $YVO_4$:Tm, and $LaPO_4$:CeTb. Other lanthanide-containing materials, such as $YVO_4$:Ho, $YVO_4$:Er, $NaYF_4$:YbEr, and $NaYF_4$:YbTm, can be used in this fashion.

Codes can be read upon imaging of the excited microbeads at different wavelengths chosen to best discriminate between individual emission spectra. The raw images can be converted to intensity images for each lanthanide by linear unmixing to determine the most likely linear combination of lanthanide nanoparticles to have produced the observed spectra at each pixel in an image. Individual codes can then be reported as the ratio of intensities of each coding LN relative to the YVO4:Eu reference signal. A transformation matrix can be applied to register the measured ratios onto the known input ratios, as described by Nguyen et al. ((2017) Advanced Optical Materials, 5, 1600548), and a Gaussian mixture model (GMM) can be used to fit the mean ratios and covariance matrices that describe each code cluster, and then assign each bead to its most likely code cluster.

Also provided herein are microbeads comprising a lanthanide spectral signature and a plurality of copies of a capture polynucleotide immobilized on the microbead, including all of the embodiments described above. Each capture polynucleotide in a plurality of the microbeads comprises a predetermined sequence and each capture polynucleotide is paired with a lanthanide spectral signature, such that the predetermined sequence can be identified based on the lanthanide spectral signature. In some embodiments, each capture polynucleotide comprises a nucleic acid sequence that hybridizes to a bacterial 16S rRNA gene sequence. In other embodiments, each capture polynucleotide comprises a nucleic acid sequence that hybridizes to a bacterial 23S rRNA gene sequence. In some embodiments, the capture polynucleotides comprise a nucleic acid sequence that hybridizes to a V3 variable region, a V4 variable region, or a V6 variable regions in a bacterial 16S rRNA gene sequence. In some embodiments, each of the capture polynucleotides comprises a nucleic acid sequence able to hybridize a *Pseudomonas* gene sequence, a *Streptococcus* gene sequence, *Staphylococcus* gene sequence, a *Neisseria* gene sequence, an *Acinetobacter* gene sequence, an *Escherichia* gene sequence, an *Enterobacter* gene sequence, or a *Klebsiella* gene sequence. In some embodiments, each of the lanthanide spectral signatures comprises a europium (Eu) signal, a dysprosium (Dy) signal, a samarium (Sm) signal, a cerium (Ce) signal, a terbium (Tb) signal, a lanthanum (La) signal, a praseodymium (Pr) signal, a neodymium (Nd) signal, a gadolinium (Gd) signal, a holmium (Ho) signal, an erbium (Er) signal, a thulium (Tm) signal, an ytterbium (Yb) signal, or a combination thereof. In some embodiments, each of the microbeads comprises a plurality of lanthanide nanoparticles. In some embodiments, the lanthanide nanoparticles comprise a lanthanide-doped host lattice. In some embodiments, the host lattice is yttrium orthovanadate, lanthanum phosphate, or a combination thereof. In some embodiments, each of the microbeads further comprises a crosslinked polymer, wherein the capture polynucleotides are covalently bonded to the crosslinked polymer. In some embodiments, a plurality of the microbeads contains at least 100 lanthanide spectral signatures. In some embodiments, the plurality of microbeads contains at least 1000 lanthanide spectral signatures.

E. Identification of Pathogens Using Patterns of Hybridization

It will be appreciated that although a predetermined sequence in a capture polynucleotide can be designed for hybridization to a particular target sequence in amplicons (e.g., a sequence specific to a particular microbe of interest), the same predetermined sequence may hybridize at varying levels to other sequences under certain conditions. Accordingly, amplicons generated from a sequence-agnostic target (including polynucleotides from a previously unknown or uncharacterized bacterium) could hybridize to multiple capture probes present in a panel of capture probes at different levels, thereby producing a pattern showing different magnitudes of hybridization to individual capture probes. The hybridization pattern can be evaluated in conjunction with the spectral codes associated with the individual capture probes. The measured pattern of hybridization can be compared to a predicted pattern of hybridization. To generate the predicted pattern, the hybridization binding level of an amplicon to capture polynucleotides can be predicted using thermodynamic models as described, for example by Aghazadeh, et al. (*Sci. Adv.* 2016; 2: e1600025). In one aspect, the hybridization binding level can be predicted based on the Gibbs free energy of hybridization (Alexander et al. (2015, "Evaluation of the Gibbs Free Energy Changes and Melting Temperatures of DNA/DNA Duplexes Using Hybridization Enthalpy Calculated by Molecular Dynamics Simulation", *J. Phys. Chem. B* 2015, 119, 49, 15221-15234, Tulpan et al. (2010), "Free energy estimation of short DNA duplex hybridizations", BMC Bioinformatics. 2010; 11: 105). In another embodiment, the hybridization binding level can be predicted based on melting temperatures (Tm) or the Helmholtz Free Energy (Markham and Zuker (2004), "DINAMelt web server for nucleic acid melting prediction", Nucleic Acids Res., 33, W577-W581; Dimitrov and Zuker (2004), "Prediction of hybridization and melting for double-stranded nucleic acids", Biophys. J., 87, 215-226; SantaLucia (1998), "A unified view of polymer, dumbbell, and oligonucleotide DNA nearest-neighbor thermodynamics", PNAS, 95, 1460-1465; Schmitta and Knotts (2011), "Thermodynamics of DNA hybridization on surfaces", J. Chem. Phys. 134, 205105). In yet another embodiment, the hybridization binding level can be predicted using similarity metrics, such as E-score (Anderson & Brass (1998), "Searching DNA databases for similarities to DNA sequences: when is a match significant?", Bioinformatics, 14 (4), 349-356; Johnson et al. (2008, "NCBI BLAST: a better web interface", Nucleic Acids Research, 36 (Web server issue), W5-W9). The predicted hybridization pattern and the measured hybridization pattern can then be used in an analysis to determine which pathogen from the panel is most likely present in a sample.

Thus, in one embodiment, a hybridization pattern analysis is performed by comparing the measured hybridization pattern to the predicted hybridization pattern. In one approach, for an amplicon of a given species, such as an amplicon of the V6 region of *Acinetobacter baumannii*, the Gibbs free energy of hybridization is calculated for the amplicon binding to each capture polynucleotide in the panel, where the panel is comprised of a plurality of capture polynucleotides. This calculation may be performed for all amplicons of all species the panel is designed to detect. In one approach, the assay of the present disclosure is then performed on a sample where the pathogen is unknown. In one aspect, a correlation coefficient is calculated to measure the correlation between the measured hybridization pattern and the predicted hybridization patterns based on the Gibbs free energy of hybridization. In one embodiment, the Pearson correlation coefficient, known as r, R or Pearson's r, is calculated for this analysis. However, any type of correlation coefficient that presents a numerical measure of correlation can be used to perform the analysis.

In one approach, the Pearson correlation coefficient for the measured hybridization signals and the predicted hybridization energies is calculated for every pathogen amplicon the panel is designed to detect. By analyzing which pathogen amplicon has the highest Pearson correlation coefficient (R) and, thus, is best correlated with the measured unknown pathogen, it can be determined which pathogen from the panel is most likely present in the sample. In one aspect, negative Pearson correlation coefficients are omitted from consideration in this analysis. In one embodiment, the analysis is performed by considering all capture polynucleotide. In another embodiment, the analysis is performed by setting a certain threshold to only consider capture polynucleotide with hybridization energies above or below this threshold. For example, the correlation analysis may be performed using only capture polynucleotide predicted to bind to the target amplicon with a Gibbs free energy less than −7 kcal/mol. In another example, the correlation analysis may be performed using only capture polynucleotide predicted to bind to the target amplicon with a Gibbs free energy less than −10 kcal/mol.

In one embodiment, the assay of the present disclosure targets multiple variable regions, such as the V3 and the V6 within the 16S ribosomal DNA for a particular species. This can prove useful if there is sequence similarity between multiple species in one region, such as in V6, but sequences in a different region, such as V3, show differences and, therefore, may be used to discriminate these species. In one embodiment, the Pearson correlation coefficient analysis described above is performed for all V3 amplicons and for all V6 amplicons separately. In another embodiment the Pearson correlation coefficient analysis is performed by combining the predictions and measurements for V3 and V6 to calculate a single Pearson correlation coefficient representing the combined measurement. In one embodiment, measurement of other regions, such as the V5 region, are combined with measurements for V3 and V6.

In one embodiment, the Pearson correlation coefficient analysis described above is performed by correlating measurements of an unknown sample with measurements of known pathogens. For example, the analysis may be performed with measurements of known pathogens in the place of predicted hybridization signatures.

In a further embodiment, the hybridization pattern analysis described above can be used for detecting the presence of pathogens that the capture polynucleotides were not specifically designed to probe for. In one approach, this analysis is performed similarly as described above by using amplicons generated from a sequence-agnostic target to calculate the predicted Gibbs free energy of hybridization with the existing capture polynucleotides in the panel. The presence of the sequence-agnostic target can be established when the predicted pattern is observed, i.e. by determining whether the measured hybridization pattern is well correlated (showing a high Pearson correlation coefficient, R) with the predicted hybridization pattern of the unknown species.

F. Specificity Analysis and Optimization of Capture Polynucleotide Panels

In one embodiment, the specificity of the assay according to the present disclosure when using the above described correlation analysis is assessed by performing an area under a receiver operating characteristic curve (AUROC) analysis. For example, this can be performed by setting a threshold of the Pearson correlation coefficient (R) to call a species (or amplicon) present and analyzing how many (or what fraction of) species would be detected as true positives or false positives. The curve may be generated by scanning this threshold through all possible values for R (0 to 1), and plotting the fraction of true positive and false positive detected species at each detection threshold.

In one embodiment, a similar correlation analysis as described can be used to select an optimal panel of capture polynucleotides. In one approach, for an amplicon of a given species, the Gibbs free energy of hybridization is calculated for the amplicon binding to each capture polynucleotide in the panel, where the panel is comprised of a plurality of capture polynucleotide. This calculation may be done for all amplicons of all species the panel is designed to detect. To assess the predicted specificity of a panel, the Pearson correlation coefficient is calculated to measure the correlation of the predicted hybridization patterns for a given amplicon, with the predicted hybridization patterns for all other amplicons, as well as itself. In one aspect, this analysis is performed by considering all capture polynucleotides. In another aspect, the analysis is performed by setting a threshold to only consider capture polynucleotides with hybridization energies above or below this threshold. For example, the correlation analysis may be performed using only capture polynucleotides predicted to bind to the target amplicon with a Gibbs free energy less than −7 kcal/mol. In one embodiment, negative Pearson correlation coefficients are omitted for the analysis.

In one embodiment, the Pearson correlation coefficient values are then used to generate a receiver operating characteristic curve by setting a threshold of the Pearson correlation coefficient (R) to call a species (or amplicon) present and analyzing how many (or what fraction of) species would be detected as true positives or false positives. In one approach, the curve is generated by scanning this threshold through all possible values for R (0 to 1), and plotting the fraction of true positive and false positive detected species at each detection threshold. In one aspect, the area under the receiver operating characteristic curve (AUROC) is calculated as a metric of specificity. In one embodiment, an optimal capture polynucleotide panel can be found by iteratively creating panels of capture polynucleotides from the multitude of candidate capture polynucleotides, and maximizing the predicted AUROC.

III. Examples

Example 1. Preparation of Lanthanide-Encoded Beads

Beads were prepared using a microfluidic bead synthesizer device that has been previously described. See, Gerver, et al. (2012) *Lab on a Chip,* 12, 4716-4723; Nguyen, et al. (2017) *Advanced Optical Materials,* 5, 1600548; Harink, et al. (2019) *PLOS One,* 14(3): e0203725; Nguyen, et al. (2018) *bioRxiv* 306779; Brower, et al. (2017) *J. Vis. Exp.* (119), e55276. The microfluidic device was fabricated in polydimethylsiloxane (PDMS, RTV 615, Momentive Performance Materials, Albany, NY) by multi-layer soft lithography using 4" test-grade silicon wafers (University Wafer, South Boston, MA) coated with multiple layers of SU-8 (Microchem Corp., Newton, MA) and AZ50 XT photoresists (Capitol Scientific, Austin, TX) patterned by standard photolithography processes. Lanthanide nanophosphors were synthesized using microwave synthesis in a Biotage Initiator (Biotage AB, Uppsala, Sweden), using methods previously published [1,2,4]. See, Gerver, et al. (2012); Nguyen, et al. (2017); Nguyen, et al. (2018); supra.

Encoded beads were generated by varying ratios of four input solutions each containing different lanthanide nanoparticles. The four monomer input solutions used in the microfluidic bead synthesizer all contained purified water with 42.8% v/v 700 MW PEG-diacrylate (Sigma-Aldrich), 3% v/v lithium phenyl-2,4,6-trimethylbenzoylphosphinate (LAP) photoinitiator dissolved in water at 19.6 mg/mL, and 5% v/v $YVO_4$:Eu. A first input solution also contained 21.3% v/v $YVO_4$:Dy; a second input solution contained 21.3% v/v $YVO_4$:Sm; and a third input solution contained 21.3% v/v $YVO_4$:Tm. Droplets were formed by flowing the aqueous streams into a T-junction for entry into a continuous flowing stream of HFE 7500 oil (3M Novec) that contained 2% v/v ionic Krytox as surfactant to eliminate droplet merging and sticking to the PDMS walls. The droplets were polymerized into beads by exposing the channel (downstream of the T-junction) with the stream of droplets to UV light with a liquid lightguide. Beads from each code were collected into a 96 well plate before being washed as described in the bead functionalization section.

Figure 2B:
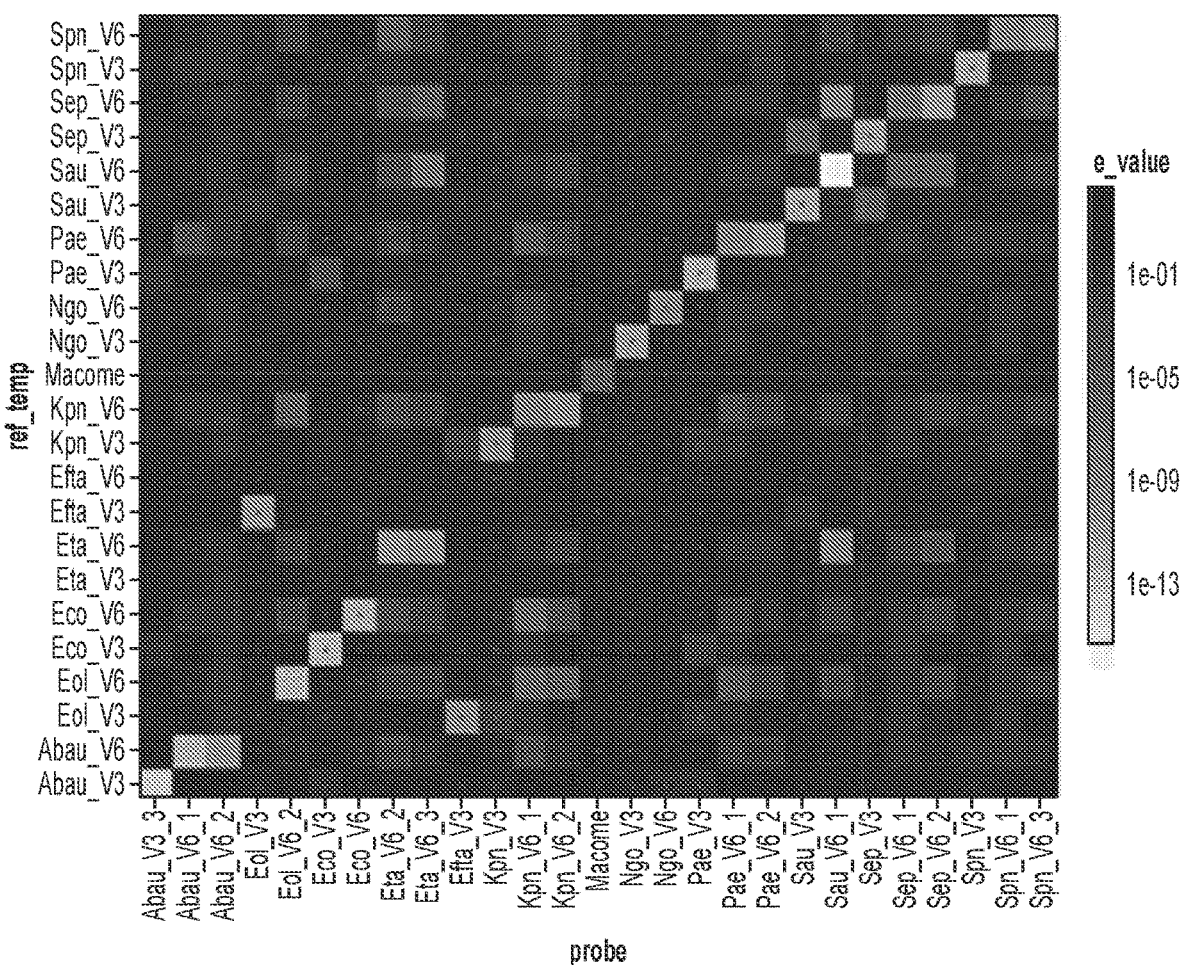
FIG. 2B shows a heat-map depicting the specificity of candidate capture polynucleotides.
Figure 2C:
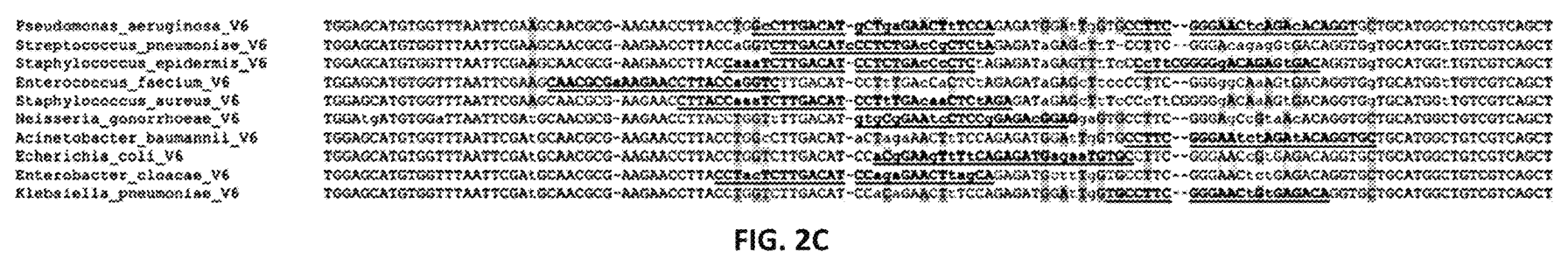

Example 2. Design of Hybridization Probes for Bead-Oligonucleotide Functionalization An Algorithm for the Identification of Hybridization Oligonucleotides that Target Specific DNA Sequences A program was developed to aid in finding hybridization oligonucleotides that would be specific to a target DNA sequence in the presence of other similar DNA sequences (FIG. 2). Given a pool of sequences, provided as a file in FASTA format, the program outputs candidate hybridization oligonucleotides that meet designated design specifications. The program uses a k-mer based approach (where a k-mer represents a sub-string of DNA bases within the sequence provided) that works in the following way: (i) given a set of sequences, the minimum k-mer length that splits all sequences up into unique, unambiguous k-mers is identified; (ii) all sequences are broken into unique k-mers using the identified value of k; (iii) all k-mers that occur multiple times within the collection of sequences of interest are removed from consideration (such that only unique kmers are considered); (iv) a matrix of Hamming distances between all unique k-mers within a single sequence and all other k-mers from all other sequences is generated; (v) all rows that contain a Hamming distance of 1 for any k-mer pair are removed (unique k-mers must be at least 2 mutations from any other k-mer in the pool); (vi) Hamming distances are mapped to similarity scores S by calculating S=k−Hamming distance and minimize the sum of the squared similarity scores; (vii) k-mers are found within the original sequences; (viii) sliding window primer design is performed for oligonucleotides of varying size until desired Tm and other properties are achieved to generate a pool of potential hybridization oligos; (ix) the oligo pool is pruned to a single representative oligo based on pruning properties; and (x) the hybridization oligos are reported in a machine/human readable format.

An Algorithm for the Identification of Species-Specific Hybridization Oligonucleotides For the identification of species-specific hybridization oligonucleotides a program was developed that uses k-mers which uniquely distinguish a hypervariable region associated with a particular species of interest from all other species in the pool. In this approach, k-mers for each species are required to have a specified Hamming distance from the hyper variable region sequences of other species. Furthermore, this algorithm does not disqualify k-mers that appear multiple times in a particular species' sequence. The algorithm explores a greater search space by not requiring that a selected panel of probes contains k-mers of the same length, and instead considering all combinations of probes that are within a certain length range. The algorithm further optimises for experimental assay performance by using RNAcofold (from the Vienna RNA package 2.4.14; Lorenz et al. (2011), ViennaRNA Package 2.0. Algorithms for molecular biology, 6(1), 26) to calculate the affinities between probes and amplicons. Capture polynucleotides that are predicted to exhibit strong, species-specific binding are ultimately selected.

The approach works in the following way: (i) each hypervariable region is split into 20-30 nucleotide subsequences; (ii) all k-mers between lengths 20 and 30 are identified for each species, concordant with commonly used probe length ranges for fluorescence in situ hybridization and hybridization-based sequencing (Biliveau et al. (2017), "OligoMiner provides a rapid, flexible environment for the design of genome-scale oligonucleotide in situ hybridization probes". *PNAS* 115(10), 2183-2192); (iii) redundant k-mers are removed from consideration; (iv) a matrix of Hamming distances between all unique k-mers within a single sequence and all other k-mers from all other sequences is generated; (v) k-mers that contain a Hamming distance less than 2 to any other k-mer from other sequences are removed (unique k-mers must be at least 2 mutations from any other k-mer in the pool; Letowski et al. (2004), "Designing better probes: effect of probe size, mismatch position and number on hybridization in DNA oligonucleotide microarrays", Journal Microbiol Methods, 57(2), 269-278); (vi) the pool is further narrowed by limiting probes to a melting temperature range of 55 to 65 degrees Celsius; (vii) the predicted Gibbs free energy of hybridization between each pair of capture polynucleotide candidate and amplicon is calculated using the program RNAcofold; (viii) the absolute value of this binding energy is maximized for species-specific pairs and minimized for non-specific combinations of amplicon and capture polynucleotide, as the overall Gibbs free energy change is a strong predictor of both hybridization efficiency and specificity (Yilamz et al. (2004), "Mechanistic approach to the problem of hybridization efficiency in fluorescent in situ hybridization", Appl. Environ. Microbiol., 70(12), 7126-7139; Matveeva et al. (2018), "Sequence characteristics define trade-offs between on-target and genome-wide off-target hybridization of oligoprobes", PloS one, 13(6)); (ix) one or two capture polynucleotides with optimal binding energetics per species are selected for assay inclusion.

Table 5 shows the pathogens targeted in Example 2, 4, and 5 include a variety of pathogens related to sepsis and hospital acquired infections. The inclusion of *Neisseria gonorrhoeae* demonstrates the utility and feasibility of using this spectrally encoded multiplexed assay for the detection of co-infections.

dimethylformamide (DMF) and then draining the solvent through the filter which retains the beads. This washing procedure was repeated with dichloromethane (DCM), methanol, and finally DMF again. The DMF was drained and the beads were washed 3 times in dimethyl sulfoxide (DMSO). After the final wash, the beads were resuspended in 1 mL DMSO prior to addition of 1-ethyl-3-(3-dimethyl-aminopropyl)carbodiimide (EDC; 20 μL of 300 mM stock solution in DMSO); 1-hydroxy-7-azabenzotriazole (HOAT; 20 μL of 60 mM stock solution in DMSO), and N,N-diisopropylethylamine (DIPEA; 20 μL of 300 mM stock solution in DMSO). The beads were incubated in this EDC, HOAT, and DIPEA solution for 15 minutes on a shaker (or rotator) for mixing. After 15 minutes, 10 μL (from 100 μM stock solution) of oligonucleotides modified at the 5' end

TABLE 5

Targeted Pathogens

| Organism | Characteristics |
|---|---|
| *Escherichia coli* | Gram-negative; found in lower intestine; cause of foodborne illness. |
| *Staphylococcus aureus* | Gram-positive; found in nose, respiratory tract, skin; leads to abscesses, respiratory infections, and food poisoning; can be methicillin-resistant. |
| *Pseudomonas aeruginosa* | Gram-negative; can be multidrug-resistant; associated with ventilator-associated pneumonia |
| *Acinetobacter baumannii* | Gram-negative; opportunistic pathogen; associated with nosocomial infections. |
| *Enterococcus faecium* | Gram-positive; alpha-hemolytic; commensal in gastrointestinal tract, but can cause meningitis or endocarditis; can be vancomycin-resistant. |
| *Enterobacter cloacae* | Gram-negative; gut flora; known to cause obesity in germfree mice under certain conditions. |
| *Klebsiella pneumoniae* | Gram-negative; lactose-fermenting; seen in people with a weakened immune system; associated with bronchitis. |
| *Neisseria gonorrhoeae* | Gram-negative; causes the sexually transmitted infection gonorrhea as well as septic arthritis. |
| *Staphylococcus epidermis* | Gram-positive; part of normal skin flora; forms biofilms on instruments and leads to hospital acquired infections. |
| *Streptococcus pneumoniae* | Gram-positive; major cause of pneumonia and meningitis. |

Example 3. Bead-Oligonucleotide Functionalization

To prepare beads for oligo conjugation, the beads were carboxylated via Michael addition to acrylate groups. Beads (up to 30,000) were collected in filter bottom syringe tubes (PP-Reactor 2 mL with PTFE frit, catalog number V020TF051, Biotage LLC). Each separate reaction tube contained beads of a single spectral code. The beads were washed 3 times by adding 1 mL dimethylformamide (DMF) and then draining the solvent through the filter which retains the beads. This washing procedure was repeated with dichloromethane (DCM), methanol, and finally DMF again. The beads were then resuspended in 1.5 mL DMF, and 54 μL of 3-mercaptopropionic acid and 50 μL of pyridine were added. The reaction vessel was capped and incubated for 24 hours at room temperature. Mixing of the beads in the reaction solutions was achieved by rotating the tubes on an end-over-end rotator, or alternatively by shaking on vortex mixer (Catalog number S006VO002, Biotage LLC). For this procedure, 1 ng of beads was estimated to amount to approximately 20,000 beads, and available sites for carboxylation were estimated to be present at 0.32 mmol/g. At least 20 equivalents of 3-mercaptopropionic acid and pyridine, with respect to the carboxylation sites on the beads, were used in the reactions.

Keeping the beads in the filter tubes used during carboxylation, the beads were washed 3 times by adding 1 mL with an amino-terminated 12-carbon spacer (the "5AmMC12" modification from Integrated DNA Technologies) were added, as well as an additional 20 μL of EDC, HOAT, and DIPEA. At this step, specific oligonucleotides were added to specific reaction tubes containing beads of a desired spectral code. As non-limiting examples, hybridization oligonucleotides for the V6 variable region in *Escherichia coli* 16S ribosomal DNA ("v6Eco") were added to reactions with beads of code 1, and hybridization oligonucleotides for *Pseudomonas aeruginosa* were added to reactions with beads of code 2. The reaction mixtures were incubated at room temperature for 8-24 hours (e.g., 16 hours) on a shaker or rotator. The reaction mixtures were then neutralized by adding 50 μL ethanolamine (500 mM stock solution in DMSO) to each mixture and incubating for 1 hour. Following conjugation, the beads were washed with phosphate buffered saline (PBS) containing 0.1% (v/v) Tween 20. The beads were finally resuspended in PBS with 0.1% Tween 20 and stored (e.g., at 4° C.). The beads were kept according to their separate codes, or they were pooled together into a combined code set. In order to reduce bead-to-bead variation in conjugation of fluorescently labeled oligos, carboxylation and conjugation reactions were performed with up to about 60,000 beads (e.g., around 1000 beads) per reaction. Conjugation reactions were also performed with input oligonucleotide concentrations ranging from 10 nM to 200 µM to control the amount of oligonucleotide coupled to the bead (FIG. 3D).

Example 4. Multiplexed Pathogen Detection Assay

Figure 4:
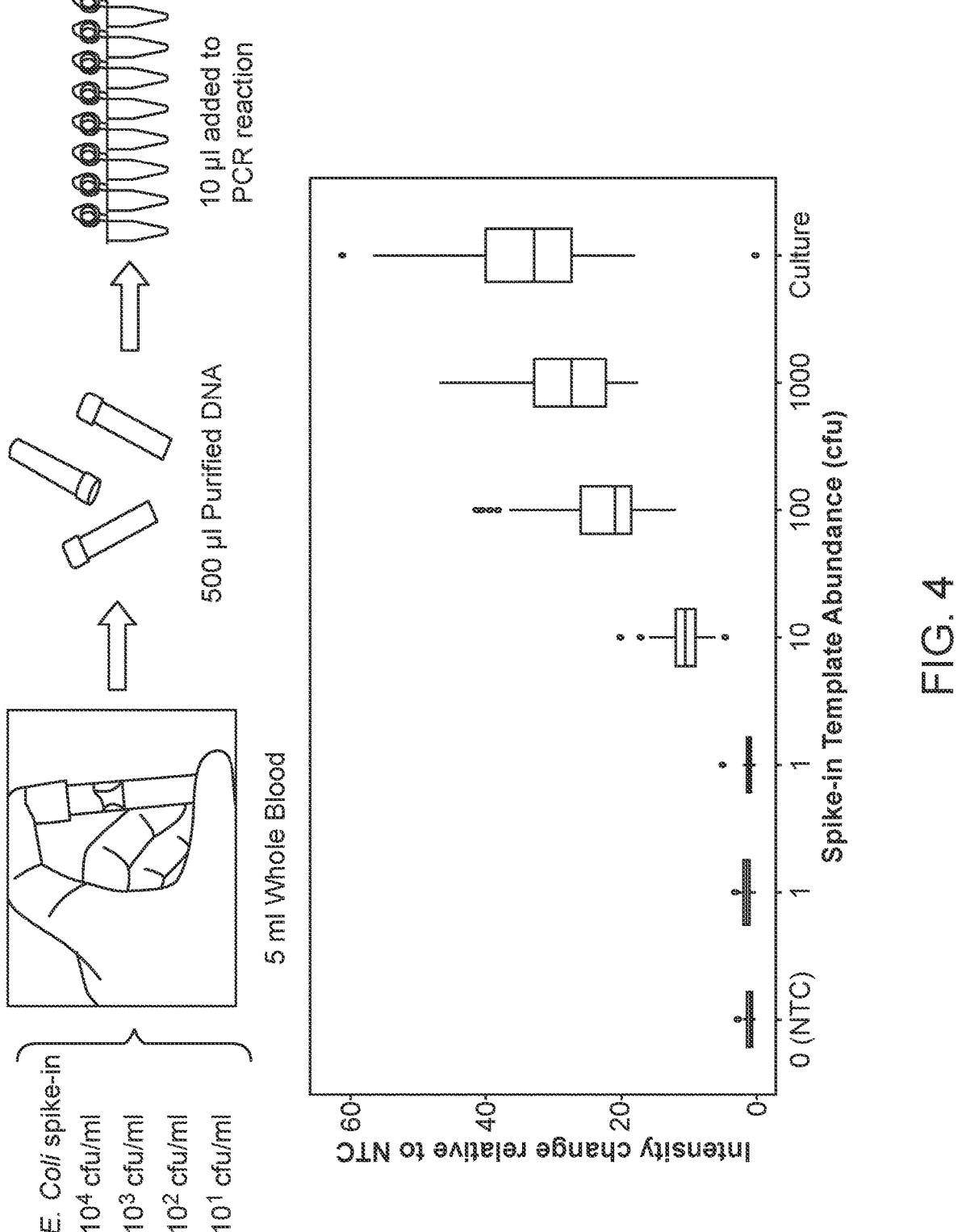
FIG. 4 shows the testing sensitivity of a whole blood assay according to the present disclosure.

To test the sensitivity of the assay in detecting low abundance pathogens in the presence of blood (FIG. 4), *E. coli* was added to 5 mL whole blood at concentrations of 10 cfu/ml to 10,000 cfu/ml. DNA from whole blood was purified using the QIAamp DNA Blood Midi Kit (Qiagen), and eluted into 500 µL tris buffer. From this 500 µL sample, 10 µL was added to each PCR reaction.

PCR Application

Primers were selected to amplify the V3, V4 and V6 variable regions of the 16S ribosomal subunit gene (Table 1 above). Forward primers were labeled at the 5' end with a fluorophore (e.g., Alexa647 or Cy5), and reverse primers were phosphorylated. PCR was performed using the Invitrogen Platinum II Taq Hot-Start DNA Polymerase (Thermo Fisher Scientific) following the manufacturer guidelines. Specifically, PCR reactions contained 10 µL 5× Platinum II Taq Host-Start DNA Polymerase Master Mix, 1 µL dNTPs (10 mM), 1 µL V6 Forward primer (from 10 µM stock solution, resulting in 200 nM final concentration), 1 µL V6 Reverse primer, 1 µL V3 Forward primer, 1 µL V3 Reverse primer, 0.4 µL Platinum II Taq Host-Start DNA Polymerase, 24.6 µL water, and 10 µL of solution containing sample template (e.g., *E. coli* DNA at 1 ng/mL concentration, or human DNA purified from whole blood). PCR was performed by heating this reaction mixture for 2 minutes at 95° C. followed by 35 cycles of 10 s at 95° C. and 30 s at 60° C. Reactions were also performed with the forward primer at 500 nM and 750 nM, in excess of the reverse primer, in order to generate single stranded products for downstream hybridization. In an alternative protocol, real-time quantitative PCR (qPCR) is performed to measure the abundance of bacterial DNA present in a sample prior to multiplexed detection of pathogen sequences. Quantitative PCR is performed using the iTaq Universal SYBR Green Supermix (BioRad), as 10 µL 2× Supermix, 3 µL water, 1 µL Forward Primer (from 10 µM stock), 1 µL Reverse Primer, and 5 µL solution with sample template molecules.

In order to produce single stranded DNA for hybridization, a lambda exonuclease treatment was performed to digest the phosphorylated strand of the PCR amplicon (created by the phosphorylated reverse primer). A master mix containing 18 µL water, 5 µL lambda exonuclease buffer (New England Biolabs, Catalog #M0262S), and 1 µL lambda exonuclease (New England Biolabs, Catalog #M0262S) for each reaction was prepared, and then 25 µL was added to each tube (e.g., 200 µL strip tubes or 96 well plates) containing the product from the PCR reaction. The exonuclease reaction was then performed by incubating at 37° C. for 30 minutes, followed by a heat inactivation of the lambda exonuclease at 75° C. for 10 minutes. The products of this reaction were used for hybridization.

Hybridization to Encoded Beads

Figure 5:
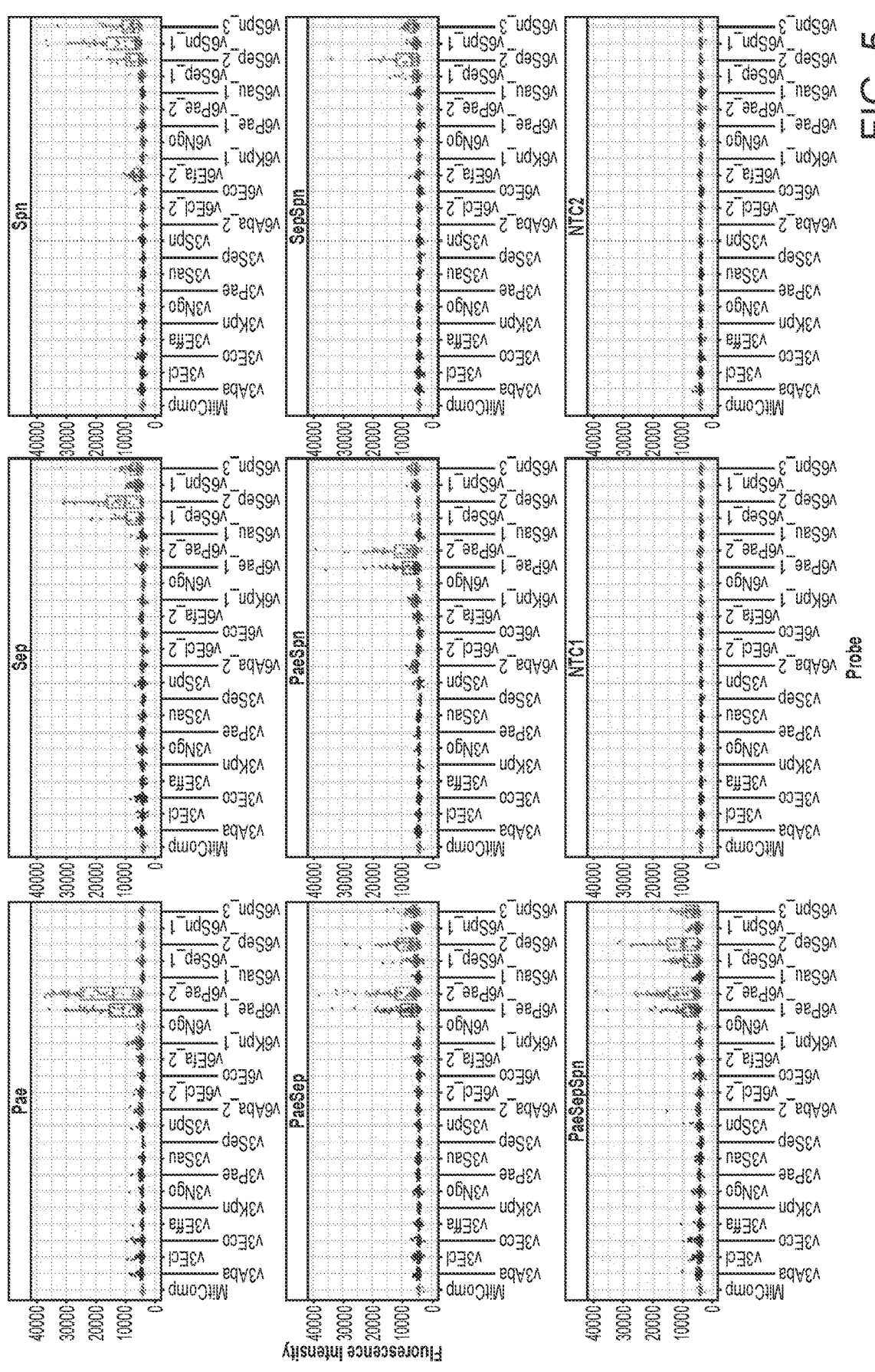
FIG. 5 shows the multiplexed detection of different pathogens.

A pooled library of spectrally encoded beads functionalized with hybridization oligonucleotides was added to the products of the exonuclease reactions. Employment of approximately 100 beads per code can be particularly useful in the analysis of clinical samples, although 1 to 1000 beads per code can typically be used within operational limits. Robust hybridization was observed using a variety of commercially available buffers including PerfectHyb Plus Hybridization Buffer (Sigma-Aldrich), and SSC buffers. For the experiments shown in FIG. 5, beads were initially treated with PBS containing 2% bovine serum albumin and 0.1% Tween to prevent non-specific adsorption of biomolecules to the beads. This was followed by washing away this blocking solution with a hybridization buffer containing 6×SSC, 0.1% salmon sperm DNA, 0.6% SDS, and 2% BSA. This hybridization buffer and set of encoded beads was added to the PCR/exonuclease reaction products prior to hybridization. During hybridization, the reaction mixture was heated to 80° C. and then cooled at 1° C./min to room temperature while the beads were mixed on a thermal-shaker (Eppendorf). Hybridization time was reduced by rapidly ramping the temperature from 80° C. to 65° C. over 1 minute on a Peltier element PCR thermocycler, followed by a 4 minute incubation at 65° C., then a 4 minute incubation at 60° C. (which is the designed Tm of the hybridization oligos, and is further stabilized at this temperature by using the Platinum II Taq Polymerase PCR kit from Invitrogen), then a 4 minute incubation at 55° C. (below probe Tm), all while the beads were mixed within the solution. Finally, the beads were cooled to room temperature and washed by centrifuging the beads, removing the supernatant, and adding a wash buffer. The beads were then washed 3 times by spinning down the beads to pellet them at the bottom of the reaction tube and removing the supernatant before adding wash buffer again. This can alternatively be done with a filter system. The wash buffer (0.1% SSC, 0.5% SDS) was designed to be low-salt for added stringency and reducing the energetic likelihood that a hybridized oligonucleotide would unbind and then re-bind to the wrong probe. Though less ideal, the beads may alternatively be washed with 0.1% Tween 20 in PBS.

Bead Imaging

The beads are then imaged on a glass slide by microscopy with standard epi-fluorescence excitation to quantify the amount of dye-labeled DNA that has hybridized to each bead, and with UV excitation and collection of emitted light at multiple wavelengths to quantify emitted lanthanide luminescence and thus identify the embedded spectral code. Due to the 1:1 linkage between spectral codes and hybridization probes sequences, this spectral code of each bead is used to identify which oligonucleotide sequence is presented on each bead, and the fluorescence signal from each bead is a measure of the amount of complementary target DNA present in the sample. By using the spectral code of the beads to track the identity of each oligonucleotide sequence being assayed, many oligonucleotides may be tracked within a single reaction volume. The methods for imaging and performing image analysis have been previously presented (see, Gerver (2012), Nguyen (2017), Harink (2019), Nguyen (2018), supra).

Analysis

Hybridization probes are assessed for similarity by E-score (FIG. 2B), by using BLASTn (NCBI). The Gibbs free energy of hybridization (FIG. 6) was calculated using the UNAFold through "The DINAMelt Web Server" from the University of Albany. These affinities and sequence similarities can be used to predict the extent of cross-reactivity that a particular pathogen sequence will have to multiple hybridization probes, and this affinity matrix A can be used to determine the presence of specific combinations of pathogens, x, even in the case of multiple hybridization oligonucleotides showing signal, b, by solving for x in Ax=b. The presence of pathogens may also be assessed using Bayesian approaches. A student t-test was performed to assess the presence of bacteria in the multiplexed pathogen assay by looking at the significance of the difference between bead populations in reactions with sample added and beads in negative control reactions with not template added (no-template control, "NTC"). Measuring both the V3 and V6 region can be used to increase confidence in calling a pathogen detected, and can be used in logical combination to identify the presence of pathogens even if detection in one variable region shows affinity to other hybridization oligos.

Example 5. Illustrative Example for Identifying Species in the Assay According to the Present Disclosure Using Pattern of Hybridization Analysis The identification of a pathogen present in the assay according to the present disclosure can be performed by comparing the measured hybridization signal to the predicted amplicon-capture polynucleotide hybridization energies. FIG. 9 shows an illustrative example of such an analysis. An amplicon may be predicted to bind to multiple capture polynucleotides with different affinities (referred to as predicted hybridization patterns, or signatures), and may be measured to bind to multiple capture polynucleotide with different affinities (referred to as measured hybridization patterns, or signatures). The process then uses the Pearson correlation coefficient calculated from the thermodynamic predictions of amplicon-capture polynucleotide affinities (Gibbs free energy of hybridization) to identify species in the assay.

Figures 9A, 9B, 9C:
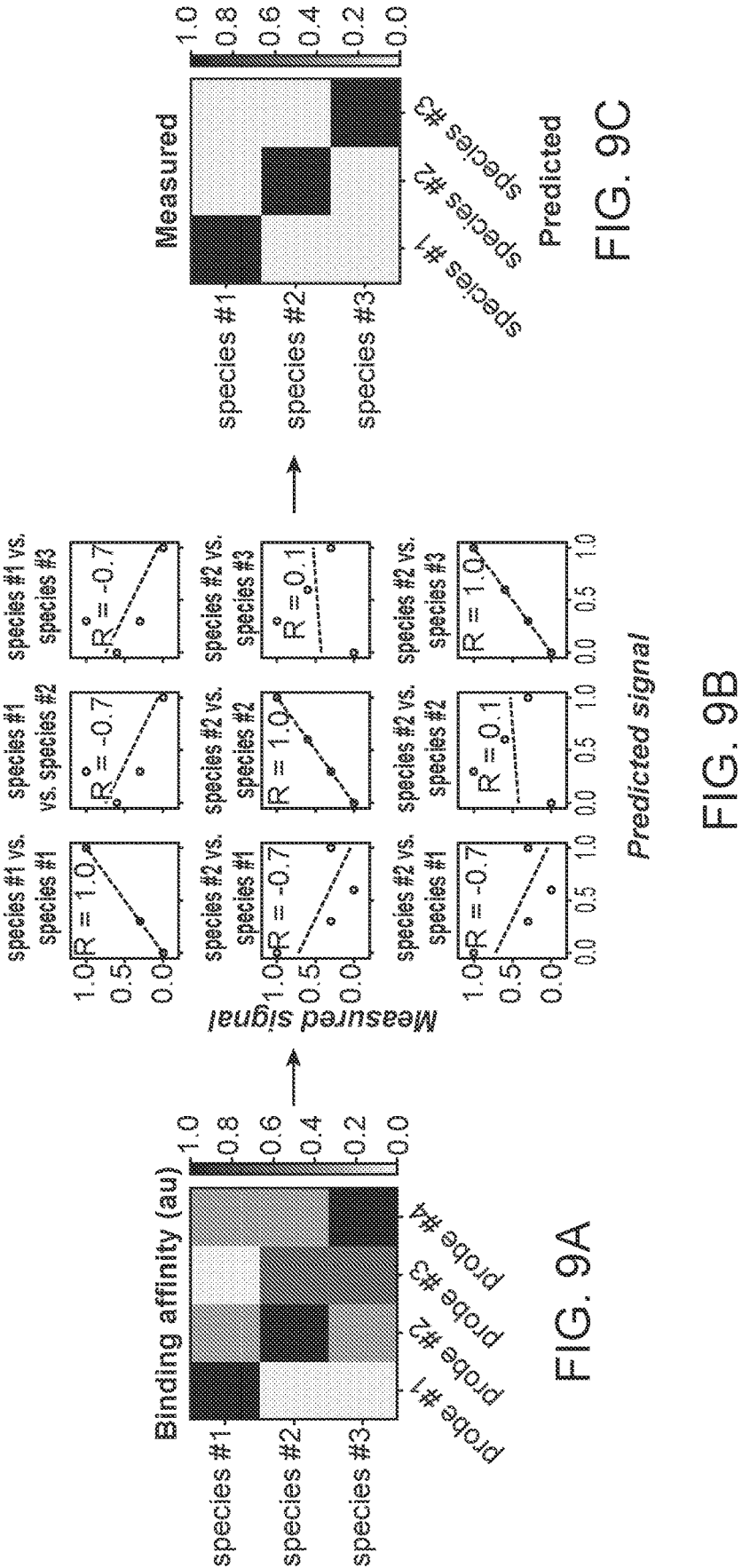
FIG. 9A shows a heatmap illustrating three species that bind with different affinities to three capture polynucleotides.
FIG. 9B shows illustrative examples of Pearson correlation coefficients (r) for the measured hybridization signal and predicted hybridization energies.
FIG. 9C shows a heatmap illustrating the Pearson correlation coefficients shown in FIG. 9B.

The calculation was performed with an example of three species that bind with different affinities to three capture polynucleotides (FIG. 9A). For each species (e.g. "sp1"), the measured hybridization signal was plotted against the predicted hybridization energy for itself (e.g. "sp1 vs sp1") and for all other species (e.g. "sp1 vs sp2"), and the Pearson correlation coefficient (r) was calculated (FIG. 9B). A heatmap was generated to summarize the Pearson correlation coefficients (FIG. 9C). Negative correlations were ignored.

A similar plot to FIG. 9B can be generated plotting the predicted hybridization energies against the predicted hybridization energies. This provides a predicted matrix of how well hybridization patterns are correlated between different species. This can be used as a preview (or as a predictor) of how the measured versus predicted correlation heatmap will appear after performing the experimental measurement. This can be useful for optimizing a capture polynucleotide panel for specificity before running the assay according to the present disclosure. A threshold can be set for one set of the predicted hybridization affinities where only hybridization affinities greater than this threshold (e.g. a change of Gibs free energy less than −7 kcal/mol) is considered. This would make the predicted versus predicted matrix more representative of the measured vsersus predicted matrix, where low affinity capture probe-amplicon interactions are not detected, or are detected but the signal does not correlate with binding energy below this threshold.

Figures 9D, 9E:
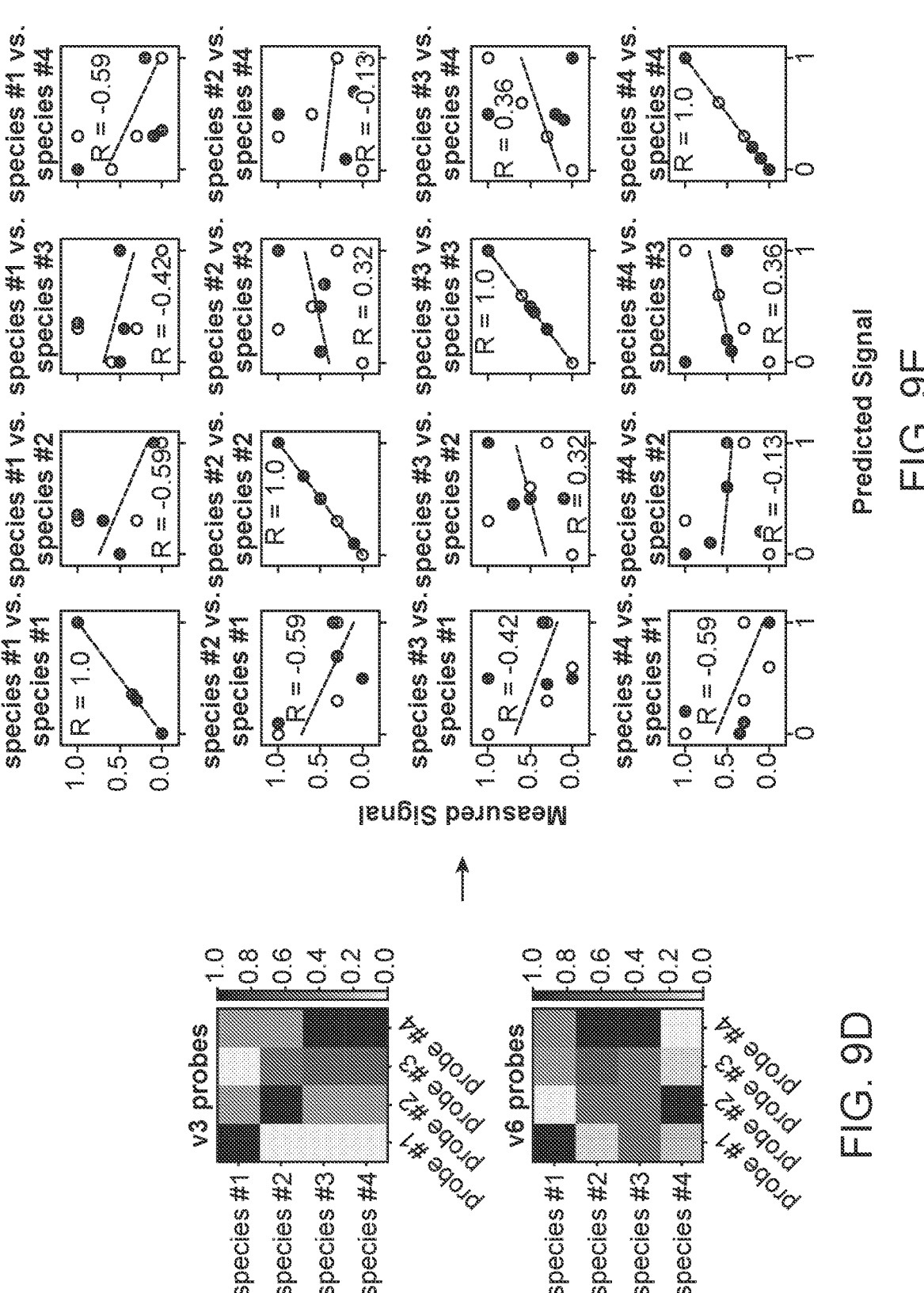
FIG. 9D shows a heatmap illustrating four species that bind with different affinities to four capture polynucleotides of the V3 (top) and V4 (bottom) region.
FIG. 9E shows illustrative examples of Pearson correlation coefficients (r) for the measured hybridization signal and predicted hybridization energies for both the V3 and V6 region.
Figure 9F:
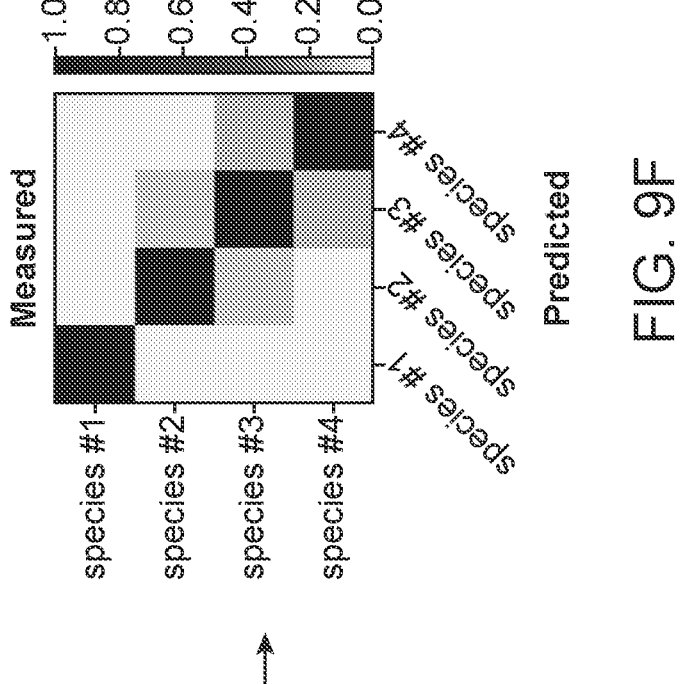
FIG. 9F shows a heatmap illustrating the Pearson correlation coefficients shown in FIG. 9E.

A similar analysis as described above was performed combining hybridization affinities for two different regions (V3 and V6 variable region amplicons from the 16S ribosomal DNA). A heatmap was generated to summarize the predicted hybridization affinities for different species with a model containing four species, where two of them are identical in V3 and two of them are identical in V6 (FIG. 9D). Correlations for each of the species considering V3 and V6 together were calculated and are shown in FIG. 9E. Combining V3 and V6 information resolves ambiguity in detecting species 2, 3, and 4 with only one variable region. A heatmap was generated to summarize the Pearson correlation coefficients for each of the species considering the combined measurements for V3 and V6 (FIG. 9F).

Figure 10A:
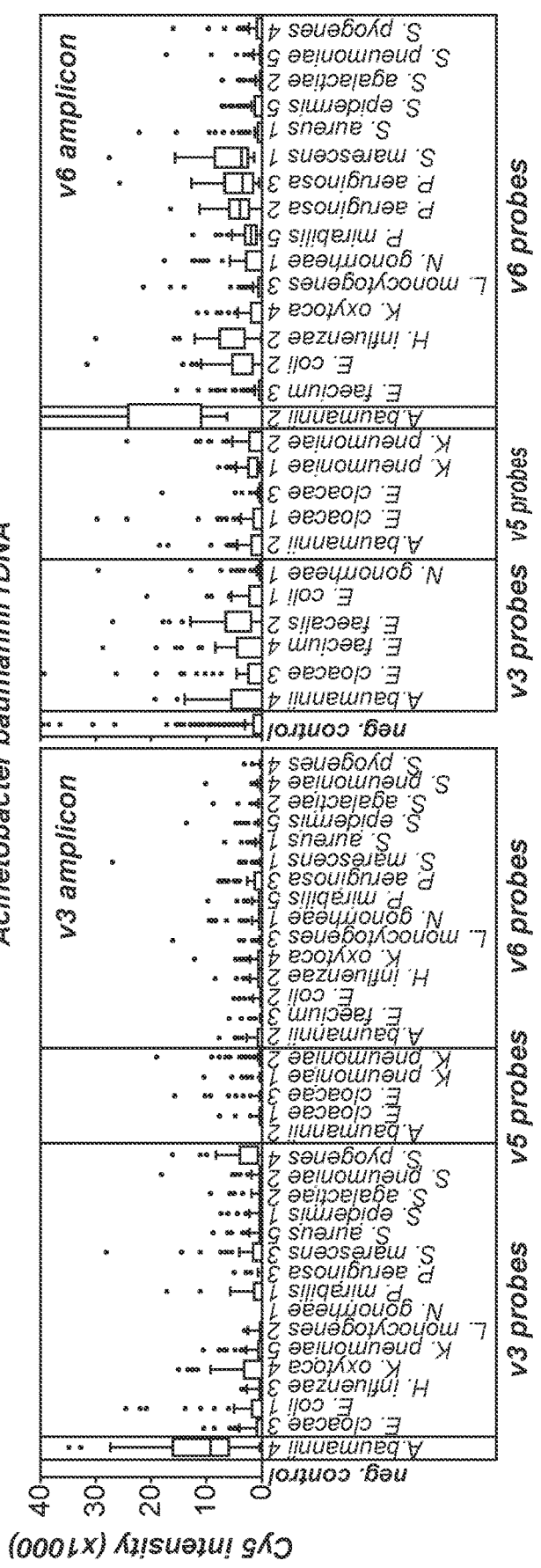
FIG. 10A shows the fluorescence signal intensity of microbeads reflecting the hybridization of *Acinetobacter baumannii* amplicons to different capture polynucleotides.

Example 6. The Assay According to the Present Disclosure Combined with a Pattern of Hybridization Analysis can Identify *Acinetobacter baumannii* in a Sample The assay according to the present disclosure was performed on *Acinetobacter baumannii*, targeting the V3 and V6 variable region, and the fluorescence signal from the beads was measured (FIG. 10A). The Gibbs free energy of hybridization was calculated for the amplicon of the V3 and V6 region of *Acinetobacter baumannii* binding to each capture polynucleotide in the panel (where the panel was comprised of 48 capture polynucleotides; see Table 7). This calculation was performed for all amplicons of all species in the panel.

Table 6 shows the targeted pathogens and the capture polynucleotide sequences used in the experiments presented in Examples 6-9.

TABLE 6

Targeted Pathogens in Examples 6-9
Species

*Acinetobacter baumannii*
*Haemophilus influenzae*
*Neisseria meningitidis*
*Pseudomonas aeruginosa*
*Enterobacter cloacae*
*Escherichia coli*
*Klebsiella oxytoca*
*Klebsiella pneumoniae*
*Proteus mirabilis*
*Serratia marcescens*
*Enterococcus faecalis*
*Enterococcus faecium*
*Listeria monocytogenes*
*Staphylococcus epidermidis*
*Staphylococcus aureus*
*Streptococcus agalactiae*
*Streptococcus pneumoniae*
*Streptococcus pyogenes*

TABLE 7

Sequences for Hybridization Capture Polynucleotides used in the experiments presented in Examples 6, 7, and 9.

| Description | Sequence | Variable region | SEQ ID NO: |
|---|---|---|---|
| v3_Aba_4_190815 | GCTTATTCTGCGAGTAACGTCCACTATCTCTAGGT | V3 | 175 |
| v3Ecl_3_190815 | GCGGGTAACGTCAATTGCTGCGGTTATT | V3 | 176 |
| v3Eco_1_190815 | GCGGGTAACGTCAATGAGCAAAGGTATTAACTTT | V3 | 177 |

TABLE 7-continued

Sequences for Hybridization Capture Polynucleotides used in the experiments
presented in Examples 6, 7, and 9.

| Description | Sequence | Variable region | SEQ ID NO: |
|---|---|---|---|
| v3Efa_4_190815 | GTCAGGGGACGTTCAGTTACTAACGT | V3 | 178 |
| v3Efa_2_190815 | GTCAAGGGATGAACAGTTACTCTCATCCTTGTT | V3 | 179 |
| v3Hin_3_190515 | TAGCCGGTGCTTCTTCTGTATTTAACGTCAATTTG | V3 | 180 |
| v3Kox_4_190515 | GGTGCTTCTTCTGCGGGTAACGTCAATGAATAAG | V3 | 181 |
| V3Kpn_5_190515 | GCGGGTAACGTCAATCGATGAGGTTATTAACC | V3 | 182 |
| v3Lmo_2_190515 | GGTTAGATACCGTCAAGGGACAAGCAGTTACTCTT | V3 | 183 |
| v3Pae_3_190515 | GTCAAAACAGCAAGGTATTAACTTACTGCCCTT | V3 | 184 |
| v3Pmi_1_190515 | GGGTATTAACCTTATCACCTTCCTCCCCGCTG | V3 | 185 |
| v3_Sag_2_190515 | GTCACTTGGTAGATTTTCCACTCCTACCAACGTT | V3 | 186 |
| v3_Sau_5_190515 | GATGTGCACAGTTACTTACACATATGT | V3 | 46 |
| v3_Sep_1_190515 | GTCAAGACGTGCATAGTTACTTACACATTTGTT | V3 | 187 |
| v3_Sma_3_190515 | GCGAGTAACGTCAATTGATGAGCGTATTAAGCTCA | V3 | 188 |
| v3Spn_2_190515 | GTCACAGTGTGAACTTTCCACTCTCACACTCGTT | V3 | 189 |
| v3_Spy_4_190515 | GTTGCCCCCATTGCCGAAGATT | V3 | 190 |
| v6Aba_2_190815 | GCACCTGTATCTAGATTCCCGAAGG | V6 | 24 |
| v6Eco_2_190815 | TGAAAACTTCCGTGGATGTCAAGACCAGGTAAGG | V6 | 191 |
| v6Efa_3_190815 | GAAGGGGAAGCTCTATCTCTAGAGTGGTCAAAGG | V6 | 192 |
| v6Hin_2_190815 | TGCAAACTTCTTAGGATGTCAAGAGTAGGTAAGG | V6 | 193 |
| v6Kox_4_190815 | AGCATCTCTGCTAAATTCTCTGGATGTCAAGAG | V6 | 194 |
| v6Lmo_3_190815 | CTCCAGAGTGGTCAAAGGATGTCAAGACCTGG | V6 | 195 |
| v6Pae_3_190815 | GGAAAGTTCTCAGCATGTCAAGGC | V6 | 18 |
| v6Pmi_5_190815 | TCCTCTATCTCTAAAGGATTCGCTGGATGTCAAG | V6 | 196 |
| v6Sag_2_190815 | GAAGAGAAAGCCTATCTCTAGGCCGGTCAGAAGG | V6 | 197 |
| v6Sau_1_190815 | GGGGAAGGCTCTATCTCTAGAGTTGTCAAAGGATG | V6 | 198 |
| v6Sep_5_190815 | GGGGAAAACTCTATCTCTAGAGGGGTCAGAGGATG | V6 | 199 |
| v6Sma_1_190815 | GGAAAGTTCTCTGGATGTCAAGAGTAGGTAAGG | V6 | 200 |
| v6Spn_5_190815 | GAAGGAAAACTCTATCTCTAGAGCGGTCAGAGGG | V6 | 201 |
| v6Spy_4_190815 | GAAGTAAAACTCTATCTCTAGAGCGGGCATCGGG | V6 | 202 |
| v5Aba_2_190815 | GCTGCGCCACTAAAGCCTCAAAGGC | V5 | 203 |
| v5Ecl_1_190815 | GGTCGATTTAACGCGTTAGCCTCCGGAAG | V5 | 204 |
| v5Eco_1_190815 | GGCGGTCGACTTAACGCGTTANNTCCGGAAG | V5 | 205 |
| v5Hin_2_190815 | GGCGGTCGATTTATCACGTTAGCTACGGG | V5 | 206 |
| v5Kox_4_190815 | AACGCGTTAGCTCCGGAAGCCACTC | V5 | 207 |
| v5Pae_1_190815 | GTTAGCTGCGCCACTAAGATCTCAAGGATC | V5 | 208 |
| v5Pmi_3_190815 | GAAGCCACGGTTCAAGACCACAACCTCTAAAT | V5 | 209 |
| v5Spn_1_190815 | GGAGTGCTTAATGCGTTAGCTACGGCACTAAA | V5 | 210 |
| v5Spy_1_190815 | GAGTGCTTAATGCGTTAGCTCCGGCACTAAG | V5 | 211 |

TABLE 8

Sequences with 5' amine modifications and carbon and oligo spacers for
Hybridization Capture Polynucleotides used in the experiments presented in
Example 6, 7, and 9.

| Description | Sequence | SEQ ID NO: |
|---|---|---|
| v3_Aba_4_190815 | /5AmMC12/TTTTTTTGCTTATTCTGCGAGTAACGTCCACTATCTCTAGGT | 212 |
| v3Ecl_3_190815 | /5AmMC12/TTTTTTTGCGGGTAACGTCAATTGCTGCGGTTATT | 213 |
| v3Eco_1_190815 | /5AmMC12/TTTTTTTGCGGGTAACGTCAATGAGCAAAGGTATTAACTTT | 214 |
| v3Efa_4_190815 | /5AmMC12/TTTTTTTGTCAGGGGACGTTCAGTTACTAACGT | 215 |
| v3Efa_2_190815 | /5AmMC12/TTTTTTTGTCAAGGGATGAACAGTTACTCTCATCCTTGTT | 216 |
| v3Hin_3_190515 | /5AmMC12/TTTTTTTTAGCCGGTGCTTCTTCTGTATTTAACGTCAATTTG | 217 |
| v3Kox_4_190515 | /5AmMC12/TTTTTTTGGTGCTTCTTCTGCGGGTAACGTCAATGAATAAG | 218 |
| V3Kpn_5_190515 | /5AmMC12/TTTTTTTGCGGGTAACGTCAATCGATGAGGTTATTAACC | 219 |
| v3Lmo_2_190515 | /5AmMC12/TTTTTTTGGTTAGATACCGTCAAGGGACAAGCAGTTACTCTT | 220 |
| v3Pae_3_190515 | /5AmMC12/TTTTTTTGTCAAAACAGCAAGGTATTAACTTACTGCCCTT | 221 |
| v3Pmi_1_190515 | /5AmMC12/TTTTTTTGGGTATTAACCTTATCACCTTCCTCCCCGCTG | 222 |
| v3_Sag_2_190515 | /5AmMC12/TTTTTTTGTCACTTGGTAGATTTTCCACTCCTACCAACGTT | 223 |
| v3_Sau_5_190515 | /5AmMC12/TTTTTTTGATGTGCACAGTTACTTACACATATGT | 45 |
| v3_Sep_1_190515 | /5AmMC12/TTTTTTTGTCAAGACGTGCATAGTTACTTACACATTTGTT | 224 |
| v3_Sma_3_190515 | /5AmMC12/TTTTTTTGCGAGTAACGTCAATTGATGAGCGTATTAAGCTCA | 225 |
| v3Spn_2_190515 | /5AmMC12/TTTTTTTGTCACAGTGTGAACTTTCCACTCTCACACTCGTT | 226 |
| v3_Spy_4_190515 | /5AmMC12/TTTTTTTGTTGCCCCCATTGCCGAAGATT | 227 |
| v6Aba_2_190815 | /5AmMC12/TTTTTTTGCACCTGTATCTAGATTCCCGAAGG | 23 |
| v6Eco_2_190815 | /5AmMC12/TTTTTTTTGAAAACTTCCGTGGATGTCAAGACCAGGTAAGG | 228 |
| v6Efa_3_190815 | /5AmMC12/TTTTTTTGAAGGGGAAGCTCTATCTCTAGAGTGGTCAAAGG | 229 |
| v6Hin_2_190815 | /5AmMC12/TTTTTTTTGCAAACTTCTTAGGATGTCAAGAGTAGGTAAGG | 230 |
| v6Kox_4_190815 | /5AmMC12/TTTTTTTAGCATCTCTGCTAAATTCTCTGGATGTCAAGAG | 231 |
| v6Lmo_3_190815 | /5AmMC12/TTTTTTTCTCCAGAGTGGTCAAAGGATGTCAAGACCTGG | 232 |
| v6Pae_3_190815 | /5AmMC12/TTTTTTTGGAAAGTTCTCAGCATGTCAAGGC | 233 |
| v6Pmi_5_190815 | /5AmMC12/TTTTTTTTCCTCTATCTCTAAAGGATTCGCTGGATGTCAAG | 234 |
| v6Sag_2_190815 | /5AmMC12/TTTTTTTGAAGAGAAAGCCTATCTCTAGGCCGGTCAGAAGG | 235 |
| v6Sau_1_190815 | /5AmMC12/TTTTTTTGGGGAAGGCTCTATCTCTAGAGTTGTCAAAGGATG | 236 |
| v6Sep_5_190815 | /5AmMC12/TTTTTTTGGGGAAAACTCTATCTCTAGAGGGGTCAGAGGATG | 237 |
| v6Sma_1_190815 | /5AmMC12/TTTTTTTGGAAAGTTCTCTGGATGTCAAGAGTAGGTAAGG | 238 |
| v6Spn_5_190815 | /5AmMC12/TTTTTTTGAAGGAAAACTCTATCTCTAGAGCGGTCAGAGGG | 239 |
| v6Spy_4_190815 | /5AmMC12/TTTTTTTGAAGTAAAACTCTATCTCTAGAGCGGGCATCGGG | 240 |
| v5Aba_2_190815 | /5AmMC12/TTTTTTTGCTGCGCCACTAAAGCCTCAAAGGC | 241 |
| v5Ecl_1_190815 | /5AmMC12/TTTTTTTGGTCGATTTAACGCGTTAGCCTCCGGAAG | 242 |
| v5Eco_1_190815 | /5AmMC12/TTTTTTTGGCGGTCGACTTAACGCGTTANNTCCGGAAG | 243 |
| v5Hin_2_190815 | /5AmMC12/TTTTTTTGGCGGTCGATTTATCACGTTAGCTACGGG | 244 |
| v5Kox_4_190815 | /5AmMC12/TTTTTTTAACGCGTTAGCTCCGGAAGCCACTC | 245 |
| v5Pae_1_190815 | /5AmMC12/TTTTTTTGTTAGCTGCGCCACTAAGATCTCAAGGATC | 246 |

TABLE 8-continued

Sequences with 5' amine modifications and carbon and oligo spacers for
Hybridization Capture Polynucleotides used in the experiments presented in
Example 6, 7, and 9.

| Description | Sequence | SEQ ID NO: |
|---|---|---|
| v5Pmi_3_190815 | /5AmMC12/TTTTTTTGAAGCCACGGTTCAAGACCACAACCTCTAAAT | 247 |
| v5Spn_1_190815 | /5AmMC12/TTTTTTTGGAGTGCTTAATGCGTTAGCTACGGCACTAAA | 248 |
| v5Spy_1_190815 | /5AmMC12/TTTTTTTGAGTGCTTAATGCGTTAGCTCCGGCACTAAG | 249 |

Figure 10B:
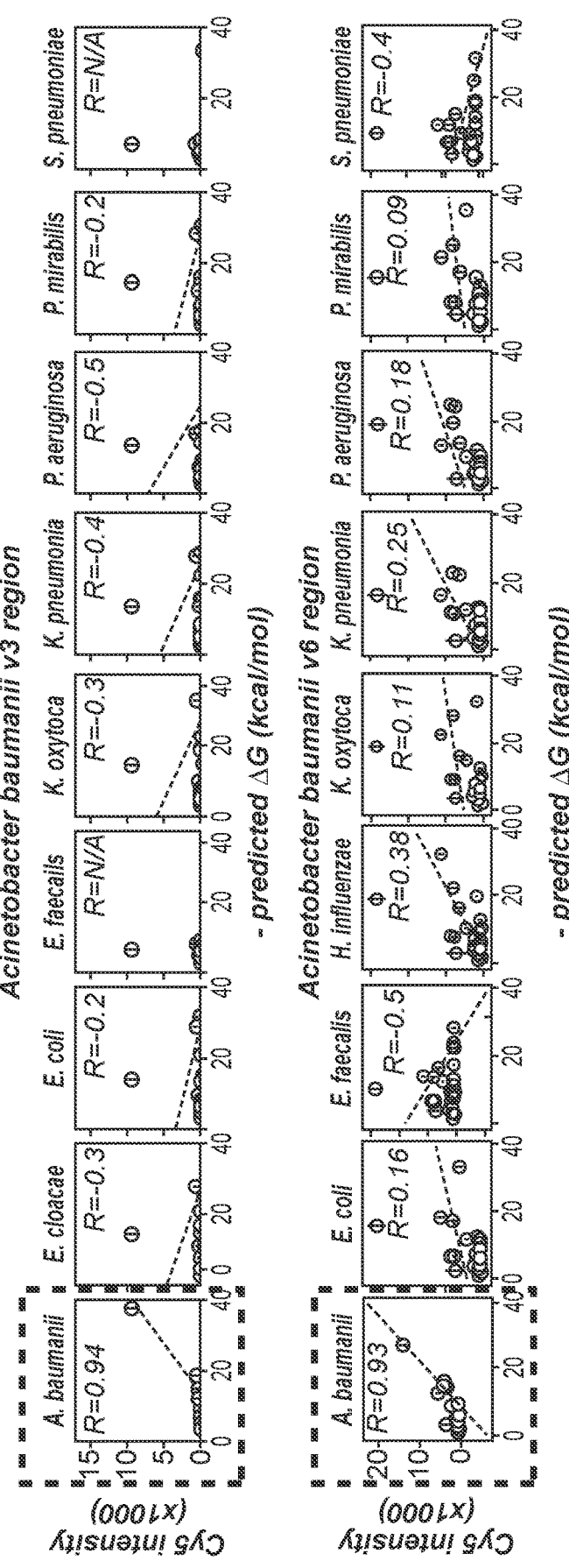
FIG. 10B shows Pearson correlations (R) of measured hybridization signal intensities with the predicted hybridization energies for V3 (top row) and V6 (bottom row) *Acinetobacter baumannii* amplicons against a panel of capture polynucleotides.

After performing the assay according to the present disclosure on a sample (this could be a sample where the pathogen is unknown), the Pearson correlation coefficient for the measured hybridization signal and the predicted hybridization energies based on the Gibbs free energy was calculated. This calculation was performed for every pathogen amplicon the panel was designed to detect. As an example, FIG. 10B illustrates the Pearson correlation of measured hybridization signal intensities with the predicted hybridization energies that was calculated for V3 (top row) and V6 (bottom row) *Acinetobacter baumannii* amplicons. Each dot represents the median hybridization signal intensity of all beads of that spectral code, and the error bars are standard errors of them mean. The cognate capture polynucleotide for each amplicon shows the strongest hybridization signal, however there is hybridization signal on other beads, the intensity of which correlates with predicted hybridization affinity. The highlighted plots on the left show the correlations of hybridization measurements for *Acinetobacter baumanii* with the predicted hybridization energies for the *Acinetobacter baumanii* V3 or V6 amplicon against all probes. The plots to the right of these show how well the measurements of *Acinetobacter baumanii* correlate with the predicted hybridization affinities to the capture polynucleotide for V3 or V6 amplicons from different species. By analyzing which pathogen amplicon is best correlated (the highest Pearson correlation coefficient, R) with the measured unknown pathogen sample, it can be determined which pathogen (from the panel) is most likely present in the sample. In this analysis, a threshold was applied to omit low affinity capture polynucleotides from correlation analyses. Specifically, the correlation analysis was performed using only capture polynucleotides predicted to bind to the target amplicon with a Gibbs free energy less than −10 kcal/mol. Negative Pearson correlation coefficients were omitted from consideration during pathogen identification.

The specificity of the assay when using this above described correlation analysis can be assessed by analyzing the area under a receiver operating characteristic curve (AUROC). This is generated by setting a threshold of the Pearson correlation coefficient (R) to call a species (or amplicon) present and analyzing how many (or what fraction of) species would be detected as true positives or false positives. In particular, the curve is generated by scanning this threshold through all possible values for R (0 to 1), and plotting the fraction of true positive and false positive detected species at each detection threshold.

Figure 11:
FIG. 11. shows a heatmap displaying the Gibbs free energy of hybridization for distinguishing groups of bacteria.

Example 7. Using the Assay of the Present Disclosure for Targeting Species for which the Panel was not Designed Hybridization affinities, and subsequent capture polynucleotide panel hybridization patterns, can be predicted for species for which the capture polynucleotide were not originally designed for. This allows testing for species that were not originally targeted in the capture polynucleotide panel design. A heatmap was generated displaying the Gibbs free energy of hybridization (FIG. 11). The heatmap shows the hybridization energies for each capture polynucleotide (y-axis) plotted against all species (x-axis). In this case, the energy of the V6 amplicon binding to the capture polynucleotide was calculated, and the energy of the V6 amplicon hybridizing with other V6 amplicons was subtracted and multiplied by −1. While the existing capture polynucleotides may not be able to clearly distinguish all bacteria, it is possible to distinguish groups of bacteria, for example based on a similar sequence or phylogeny.

Figures 12A, 12B:
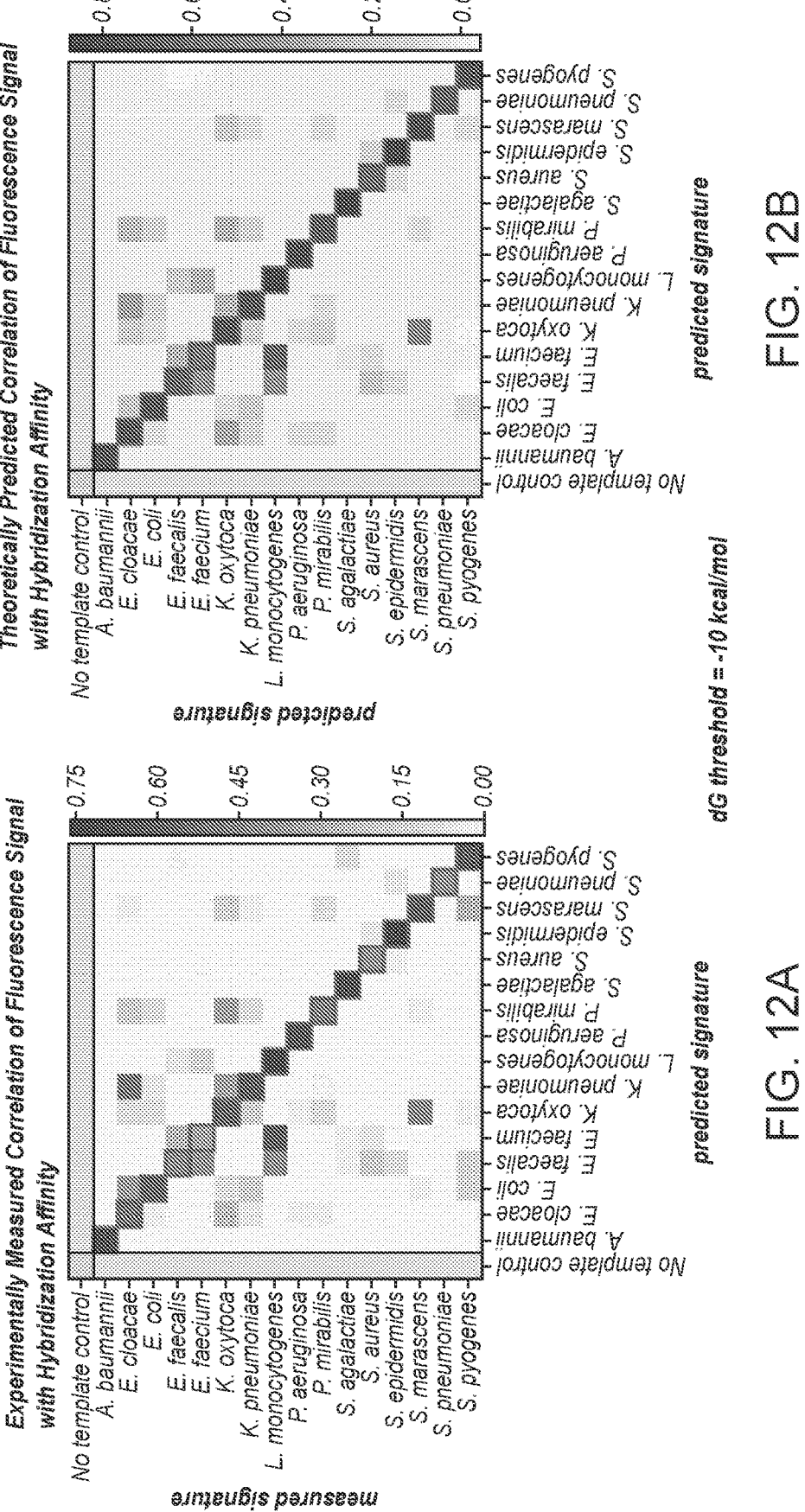
FIG. 12A and FIG. 12C show summary heatmaps of correlations between measured hybridization signal intensity and predicted hybridization affinity.
FIG. 12B and FIG. 12D show prediction matrices for the probes used for experiments shown in FIG. 12A and FIG. 12C, respectively.
Figures 12C, 12D:

Example 8. Hybridization Pattern Analysis for the Selection of an Optimal Panel of Capture Polynucleotide The correlation analysis as described above was used to select an optimal panel of capture polynucleotides. Two different panels were tested. For an amplicon of a given species (here an amplicon of the V6 region of *Acinetobacter baumannii*), the Gibbs free energy of hybridization was calculated for the amplicon binding to each capture polynucleotide in the panel (where the panel is comprised of a plurality of probes). This calculation was done for all amplicons of all species the panel was designed to detect. To assess the predicted specificity of a panel, the Pearson correlation coefficient was calculated to measure the correlation of the predicted hybridization patterns for a given amplicon, with the predicted hybridization patterns for all other amplicons, as well as itself (FIG. 12). Summary heatmaps of correlations between measured hybridization signal and predicted hybridization affinity were generated for each of the panels (FIG. 12A and FIG. 12C). The scale bar represents Pearson correlation coefficients (R) and frames highlight the cognate pairing of measured and predicted species. The "dG threshold" is the value of AG (the Gibbs free energy) for a capture polynucleotide:amplicon hybridization for which the capture polynucleotides with lower affinity are omitted from the Pearson Correlation analysis. This analysis was performed using only capture polynucleotides predicted to bind to the target amplicon with a Gibbs free energy less than −10 kcal/mol. Negative Pearson correlation coefficients were omitted.

Prediction matrices were then generated, showing that the two panels of capture polynucleotides present different hybridization patterns, with one of the panels (FIG. 12D) exhibiting improved discrimination of species compared to the other panel (FIG. 12B). Comparison of the heatmap illustrating the measured hybridization signature vs. predicted hybridization signature correlations with the heatmap illustrating the predicted hybridization signature vs. predicted hybridization signature correlations reveals that the measured panel performs similar to what is predicted.

Figures 13A, 13B, 13C:
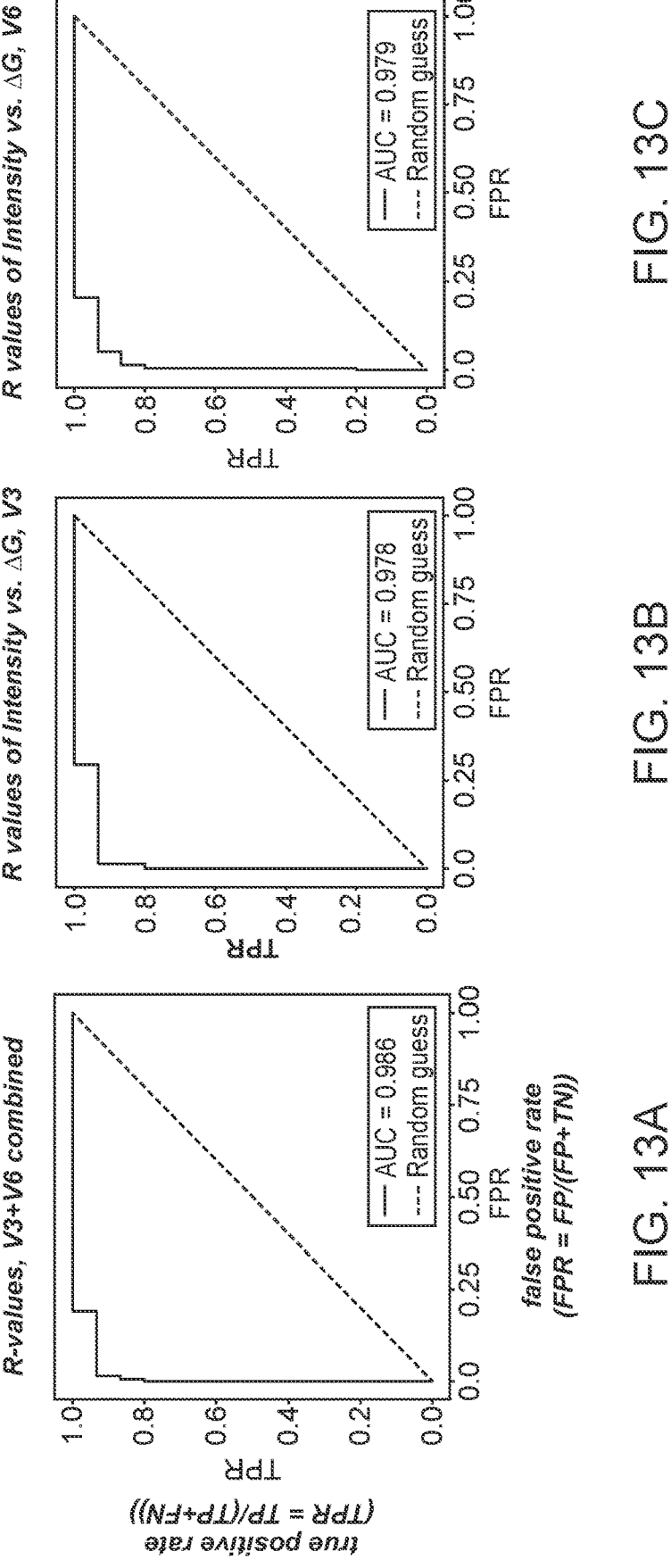
FIG. 13A shows the area under a receiver operating characteristic curve (AUROC) analysis for the combined V3 and V6 correlations.
FIG. 13B shows the AUROC analysis for the V3 amplicons.
FIG. 13C shows the AUROC analysis for the V6 amplicons.

The performance of the assay was then evaluated for a particular panel of capture polynucleotides. The Pearson correlation coefficient values were used to generate a receiver operating characteristic curve (AURAC) by setting a threshold of the Pearson correlation coefficient (R) to call a species (or amplicon) present and analyzing how many (or what fraction of) species would be detected as true positives or false positives (FIG. 13). The curve was generated by scanning this threshold through all possible values for R (0 to 1), and plotting the fraction of true positive and false positive detected species at each detection threshold. This was done for the V3 and V6 amplicons separately (FIG. 13B and FIG. 13C, respectively), or from the combined V3 and V6 correlations (FIG. 13A). The area under the receiver operating characteristic curve (AUROC) was calculated as a metric of specificity. An optimal capture polynucleotide panel can be found by iteratively creating panels of capture polynucleotides from the multitude of candidate probes and maximizing the predicted AUROC.

TABLE 9

Sequences with 5' amine modifications and carbon and oligo spacers for
Hybridization Probes used in the experiments presented in Example 8.

| Description | Sequence | SEQ ID NO: |
|---|---|---|
| v6Acinetobacter_baumannii_28 | /5AmMC12/TTTTTTTGTTTCTAGTATGTCAAGGCCAGGTAA | 250 |
| v6Enterobacter_cloacae_7 | /5AmMC12/TTTTTTTAATCCATCTCTGGAAAGTTCTGTG | 251 |
| v6Enterococcus_faecalis_0 | /5AmMC12/TTTTTTTTCCCCGAAGGGAAAGCTCTA | 252 |
| v6Enterococcus_faecium_2 | /5AmMC12/TTTTTTTCTTTGCCCCCGAAGGGG | 253 |
| v6Escherichia_coli_0 | /5AmMC12/TTTTTTTCATTCTCATCTCTGAAAACTTCCGTG | 254 |
| v6Haemophilus_influenzae_41 | /5AmMC12/TTTTTTTCATCTCTGCAAACTTCTTAGGATGTC | 255 |
| v6Klebsiella_oxytoca_24 | /5AmMC12/TTTTTTTCAAAGCATCTCTGCTAAATTCTCTGG | 256 |
| v6Listeria_monocytogenes_0 | /5AmMC12/TTTTTTTGTCTCCAGAGTGGTCAAAGGATG | 257 |
| v6Proteus_mirabilis_8 | /5AmMC12/TTTTTTTCACTCCTCTATCTCTAAAGGATTCGC | 258 |
| v6Pseudomonas_aeruginosa_0 | /5AmMC12/TTTTTTTATCTCTGGAAAGTTCTCAGCATGTC | 259 |
| v6Serratia_marcescens_0 | /5AmMC12/TTTTTTTGAAAGTTCTCTGGATGTCAAGAGTAG | 260 |
| v6Staphylococcus_aureus_23 | /5AmMC12/TTTTTTTAGGCTCTATCTCTAGAGTTGTCAAAG | 261 |
| v6Staphylococcus_epidermidis_11 | /5AmMC12/TTTTTTTCTATCTCTAGAGGGGTCAGAGGAT | 262 |
| v6Streptococcus_agalactiae_11 | /5AmMC12/TTTTTTTGTCACTTCTGCTCCGAAGAGAAA | 263 |
| v6Streptococcus_pneumoniae_10 | /5AmMC12/TTTTTTTTCTGTCCCGAAGGAAAACTCTATCT | 264 |
| v6Streptococcus_pyogenes_29 | /5AmMC12/TTTTTTTCCGATGTACCGAAGTAAAACTCTATC | 265 |
| v3_Acinetobacter_baumannii_106 | /5AmMC12/TTTTTTTACGTCCACTATCTCTAGGTATTAACT | 266 |
| v3Enterobacter_cloacae_8 | /5AmMC12/TTTTTTTCGGTTATTAACCACAACACCTTCC | 267 |
| v3Enterococcus_faecalis_29 | /5AmMC12/TTTTTTTGTTCAGTTACTAACGTCCTTGTTCTT | 268 |
| v3Enterococcus_faecium_17 | /5AmMC12/TTTTTTTGTCAAGGGATGAACAGTTACTCTCAT | 269 |
| v3Escherichia_coli_40 | /5AmMC12/TTTTTTTGGTATTAACTTTACTCCCTTCCTCCC | 270 |
| v3Haemophilus_influenzae_153 | /5AmMC12/TTTTTTTTTCCTCAATACCGAAAGAACTTTACA | 271 |
| v3Klebsiella_oxytoca_56 | /5AmMC12/TTTTTTTGAATAAGGTTATTAACCTCACTCCCT | 272 |
| v3Klebsiella_pneumoniae_20 | /5AmMC12/TTTTTTTGATGAGGTTATTAACCTTAACGCCTT | 273 |
| v3Listeria_monocytogenes_102 | /5AmMC12/TTTTTTTGCAGTTACTCTTATCCTTGTTCTTCT | 274 |
| v3Proteus_mirabilis_64 | /5AmMC12/TTTTTTTAGGGTATTAACCTTATCACCTTCCTC | 275 |
| v3Pseudomonas_aeruginosa_45 | /5AmMC12/TTTTTTTTCAAAACAGCAAGGTATTAACTTACT | 276 |
| v3Serratia_marcescens_17 | /5AmMC12/TTTTTTTAACGTCAATTGATGAGCGTATTAAGC | 277 |
| v3Staphylococcus_aureus_40 | /5AmMC12/TTTTTTTGTCAAGATGTGCACAGTTACTTACAC | 278 |

TABLE 9-continued

Sequences with 5' amine modifications and carbon and oligo spacers for
Hybridization Probes used in the experiments presented in Example 8.

| Description | Sequence | SEQ ID NO: |
|---|---|---|
| v3Staphylococcus_epidermidis_36 | /5AmMC12/TTTTTTTGACGTGCATAGTTACTTACACATTTG | 59 |
| v3Streptococcus_agalactiae_4 | /5AmMC12/TTTTTTTTAGATTTTCCACTCCTACCAACGTTC | 279 |
| v3Streptococcus_pneumoniae_14 | /5AmMC12/TTTTTTTCACTCTCACACTCGTTCTTCTCTTA | 280 |
| v3Streptococcus_pyogenes_13 | /5AmMC12/TTTTTTTCCACCATCATTCTTCTCTAACAACAG | 281 |

Figure 14:
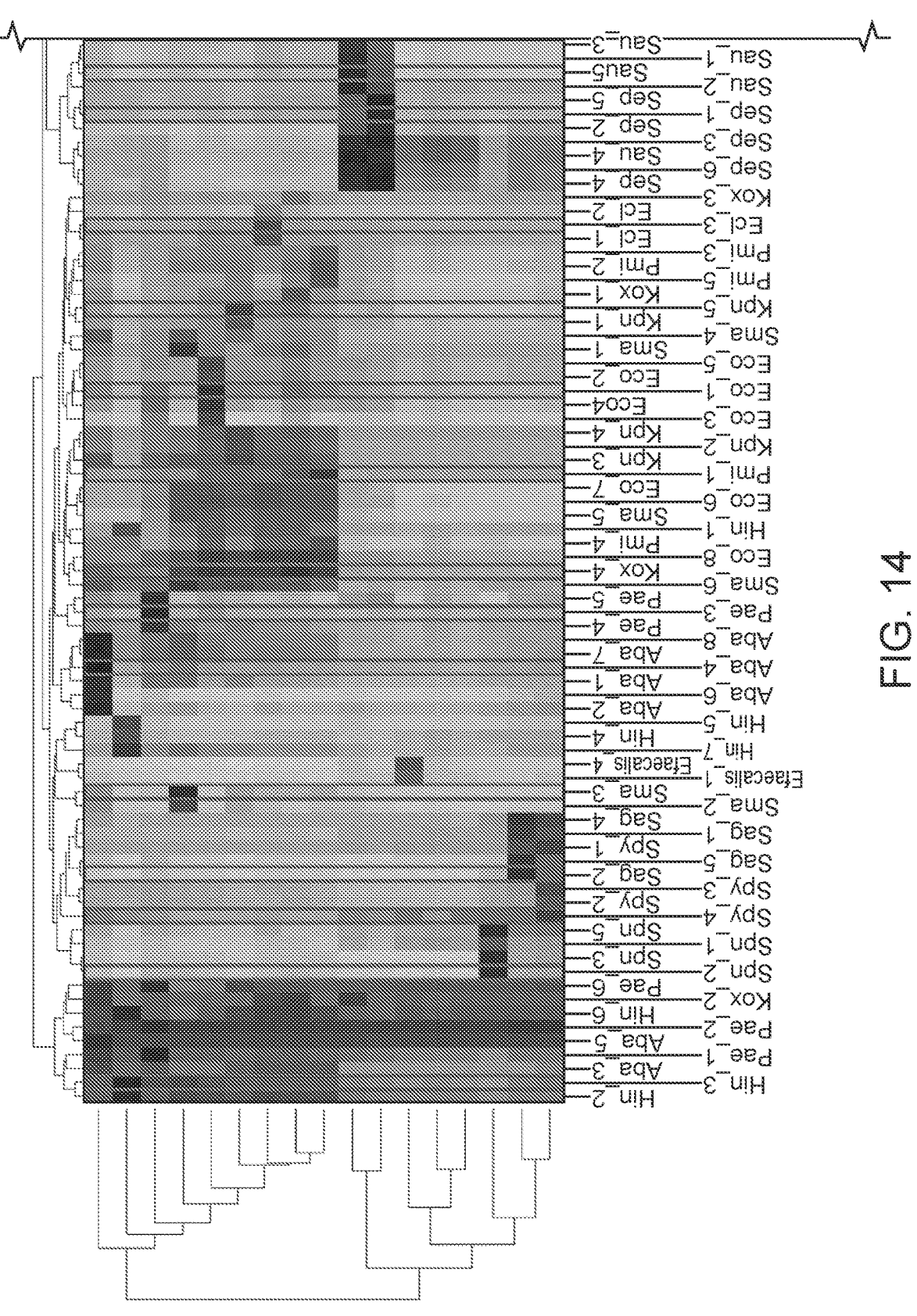
FIG. 14 shows clustering of probe candidates (columns) and bacterial species (rows) based on probe-to-amplicon hybridization affinities.
Figure 14:
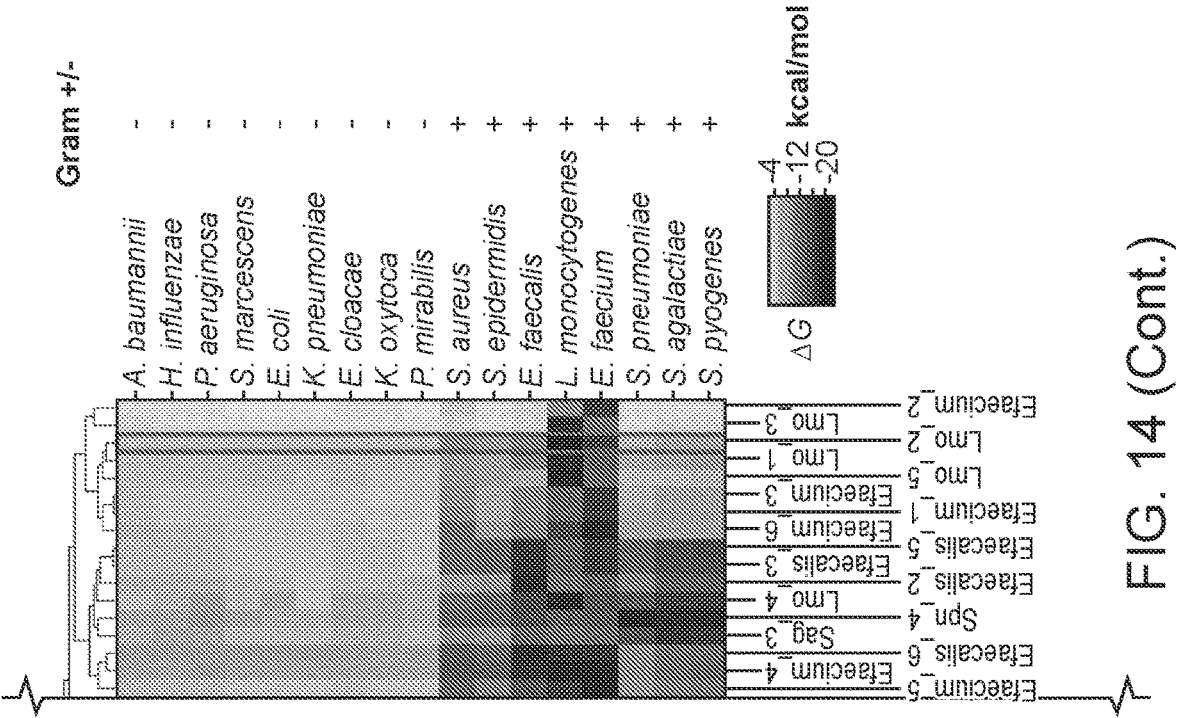

Example 9. Clustering of Capture Polynucleotide Candidates and Bacterial Species Based on Hybridization Affinities Capture polynucleotide-to-amplicon hybridization affinities were used to cluster capture polynucleotide candidates and bacterial species into genus and Gram stain status (positive or negative). A heatmap was generated illustrating the clustering (FIG. 14). The heatmap shows the hybridization affinities for each capture polynucleotide (x-axis). Capture polynucleotides may be selected for species specificity or broader categorization such as Gram status using hierarchical clustering. For example, if a capture polynucleotide is shown to bind to all bacteria of a particular Gram type (i.e., Gram positive or Gram negative), it may be selected as a probe to test for Gram type. Similarly, if a capture polynucleotide binds to all bacteria of the Viridians group, it may be selected as a more general probe for bacteria species in this group.

Although the foregoing has been described in some detail by way of illustration and example for purposes of clarity and understanding, one of skill in the art will appreciate that certain changes and modifications can be practiced within the scope of the appended claims. In addition, each reference provided herein is incorporated by reference in its entirety to the same extent as if each reference was individually incorporated by reference.

---

INFORMAL SEQUENCE LISTING

SEQ ID NO: 1
/A647/GTGCCAGCMGCCGCGGTAA

SEQ ID NO: 2
Phos/GGACTACHVGGGTWTCTAAT

SEQ ID NO: 3
GTGCCAGCMGCCGCGGTAA

SEQ ID NO: 4
GGACTACHVGGGTWTCTAAT

SEQ ID NO: 5
/A647/TGGAGCATGTGGTTTAATTCGA

SEQ ID NO: 6
TGGAGCATGTGGTTTAATTCGA

SEQ ID NO: 7
Phos/AGCTGACGACANCCATGCA

SEQ ID NO: 8
AGCTGACGACANCCATGCA

SEQ ID NO: 9
/A647/CCACACTCCTACGGGAGGCAG

---

-continued

INFORMAL SEQUENCE LISTING

SEQ ID NO: 10
CCAGACTCCTACGGGAGGCAG

SEQ ID NO: 11
/Phos/CGTATTACCGCGGCTGCTG

SEQ ID NO: 12
CGTATTACCGCGGCTGCTG

SEQ ID NO: 13
/5AmMC12/
TTTTTTTTCTAGAGTTGTCAAAGGATGTCAAGATTTGGTAAG

SEQ ID NO: 14
*S. aureus*
CTAGAGTTGTCAAAGGATGTCAAGATTTGGTAAG

SEQ ID NO. 15
/5AmMC12/TTTTTTTTACCTGTGTCTGAGTTCCCGAAGG

SEQ ID NO: 16
*P. aeruginosa*
ACCTGTGTCTGAGTTCCCGAAGG

SEQ ID NO: 17
/5AmMC12/TTTTTTTTGGAAAGTTCTCAGCATGTCAAGGC

SEQ ID NO: 18
*P. aeruginosa*
GGAAAGTTCTCAGCATGTCAAGGC

SEQ ID NO: 19
/5AmMC12/TTTTTTTGCCGTATTAACTAAATCCTCCTCGCTTAAAG

SEQ ID NO: 20
*A. baumannii*
GCCGTATTAACTAAATCCTCCTCGCTTAAAG

SEQ ID NO: 21
/5AmMC12/TTTTTTTTGGAAAGTTTCTAGTATGTCAAGGCCAGG

SEQ ID NO: 22
*A. bamannii*
GGAAAGTTTCTAGTATGTCAAGGCCAGG

SEQ ID NO 23
/5AmMC12/TTTTTTTGCACCTGTATCTAGATTCCCGAAGG

SEQ ID NO: 24
*A. baumannii*
GCACCTGTATCTAGATTCCCGAAGG

SEQ ID NO: 25
/5AmMC12/TTTTTTTTGCTAAGTTCTCTGGATGTCAAGAGTAGG

SEQ ID NO: 26
*E. eloaecae*
GCTAAGTTCTCTGGATGTCAAGAGTAGG

61

-continued

---
INFORMAL SEQUENCE LISTING
---

SEQ ID NO: 27
/5AmMC12/TTTTTTTTGACCTGGTAAGGTTCTTTCGCGTTG

SEQ ID NO: 28
*E. faecium*
GACCTGGTAAGGTTCTTTCGCGTTG

SEQ ID NO: 29
/5AmMC12/TTTTTTTTAGAGTGGTCAAAGGATGTCAAGA

SEQ ID NO: 30
*E. faecium*
AGAGTGGTCAAAGGATGTCAAGA

SEQ ID NO: 31
/5AmMC12/TTTTTTTTGTCTCACAGTTCCCGAAGGCA

SEQ ID NO: 32
*K. pneumoniae*
GTCTCACAGTTCCCGAAGGCA

SEQ ID NO: 33
/5AmMC12/TTTTTTTTGGAAAGTTCTGTGGATGTCAAGA

SEQ ID NO: 34
*K. pneumoniae*
GGAAAGTTCTGTGGATGTCAAGA

SEQ ID NO.35
/5AmMC12/TTTTTTTGTCACTCTGTCCCCCGAAGG

SEQ ID NO 36
*S. epidermis*
GTCACTCTGTCCCCCGAAGG

SEQ ID NO: 37
/5AmMC12/TTTTTTTGAGGGGTCAGAGGATGTCAAGATTTG

SEQ ID NO: 38
*S. epidermis*
GAGGGGTCAGAGGATGTCAAGATTTG

SEQ ID NO: 39
/5AmMC12/TTTTTTTTGTCACCTCTGTCCCGAAGGAAA

SEQ ID NO: 40
*S. pneumoniae*
GTCACCTCTGTCCCGAAGGAAA

SEQ ID NO: 41
/5AmMC12/TTTTTTTTAGAGCGGTCAGAGCGATGTCAAG

SEQ ID NO: 42
*S. pneumoniae*
AGAGCGGTCAGAGGGATGTCAAG

SEQ ID NO: 43
/5AmMC12/TTTTTTTGAGCAAAGGTATTAACTTTACTCCCTTcc

SEQ ID NO: 44
*E. coli*
GAGCAAAGGTATTAACTTTACTCCCTTCC

SEQ ID NO: 45
/5AmMC12/TTTTTTTGATGTGCACAGTTACTTACACATATGT

SEQ ID NO: 46
*S. aureus*
GATGTGCACAGTTACTTACACATATGT

SEQ ID NO: 47
/5AmMC12/TTTTTTTGTATTAACTTACTGCCCTTCCTCCCAAC

SEQ ID NO: 48
*P. aeruginosa*
GTATTAACTTACTGCCCTTCCTCCCAAC

62

-continued

---
INFORMAL SEQUENCE LISTING
---

SEQ ID NO: 49
/5AmMC12/TTTTTTTCTATCTCTAGGTAGCCGTATTAACTAAA

SEQ ID NO: 50
*A. baumannii*
CTATCTCTAGGTAGCCGTATTAACTAAA

SEQ ID NO: 51
/5AmMC12/TTTTTTTAGGGATGAACAGTTACTCTCATCCT

SEQ ID NO: 52
*E. eloaecae*
AGGGATGAACAGTTACTCTCATCCT

SEQ ID NO: 53
/5AmMC12/TTTTTTTCGGCAGGGTTATTAACCCTGTCGC

SEQ ID NO: 54
*E. faecium*
CGGCAGGGTTATTAACCCTGTCGC

SEQ ID NO: 55
/5AmMC12/TTTTTTTTCGACAAGGTTATTAACCTTATCG

SEQ ID NO: 56
*K. pneumoniae*
CGACAAGGTTATTAACCTTATCG

SEQ ID NO: 57
/5AmMC12/TTTTTTTCGGCCGCCGATATTGGCAACGGCCTT

SEQ ID NO: 58
*N. gonorrhoeae*
CGGCCGCCGATATTGGCAACGGCCTT

SEQ ID NO: 59
/5AmMC12/TTTTTTTGACGTGCATAGTTACTTACACATTTG

SEQ ID NO: 60
*S. epidermis*
GACGTGCATAGTTACTTACACATTTG

SEQ ID-NO: 61
/5AmMC12/TTTTTTTCAGTGTGAACTTTCCACTCTCACACTC

SEQ ID NO: 62
*S. pneumoniae*
CAGTGTGAACTTTCCACTCTCACACTC

SEQ ID NO: 63
GGACTACAGGGGTATCTAATCCCTTTTG

SEQ ID NO: 64
GGTGACAGGGGTTACAATCCGAG

SEQ ID NO: 65
GCGTTGCACCATCAGGGTTT

SEQ ID NO: 66
CGGCTTCATGCAGTCGAGTTG

SEQ ID NO: 67
CAGTGTACTCCGCTCCGAAGAG

SEQ ID NO: 68
AGTAACTCCGAACAACGCTTGC

SEQ ID NO: 69
GAACTGTGGCTGGGTTTGATGAGATT

SEQ ID NO: 70
CATGCAGGCGAGTTTCAGCC

SEQ ID NO: 71
GTTTCGCTCCCCTTTGTCCCAA

INFORMAL SEQUENCE LISTING

SEQ ID NO: 72
GTCAATTCATTTGAGTTTTAACCTTGCG

SEQ ID NO: 73
AGCTCGCCAGTTTTGGATGCAG

SEQ ID NO: 74
AGTCGACATCGTTTACGGCGTG

SEQ ID NO: 75
GAACTGAGATGGCTTTTGGAGATTCG

SEQ ID NO: 76
GAGCCAGGATCAAACTCTCAGGTTT

SEQ ID NO: 77
GTCTGGCCGACATCGTTTACGG

SEQ ID NO: 78
TTAGCTTTTGTAGCCTTTTTCCCTGCTG

SEQ ID NO: 79
CGAACTCGAGTTTTGCAGTATCTAAAGC

SEQ ID NO: 80
AGGAATTCCGCTTGCTTTTCCCG

SEQ ID NO: 81
CAGTTACTAGTTTTACCCTAGGCAGC

SEQ ID NO: 82
GAACTGAGATAGTGTTTAAGGGATTCGC

SEQ ID NO: 83
ACGTAGAAGGGTTTATTCCCAAACAAAA

SEQ ID NO: 84
TACGACCGGTTTTTCGGGATTGG

SEQ ID NO: 85
ATGTCAAAGGTGGGTAAGGTTTTTCG

SEQ ID NO: 86
GACTACGACCGGTTTTTCGGGATTG

SEQ ID NO: 87
GATCGCTCCCTTTTACCTCTCGG

SEQ ID NO: 88
GGTAAGGTTCTTCGGTTTGCATCGAATT

SEQ ID NO: 89
GTACTCCAGTCCGACGGTTTCG

SEQ ID NO: 90
TGCAGCACCTGTGTTTAGGTT

SEQ ID NO: 91
GTTCTAGCAAGCTAGCACTCTCATATTT

SEQ ID NO: 92
CGGACTACGACGAGTTTTTTGGGATT

SEQ ID NO: 93
ATAGGGCTCGGCTTCATGCG

SEQ ID NO: 94
ATATCACTATAGGGCTCGGCTTCATGC

SEQ ID NO: 95
TATAGGGCTCGGCTTCATGCG

SEQ ID NO: 96
GAGACCGGCTTTTTGGGATTTGC

SEQ ID NO: 97
AACTGAGACCGGCTTTTTGGGATTTG

SEQ ID NO: 98
tCtCCTTTCAGGAAGAGGCCCCCTTTT

SEQ ID NO: 99
CATCAGTCCTTTTTCCCCGACAAAAGG

SEQ ID NO: 100
CCATCAGTCCTTTTTCCCCGACAAAG

SEQ ID NO: 101
tCtCGGTTGAGCCGTGGTATTTTACGC

SEQ ID NO: 102
tCGCTACTGATCGTCGCCATGGTAAG

SEQ ID NO: 103
TTTCCTTACTCACCATGCAGTAAGTAAT

SEQ ID NO: 104
tCtCGTGCGCCAGTGTACTCTGCT

SEQ ID NO: 105
GTGCAGCACCTGTCTTTAGGTTCTTG

SEQ ID NO: 106
CGTGGACCTGTAGCCTATTTAGCATT

SEQ ID NO: 107
ATGTTTTAGAGATTTGCTCCACCTCGC

SEQ ID NO: 108
GCGGTATTGCATCTTTTTGTCCTT

SEQ ID NO: 109
AGCCGTGCAGCACCTGTTTT

SEQ ID NO: 110
tCCGAACTGAGAGAAGGTTTTGAGATTAGC

SEQ ID NO: 111
ACGGCCGGCTTTTTGCGA

SEQ ID NO: 112
GAGTTAAGCTCCAGGTTTTCACGC

SEQ ID NO: 113
TACGGCCGGCTTTTTGCGATT

SEQ ID NO: 114
TACATTTAGTTTTTCTCCCTGCACCATG

SEQ ID NO: 115
GTACATTTAGTTTTTCTCCCTGCACCAT

SEQ ID NO: 116
tCAAAGTTGAGCTTCGGCTTTTCAC

SEQ ID NO: 117
ACTGACAGAGTTTTACACCCCAAGGG

SEQ ID NO: 118
CGATCCGAACTGAGAATAGGTTTAAGAG

SEQ ID NO: 119
CAGCGTGCTGATCTGCGTTTACTAG

SEQ ID NO: 120
GCAACTCCCATTTTTGGGTTGGATG

SEQ ID NO: 121
TGAACTGAGGACGGTTTTATGGATTTGC

SEQ ID NO: 122
GAGCGTATGCGGTATTAGCGTAAGTTT

INFORMAL SEQUENCE LISTING

SEQ ID NO: 123
ACGGTATTAGCGCAACCCCTTT

SEQ ID NO: 124
GTTTGGCAACCCTTTGTACCGA

SEQ ID NO: 125
ATGTCAAGGGTAGGTAAGGTTTTTCG

SEQ ID NO: 126
GAACTACGAACAGCTTTTTGAGATTCGC

SEQ ID NO: 127
ATAATATCCGGTTTTAGCACTCCTTTCG

SEQ ID NO: 128
AAGCCCTCCTTTAGCACCTTAGTTTT

SEQ ID NO: 129
ATAGAGCTCGGCTTCATGCGGTATTAG

SEQ ID NO: 130
TATAGAGCTCGGCTTCATGCGGTATTAG

SEQ ID NO: 131
ATATCACTATAGAGGTCGGCTTCATGCG

SEQ ID NO: 132
GAACTGAGACGCACTTTTAGAGGTTGG

SEQ ID NO: 133
TGCAGCACCTTGTTTCAGGTCATTG

SEQ ID NO: 134
tCGCGTTTTCTTCCCAGATAAAAGCAGTTT

SEQ ID NO: 135
CatAAATTCCAtgTaCCcCatCGGc

SEQ ID NO: 136
CCGGAAACTTTCACCGCTGAC

SEQ ID NO: 137
tgTcAcATTCCgCCTaCCTCTAgtGTAt

SEQ ID NO: 138
eGTCAGTATCAAggGCAcTgCgata

SEQ ID NO: 139
CTcCGaccgTCTAGCcTca

SEQ ID NO: 140
TCGGTCTTTAGCATCGGACTTGAGAG

SEQ ID NO: 141
GgAATTCtACCcCCCTCTACGagAC

SEQ ID NO: 142
GGGTATTATCCCCAGTTTTCCGGG

SEQ ID NO: 143
GCCTTGGTGGGCTTTTACCCC

SEQ ID NO: 144
GAACTGAGAACGGTTTTTTCCGATTAGC

SEQ ID NO: 145
ATTCGACAGGGGTTTACGATCCGAA

SEQ ID NO: 146
CGGTATTAGCGGTCGTTTCCAACC

SEQ ID NO: 147
CGAAGGAACGGACTATCTCTAGTCTTTT

SEQ ID NO: 148
GTTAAGGIGTGAGTTTTCACGAACAACG

SEQ ID NO: 149
GCCATGCAGCACCTTGTTTCATG

SEQ ID NO: 150
GCTACTTGTGGAATTCCATTTTCTCCGT

SEQ ID NO: 151
GGTACCGCCGCTTTTGAGAG

SEQ ID NO: 152
GAACTGGGGCGCGCTTTTTG

SEQ ID NO: 153
TGAGCCAGGATCAAACTCTCCAGTTTTT

SEQ ID NO: 154
TTGCATGTCAAGCCTTGGTAAGGTTTTT

SEQ ID NO: 155
GAACTGGCGCCTCTTTTAAGGATTTG

SEQ ID NO: 156
GGCTTCGGCACCGATAGGTTTT

SEQ ID NO: 157
TGAGGACGGCTTTTTGGGATTGG

SEQ ID NO: 158
TGAGACTGGTTTTTTGAGATTAGCTTGG

SEQ ID NO: 159
TTTTTTT

SEQ ID NO: 160
/5AmMC12/TTTTTTT

SEQ ID NO: 161
CATTGATCGCAACGTTCAATTTAAT

SEQ ID NO: 162
TGGTCTTTCTGCATTCCTGGA

SEQ ID NO: 163
CTATGATCCCAATCTAACTTCCACATACC

SEQ ID NO: 164
AGRGTTYGATYMTGGCTCAG

SEQ ID NO: 165
RGYTACCTTGTTACGACTT

SEQ ID NO: 166
TCTAAGCGGTGCGGTAATCT

SEQ ID NO: 167
TTCTTTCCAGGTGCTCCAAC

SEQ ID NO: 168
TGGGCACATACACGCAGGA

SEQ ID NO: 169
TTGGTGGAGTGATTTGTCTGCT

SEQ ID NO: 170
TCTAAGGGCATCACAGACCTG

SEQ ID NO: 171
TCGGCCCTTAAATAGCCCGGTCCGC

SEQ ID NO: 172
TTAACCTACTAAATAGTGCTGCTAGC

What is claimed is:

1. A method for characterizing a population of microbial strains in a sample, wherein different microbial strains in the population comprise polynucleotides with different microbe-identifying sequences, the method comprising:

(i) amplifying polynucleotides obtained from the sample to form a plurality of amplicons, wherein the amplicons comprise microbe-identifying sequences;

(ii) combining the amplicons with a plurality of micro-beads, wherein each microbead of the plurality of microbeads has a lanthanide spectral signature and a plurality of copies of a capture polynucleotide immobilized on the microbead, wherein each of the plurality of copies of the capture polynucleotide immobilized on any one microbead of the plurality of microbeads comprises a same predetermined sequence that is paired with the lanthanide spectral signature of the one microbead, such that the plurality of copies of the capture polynucleotide immobilized on the one microbead can be identified based on the lanthanide spectral signature of the one microbead, wherein the plurality of microbeads comprises one or more subpopulations, each characterized by a particular lanthanide spectral signature, such that microbeads of different subpopulations have different lanthanide spectral signatures, wherein, for each microbead of at least some of the plurality of microbeads, the plurality of copies of the capture polynucleotide immobilized on the microbead comprises a sequence substantially complementary to a microbe-identifying sequence of one or more of the plurality of amplicons, wherein the combining is conducted under conditions in which at least some of the plurality of amplicons hybridize to the plurality of copies of the capture polynucleotide immobilized on at least some of the plurality of microbeads, thereby producing captured amplicons, and wherein the plurality of amplicons is labeled with one or more signal-generating moieties prior to, simultaneously with, or after being captured onto at least some of the plurality of microbeads, such that microbeads comprising immobilized signal-generating moieties are produced; wherein the magnitude of signal detected from an individual microbead corresponds to the amount of the plurality of amplicons captured on the individual microbead, (iii) measuring the magnitude of the signal from the microbeads comprising immobilized signal-generating moieties;

(iv) for each of the plurality of microbeads, determining the lanthanide spectral signature, thereby determining the microbe-identifying sequences of the captured amplicons;

(v) generating a pattern of measured amount of hybridization of the captured amplicons to individual capture polynucleotides;

(vi) for each microbial strain of a plurality of microbial strains, comparing the pattern of hybridization measured in (v) to a predicted pattern of hybridization of amplicons to each of the individual capture polynucleotides, the predicted pattern of hybridization corresponding to the microbial strain, wherein predicting hybridization of the amplicons to a capture polynucleotide comprises calculating the Gibbs free energy of hybridization;

(vii) correlating the pattern of hybridization measured in (v) to the predicted pattern of hybridization for each microbial strain of the plurality of microbial strains to identify the microbial strain that has a predicted pattern of hybridization that has the strongest correlation with the pattern of hybridization measured in (v); and (viii) determining that the microbial strain identified in (vii) is present in the population of microbial strains in the sample if the strongest correlation is greater than a predetermined threshold.

2. The method of claim 1, wherein the plurality of microbeads comprises at least 50 different spectral signatures and immobilized capture polynucleotides comprising at least 50 different predetermined sequences; and/or the combining in step (ii) comprises hybridizing amplicons to at least 50 microbeads having different spectral signatures and different capture polynucleotides.

3. The method of claim 1, wherein the one or more signal-generating moieties produce a fluorescent or chemiluminescent signal; and/or the plurality of amplicons is labeled during the amplifying in step (i).

4. The method of claim 1, wherein at least one of the microbe-identifying sequences in the amplicons comprises a bacterial 16S ribosomal RNA (rRNA) gene sequence.

5. The method of claim 4, wherein the amplification in step (i) is conducted using primer pairs that hybridize to conserved regions flanking one or more variable regions in a bacterial 16S rRNA gene sequence.

6. The method of claim 4, wherein the amplification in step (i) comprises amplifying one or more of a V3 variable region, a V4 variable region, or a V6 variable region in a bacterial 16S rRNA gene sequence.

7. The method of claim 1, wherein the population of microbial strains comprises one or more species selected from the group consisting of *Pseudomonas, Streptococcus, Staphylococcus, Neisseria, Acinetobacter, Escherichia, Enterobacter, Klebsiella, Haemophilus, Proteus, Serratia, Enterococcus,* and *Listeria*.

8. The method of claim 1, wherein each lanthanide A spectral signature comprises a europium (Eu) signal, a dysprosium (Dy) signal, a samarium (Sm) signal, a cerium (Ce) signal, a terbium (Tb) signal, a lanthanum (La) signal, a praseodymium (Pr) signal, a neodymium (Nd) signal, a gadolinium (Gd) signal, a holmium (Ho) signal, an erbium (Er) signal, a thulium (Tm) signal, an ytterbium (Yb) signal, or a combination thereof.

9. The method of claim 1, wherein the one or more signal-generating moieties comprise fluorescent labels.

10. The method of claim 1, wherein the sample is from blood, cerebrospinal fluid, lymph, or urine.

11. The method of claim 1, wherein step (iii) occurs prior to step (iv).

12. The method of claim 1, wherein step (iii) occurs simultaneously with step (iv).

13. The method of claim 1, wherein step (iii) occurs after step (iv).

14. The method of claim 1, wherein each of the plurality of microbeads comprises a plurality of lanthanide nanoparticles.

15. The method of claim 14, wherein the plurality of lanthanide nanoparticles comprises a lanthanide-doped host lattice.

16. The method of claim 15, wherein each of the plurality of microbeads further comprises a crosslinked polymer, and wherein the capture polynucleotides are covalently bonded to the crosslinked polymer.

17. The method of claim 1, wherein the plurality of microbeads is dispersed on a microscope slide prior to step (iii) or step (iv).

18. The method of claim 1, further comprising separating uncaptured amplicons from the plurality of microbeads.

19. The method of claim 6, further comprising separating the microbeads comprising immobilized signal-generating moieties from microbeads not comprising immobilized signal-generating moieties.

20. The method of claim 6, wherein the amplification step (i) comprises amplifying the V3 variable region and the V6 variable region.

* * * * *

SEQUENCE LISTING

<160> NUMBER OF SEQ ID NOS: 295

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gtgccagcmg ccgcggtaa                                                          19

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
ggactachvg ggtwtctaat                                                         20

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gtgccagcmg ccgcggtaa                                                          19

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ggactachvg ggtwtctaat                                                         20

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
tggagcatgt ggtttaattc ga                                                      22

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
tggagcatgt ggtttaattc ga                                                      22

-continued

```
<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (12)..(12)
<223> OTHER INFORMATION: a, c, t, g, unknown or other

<400> SEQUENCE: 7
agctgacgac anccatgca                                                   19

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (12)..(12)
<223> OTHER INFORMATION: a, c, t, g, unknown or other

<400> SEQUENCE: 8
agctgacgac anccatgca                                                   19

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
ccagactcct acgggaggca g                                                21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ccagactcct acgggaggca g                                                21

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
cgtattaccg cggctgctg                                                   19

<210> SEQ ID NO 12
<211> LENGTH: 19
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 12
cgtattaccg cggctgctg                                                           19

<210> SEQ ID NO 13
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13 tttttttttct agagttgtca aaggatgtca agatttggta ag                                42

<210> SEQ ID NO 14
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ctagagttgt caaaggatgt caagatttgg taag                                          34

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15 ttttttttacc tgtgtctgag ttcccgaagg                                              30

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
acctgtgtct gagttcccga agg                                                      23

<210> SEQ ID NO 17
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17 tttttttttgg aaagttctca gcatgtcaag gc                                           32

<210> SEQ ID NO 18
<211> LENGTH: 24
<212> TYPE: DNA
<213> ORGANISM: Artificial Sequence
<220> FEATURE:
```

-continued

<223> OTHER INFORMATION: Description of Artificial Sequence: Synthetic
     oligonucleotide

<400> SEQUENCE: 18
ggaaagttct cagcatgtca aggc                                              24

<210> SEQ ID NO 19
<211> LENGTH: 38
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 19 ttttttttgcc gtattaacta aatcctcctc gcttaaag                             38

<210> SEQ ID NO 20
<211> LENGTH: 31
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 20
gccgtattaa ctaaatcctc ctcgcttaaa g                                     31

<210> SEQ ID NO 21
<211> LENGTH: 36
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 21 tttttttttgg aaagtttcta gtatgtcaag gccagg                               36

<210> SEQ ID NO 22
<211> LENGTH: 28
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 22
ggaaagtttc tagtatgtca aggccagg                                         28

<210> SEQ ID NO 23
<211> LENGTH: 32
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 23 ttttttttgca cctgtatcta gattcccgaa gg                                   32

<210> SEQ ID NO 24
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 24
gcacctgtat ctagattccc gaagg                                         25

<210> SEQ ID NO 25
<211> LENGTH: 36
<212> TYPE: DNA
<213> ORGANISM: Artificial Sequence
<220> FEATURE:
<223> OTHER INFORMATION: Description of Artificial Sequence: Synthetic
        oligonucleotide

<400> SEQUENCE: 25 tttttttttgc taagttctct ggatgtcaag agtagg                            36

<210> SEQ ID NO 26
<211> LENGTH: 28
<212> TYPE: DNA
<213> ORGANISM: Artificial Sequence
<220> FEATURE:
<223> OTHER INFORMATION: Description of Artificial Sequence: Synthetic
        oligonucleotide

<400> SEQUENCE: 26
gctaagttct ctggatgtca agagtagg                                      28

<210> SEQ ID NO 27
<211> LENGTH: 32
<212> TYPE: DNA
<213> ORGANISM: Artificial Sequence
<220> FEATURE:
<223> OTHER INFORMATION: Description of Artificial Sequence: Synthetic
        oligonucleotide

<400> SEQUENCE: 27
tttttttgac ctggtaaggt tctttcgcgt tg                                 32

<210> SEQ ID NO 28
<211> LENGTH: 25
<212> TYPE: DNA
<213> ORGANISM: Artificial Sequence
<220> FEATURE:
<223> OTHER INFORMATION: Description of Artificial Sequence: Synthetic
        oligonucleotide

<400> SEQUENCE: 28
gacctggtaa ggttctttcg cgttg                                         25

<210> SEQ ID NO 29
<211> LENGTH: 31
<212> TYPE: DNA
<213> ORGANISM: Artificial Sequence
<220> FEATURE:
<223> OTHER INFORMATION: Description of Artificial Sequence: Synthetic
        oligonucleotide

<400> SEQUENCE: 29 tttttttttag agtggtcaaa ggatgtcaag a                                 31

<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence: Synthetic
        oligonucleotide

<400> SEQUENCE: 30
agagtggtca aaggatgtca aga                                              23

<210> SEQ ID NO 31
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
ttttttttgt ctcacagttc ccgaaggca                                       29

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
gtctcacagt tcccgaaggc a                                                21

<210> SEQ ID NO 33
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
ttttttttgg aaagttctgt ggatgtcaag a                                    31

<210> SEQ ID NO 34
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
ggaaagttct gtggatgtca aga                                              23

<210> SEQ ID NO 35
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35 ttttttttgtc actctgtccc ccgaagg                                        27

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 36
gtcactctgt cccccgaagg                                                           20

<210> SEQ ID NO 37
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37 ttttttttgag gggtcagagg atgtcaagat ttg                                          33

<210> SEQ ID NO 38
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
gaggggtcag aggatgtcaa gatttg                                                   26

<210> SEQ ID NO 39
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
ttttttttgt cacctctgtc ccgaaggaaa                                               30

<210> SEQ ID NO 40
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
gtcacctctg tcccgaagga aa                                                       22

<210> SEQ ID NO 41
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
ttttttttag agcggtcaga gggatgtcaa g                                             31

<210> SEQ ID NO 42
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
```
agagcggtca gagggatgtc aag                                          23

<210> SEQ ID NO 43
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43 ttttttttgag caaaggtatt aactttactc ccttcc                           36

<210> SEQ ID NO 44
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
gagcaaaggt attaacttta ctcccttcc                                    29

<210> SEQ ID NO 45
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45 ttttttttgat gtgcacagtt acttacacat atgt                             34

<210> SEQ ID NO 46
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
gatgtgcaca gttacttaca catatgt                                      27

<210> SEQ ID NO 47
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47 ttttttttgta ttaacttact gcccttcctc ccaac                            35

<210> SEQ ID NO 48
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
gtattaactt actgcccttc ctcccaac                                    28

<210> SEQ ID NO 49
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49 ttttttttcta tctctaggta gccgtattaa ctaaa                           35

<210> SEQ ID NO 50
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
ctatctctag gtagccgtat taactaaa                                    28

<210> SEQ ID NO 51
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51 ttttttttagg gatgaacagt tactctcatc ct                             32

<210> SEQ ID NO 52
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
agggatgaac agttactctc atcct                                       25

<210> SEQ ID NO 53
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53 ttttttttcgg cagggttatt aaccctgtcg c                              31

<210> SEQ ID NO 54
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
cggcagggtt attaaccctg tcgc                                        24

-continued

```
<210> SEQ ID NO 55
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
ttttttttcg acaaggttat taaccttatc g                                    31

<210> SEQ ID NO 56
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
cgacaaggtt attaacctta tcg                                             23

<210> SEQ ID NO 57
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57 ttttttttcgg ccgccgatat tggcaacggc ctt                                 33

<210> SEQ ID NO 58
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
cggccgccga tattggcaac ggcctt                                          26

<210> SEQ ID NO 59
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59 ttttttttgac gtgcatagtt acttacacat ttg                                 33

<210> SEQ ID NO 60
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
gacgtgcata gttacttaca catttg                                          26
```

-continued

```
<210> SEQ ID NO 61
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
tttttttcag tgtgaacttt ccactctcac actc                                34

<210> SEQ ID NO 62
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
cagtgtgaac tttccactct cacactc                                        27

<210> SEQ ID NO 63
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
ggactacagg ggtatctaat cccttttg                                       28

<210> SEQ ID NO 64
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
ggtgacaggg gtttacaatc cgag                                           24

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
gcgttgcacc atcagggttt                                                20

<210> SEQ ID NO 66
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
cggcttcatg cagtcgagtt g                                              21
```

```
<210> SEQ ID NO 67
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
cagtgtactc cgctccgaag ag                                              22

<210> SEQ ID NO 68
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
agtaactccg aacaacgctt gc                                              22

<210> SEQ ID NO 69
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
gaactgtggc tgggtttgat gagatt                                         26

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
catgcaggcg agtttcagcc                                                20

<210> SEQ ID NO 71
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
gtttcgctcc cctttgtccc aa                                             22

<210> SEQ ID NO 72
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
gtcaattcat ttgagtttta accttgcg                                       28

<210> SEQ ID NO 73
```

```
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
agctcgccag ttttggatgc ag                                                22

<210> SEQ ID NO 74
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
agtcgacatc gtttacggcg tg                                                22

<210> SEQ ID NO 75
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
gaactgagat ggctttggga gattcg                                            26

<210> SEQ ID NO 76
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
gagccaggat caaactctca ggttt                                             25

<210> SEQ ID NO 77
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
gtctggccga catcgtttac gg                                                22

<210> SEQ ID NO 78
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
ttagcttttg tagccttttt ccctgctg                                          28

<210> SEQ ID NO 79
<211> LENGTH: 28
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
cgaactcgag ttttgcagta tctaaagc                                      28

<210> SEQ ID NO 80
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
aggaattccg cttgcttttc ccg                                           23

<210> SEQ ID NO 81
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
cagttactag ttttacccta ggcagc                                        26

<210> SEQ ID NO 82
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
gaactgagat agtgtttaag ggattcgc                                      28

<210> SEQ ID NO 83
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
acgtagaagg gtttattccc aaacaaaa                                      28

<210> SEQ ID NO 84
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
tacgaccggt ttttcgggat tgg                                           23

<210> SEQ ID NO 85
<211> LENGTH: 26
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 85
atgtcaaagg tgggtaaggt ttttcg                                       26

<210> SEQ ID NO 86
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
gactacgacc ggttttttcgg gattg                                       25

<210> SEQ ID NO 87
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
gatcgctccc ttttacctct cgg                                          23

<210> SEQ ID NO 88
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
ggtaaggttc ttcggtttgc atcgaatt                                     28

<210> SEQ ID NO 89
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
gtactccagt ccgacggttt cg                                           22

<210> SEQ ID NO 90
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
tgcagcacct gtgtttaggt t                                            21

<210> SEQ ID NO 91
<211> LENGTH: 28
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 91
gttctagcaa gctagcactc tcatattt                                      28

<210> SEQ ID NO 92
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
cggactacga cgagtttttt gggatt                                        26

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
atagggctcg gcttcatgcg                                               20

<210> SEQ ID NO 94
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
atatcactat agggctcggc ttcatgc                                       27

<210> SEQ ID NO 95
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
tatagggctc ggcttcatgc g                                             21

<210> SEQ ID NO 96
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
gagaccggct ttttgggatt tgc                                           23

<210> SEQ ID NO 97
<211> LENGTH: 26
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 97
aactgagacc ggcttttttgg gatttg                                        26

<210> SEQ ID NO 98
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
tctcctttca ggaagaggcc ccctttt                                        27

<210> SEQ ID NO 99
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
catcagtcct ttttccccga caaaagg                                        27

<210> SEQ ID NO 100
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
ccatcagtcc tttttccccg acaaaag                                        27

<210> SEQ ID NO 101
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
tctcggttga gccgtggtat tttacgc                                        27

<210> SEQ ID NO 102
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
tcgctactga tcgtcgccat ggtaag                                         26

<210> SEQ ID NO 103
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 103
tttccttact caccatgcag taagtaat                                    28

<210> SEQ ID NO 104
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
tctcgtgcgc cagtgtactc tgct                                        24

<210> SEQ ID NO 105
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
gtgcagcacc tgtctttagg ttcttg                                      26

<210> SEQ ID NO 106
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
cgtggacggt agcctattta gcatt                                       25

<210> SEQ ID NO 107
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
atgttttaga gatttgctcc acctcgc                                     27

<210> SEQ ID NO 108
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
gcggtattgc atctttttgt cctt                                        24

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
agccgtgcag cacctgtttt                                            20

<210> SEQ ID NO 110
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
tccgaactga gagaaggttt tgagattagc                                 30

<210> SEQ ID NO 111
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
acggccggct ttttgcga                                              18

<210> SEQ ID NO 112
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
gagttaagct ccaggttttc acgc                                       24

<210> SEQ ID NO 113
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
tacggccggc tttttgcgat t                                          21

<210> SEQ ID NO 114
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
tacatttagt ttttctccct gcaccatg                                   28

<210> SEQ ID NO 115
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 115
gtacatttag tttttctccc tgcaccat                                              28

<210> SEQ ID NO 116
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
tcaaagttga gcttcggctt ttcac                                                 25

<210> SEQ ID NO 117
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
actgacagag ttttacaccc caaggg                                               26

<210> SEQ ID NO 118
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
cgatccgaac tgagaatagg tttaagag                                             28

<210> SEQ ID NO 119
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
cagcgtgctg atctgcgttt actag                                                25

<210> SEQ ID NO 120
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
gcaactccca tttttgggtt ggatg                                                25

<210> SEQ ID NO 121
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
```

```
tgaactgagg acggttttat ggatttgc                                          28

<210> SEQ ID NO 122
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
gagcgtatgc ggtattagcg taagttt                                           27

<210> SEQ ID NO 123
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
acggtattag cgcaacccct tt                                                22

<210> SEQ ID NO 124
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
gtttggcaac cctttgtacc ga                                                22

<210> SEQ ID NO 125
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
atgtcaaggg taggtaaggt ttttcg                                            26

<210> SEQ ID NO 126
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
gaactacgaa cagctttttg agattcgc                                          28

<210> SEQ ID NO 127
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
```
ataatatccg gttttagcac tcctttcg                                                                    28

<210> SEQ ID NO 128
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
aagccctcct ttagcacctt agtttt                                                                      26

<210> SEQ ID NO 129
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
atagagctcg gcttcatgcg gtattag                                                                     27

<210> SEQ ID NO 130
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
tatagagctc ggcttcatgc ggtattag                                                                    28

<210> SEQ ID NO 131
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
atatcactat agagctcggc ttcatgcg                                                                    28

<210> SEQ ID NO 132
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
gaactgagac gcacttttag aggttgg                                                                     27

<210> SEQ ID NO 133
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
tgcagcacct tgtttcaggt cattg                                                                       25

```
<210> SEQ ID NO 134
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
tcgcgttttc ttcccagata aaagcagttt                                          30

<210> SEQ ID NO 135
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
cataaattcc atgtacccca tcggc                                               25

<210> SEQ ID NO 136
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
ccggaaactt tcaccgctga c                                                   21

<210> SEQ ID NO 137
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
tgtcacattc cgcctacctc tagtgtat                                            28

<210> SEQ ID NO 138
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
cgtcagtatc aagggcactg cgata                                               25

<210> SEQ ID NO 139
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
ctccgaccgt ctagcctca                                                      19
```

<210> SEQ ID NO 140
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
tcggtcttta gcatcggact tgagag                                          26

<210> SEQ ID NO 141
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
ggaattctac cccctctac gagac                                           25

<210> SEQ ID NO 142
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
gggtattatc cccagttttc cggg                                           24

<210> SEQ ID NO 143
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
gccttggtgg gctttacc c                                                21

<210> SEQ ID NO 144
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
gaactgagaa cggttttttc cgattagc                                       28

<210> SEQ ID NO 145
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
attcgacagg ggtttacgat ccgaa                                          25

<210> SEQ ID NO 146
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
cggtattagc ggtcgtttcc aacc                                                   24

<210> SEQ ID NO 147
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
cgaaggaacg gactatctct agtctttt                                               28

<210> SEQ ID NO 148
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
gttaagctgt gagttttcac gaacaacg                                               28

<210> SEQ ID NO 149
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
gccatgcagc accttgtttc atg                                                    23

<210> SEQ ID NO 150
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
gctacttgtg gaattccatt ttctccgt                                               28

<210> SEQ ID NO 151
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
ggtaccgccg cttttgagag                                                        20

<210> SEQ ID NO 152

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
gaactggggc gcgctttttg                                                       20

<210> SEQ ID NO 153
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
tgagccagga tcaaactctc cagttttt                                              28

<210> SEQ ID NO 154
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
ttgcatgtca agccttggta aggttttt                                              28

<210> SEQ ID NO 155
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
gaactggcgc ctcttttaag gatttg                                                26

<210> SEQ ID NO 156
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
ggcttcggca ccgataggtt tt                                                    22

<210> SEQ ID NO 157
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
tgaggacggc ttttttgggat tgg                                                  23

<210> SEQ ID NO 158
<211> LENGTH: 28
```

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
tgagactggt tttttgagat tagcttgg                                                28

<210> SEQ ID NO 159
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159 ttttttt                                                                       7

<210> SEQ ID NO 160
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160 ttttttt                                                                       7

<210> SEQ ID NO 161
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
cattgatcgc aacgttcaat ttaat                                                   25

<210> SEQ ID NO 162
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
tggtctttct gcattcctgg a                                                       21

<210> SEQ ID NO 163
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
ctatgatccc aatctaactt ccacatacc                                              29

<210> SEQ ID NO 164
<211> LENGTH: 20
<212> TYPE: DNA

-continued

```
<213> ORGANISM: Artificial Sequence
<220> FEATURE:
<223> OTHER INFORMATION: Description of Artificial Sequence: Synthetic
      oligonucleotide

<400> SEQUENCE: 164
agrgttygat ymtggctcag                                                20

<210> SEQ ID NO 165
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
rgytaccttg ttacgactt                                                 19

<210> SEQ ID NO 166
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
tctaagcggt gcggtaatct                                                20

<210> SEQ ID NO 167
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
ttctttccag gtgctccaac                                                20

<210> SEQ ID NO 168
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168
tgggcacata cacgcagga                                                 19

<210> SEQ ID NO 169
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
ttggtggagt gatttgtctg ct                                             22

<210> SEQ ID NO 170
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 170
tctaagggca tcacagacct g                                               21

<210> SEQ ID NO 171
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
tcggccctta aatagcccgg tccgc                                           25

<210> SEQ ID NO 172
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
ttaacctact aaatagtgct gctagc                                          26

<210> SEQ ID NO 173
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
aggtggtgca tggttgtcgt cagc                                            24

<210> SEQ ID NO 174
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174
acaggtgctg catggctgtc gtcagct                                         27

<210> SEQ ID NO 175
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
gcttattctg cgagtaacgt ccactatctc taggt                                35

<210> SEQ ID NO 176
<211> LENGTH: 28
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 176
gcgggtaacg tcaattgctg cggttatt                                                       28

<210> SEQ ID NO 177
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
gcgggtaacg tcaatgagca aaggtattaa cttt                                                34

<210> SEQ ID NO 178
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
gtcaggggac gttcagttac taacgt                                                         26

<210> SEQ ID NO 179
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
gtcaagggat gaacagttac tctcatcctt gtt                                                 33

<210> SEQ ID NO 180
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180
tagccggtgc ttcttctgta tttaacgtca atttg                                              35

<210> SEQ ID NO 181
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
ggtgcttctt ctgcgggtaa cgtcaatgaa taag                                               34

<210> SEQ ID NO 182
<211> LENGTH: 32
<212> TYPE: DNA
<213> ORGANISM: Artificial Sequence
<220> FEATURE:
<223> OTHER INFORMATION: Description of Artificial Sequence: Synthetic -continued oligonucleotide

<400> SEQUENCE: 182
gcgggtaacg tcaatcgatg aggttattaa cc                                    32

<210> SEQ ID NO 183
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
ggttagatac cgtcaaggga caagcagtta ctctt                                 35

<210> SEQ ID NO 184
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
gtcaaaacag caaggtatta acttactgcc ctt                                   33

<210> SEQ ID NO 185
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
gggtattaac cttatcacct tcctccccgc tg                                    32

<210> SEQ ID NO 186
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
gtcacttggt agattttcca ctcctaccaa cgtt                                  34

<210> SEQ ID NO 187
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
gtcaagacgt gcatagttac ttacacattt gtt                                   33

<210> SEQ ID NO 188
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide -continued

<400> SEQUENCE: 188
gcgagtaacg tcaattgatg agcgtattaa gctca                          35

<210> SEQ ID NO 189
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
gtcacagtgt gaactttcca ctctcacact cgtt                           34

<210> SEQ ID NO 190
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190 gttgcccca ttgccgaaga tt                                         22

<210> SEQ ID NO 191
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191
tgaaaacttc cgtggatgtc aagaccaggt aagg                           34

<210> SEQ ID NO 192
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 192
gaaggggaag ctctatctct agagtggtca aagg                           34

<210> SEQ ID NO 193
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193
tgcaaacttc ttaggatgtc aagagtaggt aagg                           34

<210> SEQ ID NO 194
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide -continued

<400> SEQUENCE: 194
agcatctctg ctaaattctc tggatgtcaa gag                                    33

<210> SEQ ID NO 195
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 195
ctccagagtg gtcaaaggat gtcaagacct gg                                     32

<210> SEQ ID NO 196
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 196
tcctctatct ctaaaggatt cgctggatgt caag                                   34

<210> SEQ ID NO 197
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197
gaagagaaag cctatctcta ggccggtcag aagg                                   34

<210> SEQ ID NO 198
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 198
ggggaaggct ctatctctag agttgtcaaa ggatg                                  35

<210> SEQ ID NO 199
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 199
ggggaaaact ctatctctag aggggtcaga ggatg                                  35

<210> SEQ ID NO 200
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 200

-continued ggaaagttct ctggatgtca agagtaggta agg                                    33

<210> SEQ ID NO 201
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 201
gaaggaaaac tctatctcta gagcggtcag aggg                                   34

<210> SEQ ID NO 202
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 202
gaagtaaaac tctatctcta gagcgggcat cggg                                   34

<210> SEQ ID NO 203
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 203
gctgcgccac taaagcctca aaggc                                             25

<210> SEQ ID NO 204
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 204
ggtcgattta acgcgttagc ctccggaag                                         29

<210> SEQ ID NO 205
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(23)
<223> OTHER INFORMATION: a, c, t, g, unknown or other

<400> SEQUENCE: 205
ggcggtcgac ttaacgcgtt anntccggaa g                                      31

<210> SEQ ID NO 206
<211> LENGTH: 29
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 206
ggcggtcgat ttatcacgtt agctacggg                                       29

<210> SEQ ID NO 207
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 207
aacgcgttag ctccggaagc cactc                                           25

<210> SEQ ID NO 208
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 208
gttagctgcg ccactaagat ctcaaggatc                                      30

<210> SEQ ID NO 209
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209
gaagccacgg ttcaagacca caacctctaa at                                   32

<210> SEQ ID NO 210
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 210
ggagtgctta atgcgttagc tacggcacta aa                                   32

<210> SEQ ID NO 211
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 211
gagtgcttaa tgcgttagct ccggcactaa g                                    31

<210> SEQ ID NO 212
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 212
tttttttgct tattctgcga gtaacgtcca ctatctctag gt          42

<210> SEQ ID NO 213
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 213
tttttttgcg ggtaacgtca attgctgcgg ttatt          35

<210> SEQ ID NO 214
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 214
tttttttgcg ggtaacgtca atgagcaaag gtattaactt t          41

<210> SEQ ID NO 215
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 215
tttttttgtc aggggacgtt cagttactaa cgt          33

<210> SEQ ID NO 216
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 216
tttttttgtc aagggatgaa cagttactct catccttgtt          40

<210> SEQ ID NO 217
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 217 tttttttttag ccggtgcttc ttctgtattt aacgtcaatt tg          42

<210> SEQ ID NO 218
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 218
tttttttggt gcttcttctg cgggtaacgt caatgaataa g                41

<210> SEQ ID NO 219
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 219
tttttttgcg ggtaacgtca atcgatgagg ttattaacc                  39

<210> SEQ ID NO 220
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 220
tttttttggt tagataccgt caagggacaa gcagttactc tt              42

<210> SEQ ID NO 221
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 221
tttttttgtc aaaacagcaa ggtattaact tactgccctt                 40

<210> SEQ ID NO 222
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 222
tttttttggg tattaacctt atcaccttcc tccccgctg                  39

<210> SEQ ID NO 223
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 223
tttttttgtc acttggtaga ttttccactc ctaccaacgt t               41

<210> SEQ ID NO 224
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 224
tttttttgtc aagacgtgca tagttactta cacatttgtt                                    40

<210> SEQ ID NO 225
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 225
tttttttgcg agtaacgtca attgatgagc gtattaagct ca                                 42

<210> SEQ ID NO 226
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 226
tttttttgtc acagtgtgaa ctttccactc tcacactcgt t                                  41

<210> SEQ ID NO 227
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 227
tttttttgtt gcccccattg ccgaagatt                                                29

<210> SEQ ID NO 228
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 228 tttttttga aaacttccgt ggatgtcaag accaggtaag g                                   41

<210> SEQ ID NO 229
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 229
tttttttgaa ggggaagctc tatctctaga gtggtcaaag g                                  41

<210> SEQ ID NO 230
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 230 tttttttttgc aaacttctta ggatgtcaag agtaggtaag g                                41

<210> SEQ ID NO 231
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 231
tttttttagc atctctgcta aattctctgg atgtcaagag                                  40

<210> SEQ ID NO 232
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 232
tttttttctc cagagtggtc aaaggatgtc aagacctgg                                   39

<210> SEQ ID NO 233
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 233
tttttttgga aagttctcag catgtcaagg c                                           31

<210> SEQ ID NO 234
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 234 tttttttttcc tctatctcta aaggattcgc tggatgtcaa g                               41

<210> SEQ ID NO 235
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 235
tttttttgaa gagaaagcct atctctaggc cggtcagaag g                                41

<210> SEQ ID NO 236
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 236
tttttttggg gaaggctcta tctctagagt tgtcaaagga tg                               42

-continued

```
<210> SEQ ID NO 237
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 237 ttttttggg gaaaactcta tctctagagg ggtcagagga tg                          42

<210> SEQ ID NO 238
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 238 ttttttgga aagttctctg gatgtcaaga gtaggtaagg                             40

<210> SEQ ID NO 239
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 239 ttttttgaa ggaaaactct atctctagag cggtcagagg g                           41

<210> SEQ ID NO 240
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 240 ttttttgaa gtaaaactct atctctagag cgggcatcgg g                           41

<210> SEQ ID NO 241
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 241 ttttttgct gcgccactaa agcctcaaag gc                                     32

<210> SEQ ID NO 242
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 242 ttttttggt cgatttaacg cgttagcctc cggaag                                 36
```

<210> SEQ ID NO 243
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (29)..(30)
<223> OTHER INFORMATION: a, c, t, g, unknown or other

<400> SEQUENCE: 243
tttttttggc ggtcgactta acgcgttann tccggaag                                38

<210> SEQ ID NO 244
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 244
tttttttggc ggtcgattta tcacgttagc tacggg                                  36

<210> SEQ ID NO 245
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 245
tttttttaac gcgttagctc cggaagccac tc                                      32

<210> SEQ ID NO 246
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 246
tttttttgtt agctgcgcca ctaagatctc aaggatc                                 37

<210> SEQ ID NO 247
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 247
tttttttgaa gccacggttc aagaccacaa cctctaaat                               39

<210> SEQ ID NO 248
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 248
tttttttgga gtgcttaatg cgttagctac ggcactaaa                                    39

<210> SEQ ID NO 249
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 249
tttttttgag tgcttaatgc gttagctccg gcactaag                                     38

<210> SEQ ID NO 250
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 250
tttttttgtt tctagtatgt caaggccagg taa                                          33

<210> SEQ ID NO 251
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 251
tttttttaat ccatctctgg aaagttctgt g                                            31

<210> SEQ ID NO 252
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 252
ttttttttcc ccgaagggaa agctcta                                                 27

<210> SEQ ID NO 253
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 253
tttttttctt tgcccccgaa gggg                                                    24

<210> SEQ ID NO 254
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 254
tttttttcat tctcatctct gaaaacttcc gtg                                    33

<210> SEQ ID NO 255
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 255
tttttttcat ctctgcaaac ttcttaggat gtc                                    33

<210> SEQ ID NO 256
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 256
tttttttcaa agcatctctg ctaaattctc tgg                                    33

<210> SEQ ID NO 257
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 257
tttttttgtc tccagagtgg tcaaaggatg                                        30

<210> SEQ ID NO 258
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 258
tttttttcac tcctctatct ctaaaggatt cgc                                    33

<210> SEQ ID NO 259
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 259
tttttttatc tctggaaagt tctcagcatg tc                                     32

<210> SEQ ID NO 260
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 260
tttttttgaa agttctctgg atgtcaagag tag                                    33

<210> SEQ ID NO 261
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 261
tttttttagg ctctatctct agagttgtca aag                                    33

<210> SEQ ID NO 262
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 262
tttttttcta tctctagagg ggtcagagga t                                      31

<210> SEQ ID NO 263
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 263
tttttttgtc acttctgctc cgaagagaaa                                        30

<210> SEQ ID NO 264
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 264 tttttttttct gtcccgaagg aaaactctat ct                                    32

<210> SEQ ID NO 265
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 265
tttttttccg atgtaccgaa gtaaaactct atc                                    33

<210> SEQ ID NO 266
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 266
tttttttacg tccactatct ctaggtatta act                                    33

```
<210> SEQ ID NO 267
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 267
tttttttcgg ttattaacca caacaccttc c                                    31

<210> SEQ ID NO 268
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 268
tttttttgtt cagttactaa cgtccttgtt ctt                                  33

<210> SEQ ID NO 269
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 269
tttttttgtc aagggatgaa cagttactct cat                                  33

<210> SEQ ID NO 270
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 270
tttttttggt attaacttta ctcccttcct ccc                                  33

<210> SEQ ID NO 271
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 271
tttttttttc ctcaataccg aaagaacttt aca                                  33

<210> SEQ ID NO 272
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 272
tttttttgaa taaggttatt aacctcactc cct                                  33
```

<210> SEQ ID NO 273
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 273
tttttttgat gaggttatta accttaacgc ctt                                    33

<210> SEQ ID NO 274
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 274
tttttttgca gttactctta tccttgttct tct                                    33

<210> SEQ ID NO 275
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 275
tttttttagg gtattaacct tatcaccttc ctc                                    33

<210> SEQ ID NO 276
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 276 tttttttttca aaacagcaag gtattaactt act                                   33

<210> SEQ ID NO 277
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 277
tttttttaac gtcaattgat gagcgtatta agc                                    33

<210> SEQ ID NO 278
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 278
tttttttgtc aagatgtgca cagttactta cac                                    33

<210> SEQ ID NO 279

-continued

```
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 279 tttttttttag attttccact cctaccaacg ttc                                33

<210> SEQ ID NO 280
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 280
tttttttcac tctcacactc gttcttctct ta                                 32

<210> SEQ ID NO 281
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 281
tttttttcca ccatcattct tctctaacaa cag                                33

<210> SEQ ID NO 282
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 282
atcgaacatt                                                          10

<210> SEQ ID NO 283
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 283
aattggctta                                                          10

<210> SEQ ID NO 284
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 284
ccttatgtat                                                          10

<210> SEQ ID NO 285
<211> LENGTH: 10
```

-continued

```
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 285
gctgcatgag                                                        10

<210> SEQ ID NO 286
<211> LENGTH: 128
<212> TYPE: DNA
<213> ORGANISM: Pseudomonas aeruginosa

<400> SEQUENCE: 286
tggagcatgt ggtttaattc gaagcaacgc gaagaacctt acctggcctt gacatgctga    60
gaactttcca gagatggatt ggtgccttcg ggaactcaga cacaggtgct gcatggctgt   120
cgtcagct                                                         128

<210> SEQ ID NO 287
<211> LENGTH: 128
<212> TYPE: DNA
<213> ORGANISM: Streptococcus pneumoniae

<400> SEQUENCE: 287
tggagcatgt ggtttaattc gaagcaacgc gaagaacctt accaggtctt gacatccctc    60
tgaccgctct agagatagag ctttccttcg ggacagaggt gacaggtggt gcatggttgt   120
cgtcagct                                                         128

<210> SEQ ID NO 288
<211> LENGTH: 130
<212> TYPE: DNA
<213> ORGANISM: Staphylococcus epidermis

<400> SEQUENCE: 288
tggagcatgt ggtttaattc gaagcaacgc gaagaacctt accaaatctt gacatcctct    60
gacccctcta gagatagagt tttcccccttc gggggacaga gtgacaggtg gtgcatggtt   120
gtcgtcagct                                                       130

<210> SEQ ID NO 289
<211> LENGTH: 129
<212> TYPE: DNA
<213> ORGANISM: Enterococcus faecium

<400> SEQUENCE: 289
tggagcatgt ggtttaattc gaagcaacgc gaaagaacct taccaggtct tgacatcctt    60
tgaccactct agagatagag cttcccccttc gggggcaaag tgacaggtgg tgcatggttg   120
tcgtcagct                                                        129

<210> SEQ ID NO 290
<211> LENGTH: 130
<212> TYPE: DNA
<213> ORGANISM: Staphylococcus aureus

<400> SEQUENCE: 290
tggagcatgt ggtttaattc gaagcaacgc gaagaacctt accaaatctt gacatccttt    60
gacaactcta gagatagagc tttcccccttc gggggacaaa gtgacaggtg gtgcatggtt   120
gtcgtcagct                                                       130
```

<210> SEQ ID NO 291
<211> LENGTH: 128
<212> TYPE: DNA
<213> ORGANISM: Neisseria gonorrhoeae

<400> SEQUENCE: 291
tggatgatgt ggattaattc gatgcaacgc gaagaacctt acctggtttt gacatgtgcg      60
gaatcctccg gagacggagg agtgccttcg ggagccgtaa cacaggtgct gcatggctgt     120
cgtcagct                                                              128

<210> SEQ ID NO 292
<211> LENGTH: 128
<212> TYPE: DNA
<213> ORGANISM: Acinetobacter baumannii

<400> SEQUENCE: 292
tggagcatgt ggtttaattc gatgcaacgc gaagaacctt acctggcctt gacatactag      60
aaactttcca gagatggatt ggtgccttcg ggaatctaga tacaggtgct gcatggctgt     120
cgtcagct                                                              128

<210> SEQ ID NO 293
<211> LENGTH: 128
<212> TYPE: DNA
<213> ORGANISM: Echerichia coli

<400> SEQUENCE: 293
tggagcatgt ggtttaattc gatgcaacgc gaagaacctt acctggtctt gacatccacg      60
gaagttttca gagatgagaa tgtgccttcg ggaaccgtga gacaggtgct gcatggctgt     120
cgtcagct                                                              128

<210> SEQ ID NO 294
<211> LENGTH: 128
<212> TYPE: DNA
<213> ORGANISM: Enterobacter cloacae

<400> SEQUENCE: 294
tggagcatgt ggtttaattc gatgcaacgc gaagaacctt acctactctt gacatccaga      60
gaacttagca gagatgcttt ggtgccttcg ggaactctga gacaggtgct gcatggctgt     120
cgtcagct                                                              128

<210> SEQ ID NO 295
<211> LENGTH: 128
<212> TYPE: DNA
<213> ORGANISM: Klebsiella pneumoniae

<400> SEQUENCE: 295
tggagcatgt ggtttaattc gatgcaacgc gaagaacctt acctggtctt gacatccaca      60
gaactttcca gagatggatt ggtgccttcg ggaactgtga gacaggtgct gcatggctgt     120
cgtcagct                                                              128